United States Patent
Wang et al.

(10) Patent No.: US 11,466,273 B2
(45) Date of Patent: *Oct. 11, 2022

(54) MONOCARBOXYLATE TRANSPORTER 4 ($MCT_4$) ANTISENSE OLIGONUCLEOTIDE (ASO) INHIBITORS FOR USE AS THERAPEUTICS IN THE TREATMENT OF CANCER

(71) Applicant: THE UNIVERSITY OF BRITISH COLUMBIA, Vancouver (CA)

(72) Inventors: Yuzhuo Wang, Vancouver (CA); Stephen Yiu Chuen Choi, Vancouver (CA)

(73) Assignee: The University of British Columbia, Vancouver (CA)

( * ) Notice: Subject to any disclaimer, the term of this patent is extended or adjusted under 35 U.S.C. 154(b) by 0 days.

This patent is subject to a terminal disclaimer.

(21) Appl. No.: 17/099,516

(22) Filed: Nov. 16, 2020

(65) Prior Publication Data

US 2021/0395733 A1  Dec. 23, 2021

Related U.S. Application Data

(63) Continuation of application No. 15/779,419, filed as application No. PCT/CA2016/000296 on Nov. 30, 2016, now Pat. No. 10,889,814.

(60) Provisional application No. 62/260,837, filed on Nov. 30, 2015.

(51) Int. Cl.

| | |
|---|---|
| *C12N 15/11* | (2006.01) |
| *C12N 15/113* | (2010.01) |
| *A61K 31/7088* | (2006.01) |
| *C07H 21/04* | (2006.01) |
| *A61K 31/713* | (2006.01) |
| *A61P 35/00* | (2006.01) |
| *A61K 31/337* | (2006.01) |

(52) U.S. Cl.
CPC .......... *C12N 15/113* (2013.01); *A61K 31/337* (2013.01); *A61K 31/7088* (2013.01); *A61K 31/713* (2013.01); *A61P 35/00* (2018.01); *C07H 21/04* (2013.01); *C12N 2310/11* (2013.01); *C12N 2310/14* (2013.01); *C12N 2310/321* (2013.01); *C12N 2310/341* (2013.01); *C12N 2320/31* (2013.01)

(58) Field of Classification Search
None
See application file for complete search history.

(56) References Cited

U.S. PATENT DOCUMENTS

| | | |
|---|---|---|
| 10,889,814 B2 | 1/2021 | Wang et al. |
| 2003/0000597 A1 | 1/2003 | Matsumoto et al. |
| 2005/0255114 A1 | 11/2005 | Labat et al. |
| 2005/0255487 A1 | 11/2005 | Khvorov et al. |
| 2007/0003575 A1 | 1/2007 | Bentwich et al. |
| 2009/0280124 A1 | 11/2009 | Labat et al. |
| 2010/0209914 A1 | 8/2010 | Bigwood et al. |

FOREIGN PATENT DOCUMENTS

| | | |
|---|---|---|
| WO | WO 2005054582 | 6/2005 |
| WO | WO 2000049937 | 8/2008 |
| WO | WO 2016046640 | 3/2016 |

OTHER PUBLICATIONS

Albertsen, et al (2005) "20-year outcomes following conservative management of clinically localized prostate cancer"; JAMA 293; pp. 2095-2101.
Badrising, S., et al (2014) "Clinical activity and tolerability of enzalutamide (MDV3100) in patients with metastatic, castration-resistant prostate cancer who progress after docetaxel and abiraterone treatment"; Cancer 120(7); pp. 968-975.
Beltran, et al. (2011) "Molecular characterization of neuroendocrine prostate cancer and identification of new drug targets"; Cancer Discov 1 (6); pp. 487-495.
Bishr M and Saad F. (2013) "Overview of the latest treatments for castration-resistant prostate cancer"; Nat Rev Urol. 10(9); pp. 522-528.
Chiang, et al (2014) "GATA2 as a potential metastasis-driving gene in prostate cancer"; Oncotarget 5(2); pp. 451-461.
Choi, S.Y., et al (2013) "Cancer-generated lactic acid: a regulatory, immunosuppressive metabolite?"; J Pathol 230(4); pp. 350-355.
Choi, S.Y., et al (2014) "Lessons from patient-derived xenografts for better in vitro modeling of human cancer"; Adv Drug Deliv Rev 79-80,; pp. 222-237.
Choi, S.Y.C. et al, "The MCT4 Gene: A Novel, Potential Target for Therapy of Advanced Prostate Cancer"; Clinical Cancer Research 22(11); Jun. 1, 2016; pp. 2721-2733.
Claessens F, et al (2014) "Emerging mechanisms of enzalutamide resistance in prostate cancer"; Nat Rev Urol. 11(12); pp. 712-716.
De Bono, et al. (2011) "Abiraterone and increased survival in metastatic prostate cancer"; N Engl J Med 364(21); pp. 1995-2005.
Dias, N., and Stein, C.A. (2002) "Antisense oligonucleotides: basic concepts and mechanisms"; Mol Cancer Ther 1(5); pp. 347-355.
Dimmer, et al (2000) "The low-affinity monocarboxylate transporter MCT4 is adapted to the export of lactate in highly glycolytic cells"; Biochem J 350 Pt 1; pp. 219-227.
Doherty, J.R., and Cleveland, J.L. (2013). "Targeting lactate metabolism for cancer therapeutics"; J Clin Invest 123(9); pp. 3685-3692.

(Continued)

*Primary Examiner* — Ekaterina Poliakova-Georgantas
(74) *Attorney, Agent, or Firm* — Bozicevic, Field & Francis LLP; Shweta Chandra

(57) ABSTRACT

Provided herein are compositions, method and uses for modulating MCT4 activity or for the treatment of cancer. The compositions comprise antisense oligonucleotides (ASO) for administration to a cancer cell, wherein the cancer cell may be characterized by elevated expression of MCT4. The cancer may be selected from one or more of: prostate cancer; renal cell carcinoma; breast cancer; cervical cancer; liver cancer; bladder cancer; and small cell lung cancer pr. The prostate cancer may be castration-resistant prostate cancer (CRPC).

23 Claims, 25 Drawing Sheets

Specification includes a Sequence Listing.

(56) References Cited

OTHER PUBLICATIONS

Fisel, P. et al. (2013) "DNA methylation of the SLC16A3 promoter regulates expression of the human lactate transporter MCT4 in renal cancer with consequences for clinical outcome"; Clin Cancer Res 19(18); pp. 5170-5181.
Gallagher, S.M. et al, "Monocarboxylate Transporter 4 Regulates Maturation and Trafficking of CD147 to the Plasma Membrane in the Metastatic Breast Cancer Cell Line MDA-MB-231"; Cancer Research, 67(9); May 1, 2007; pp. 4182-4189.
Gravel, S.P., et al (2014). "Stable isotope tracer analysis in isolated mitochondria from mammalian systems"; Metabolites 4(2); pp. 166-183.
Gravel, S.P., et al (2014). "Serine deprivation enhances antineoplastic activity of biguanides"; Cancer Res 74(24); pp. 7521-7533.
Halestrap, A.P. (2013) "The SLC16 gene family—structure, role and regulation in health and disease"; Mol Aspects Med 34; pp. 337-349.
Hanahan, D., and Weinberg, R.A. (2011) "Hallmarks of cancer: the next generation"; Cell 144(5); pp. 646-674.
Hao, J.,et al. (2010) "Co-expression of CD147 (Emmprin), CD44v3-10, MDR1 and monocarboxylate transporters is associated with prostate cancer drug resistance and progression"; Br J Cancer 103(7); pp. 1008-1018.
Izumi, H. et al. (2011) "Monocarboxylate transporters 1 and 4 are involved in the invasion activity of human lung cancer cells"; Cancer Science, 102(5); pp. 1007-1013.
Jadvar, H. (2009) "Molecular imaging of prostate cancer with 18F-fluorodeoxyglucose PET"; Nat Rev Urol 6(6); pp. 317-323.
Koochekpour, S., et al. (2012) "Serum glutamate levels correlate with Gleason score and glutamate blockade decreases proliferation, migration, and invasion and induces apoptosis in prostate cancer cells"; Clin Cancer Res 18(21); pp. 5888-5901.
Lin D, et al (2013) "Lessons from in-vivo models of castration-resistant prostate cancer"; Curr Opin Urol. 23(3); pp. 214-219.
Lisanti, et al (2013) "Stromal glycolysis and MCT4 are hallmarks of DCIS progression to invasive breast cancer"; Cell Cycle 12(18); pp. 2935-2936.
Loriot, Y., et al. (2013) "Antitumour activity of abiraterone acetate against metastatic castration-resistant prostate cancer progressing after docetaxel and enzalutamide (MDV3100)"; Ann Oncol 24(7); pp. 1807-1812.
Manning Fox, J.E., et al (2000) "Characterisation of human monocarboxylate transporter 4 substantiates its role in lactic acid efflux from skeletal muscle"; J Physiol 529 Pt 2,; pp. 285-293.
Marchiq, I.,et al (2015) "Genetic disruption of lactate/$H_+$ symporters (MCTs) and their subunit CD147/BASIGIN sensitizes glycolytic tumor cells to phenformin"; Cancer Res 75(1); pp. 171-180.
Matveeva, O.V., et al (2000) "Identification of sequence motifs in oligonucleotides whose presence is correlated with antisense activity"; Nucleic Acids Res 28(15); pp. 2862-2865.
Morice, W.G. (2007) "The immunophenotypic attributes of NK cells and NK-cell lineage lymphoproliferative disorders"; Am J Clin Pathol 127(6); pp. 881-886.
Mullick, A.E., et al (2011) "Antisense oligonucleotide reduction of apoB-ameliorated atherosclerosis in LDL receptor-deficient mice"; J Lipid Res 52(5); pp. 885-896.
Nadal, R., et al. (2014) "Small cell carcinoma of the prostate"; Nat Rev Urol 11(4); pp. 213-219.
Ning, Y.M., et al. (2013) "Enzalutamide for treatment of patients with metastatic castration-resistant prostate cancer who have previously received docetaxel: U.S. Food and Drug Administration drug approval summary"; Clin Cancer Res 19(22); pp. 6067-6073.
Ovens, M.J., et al (2010) "AR-C155858 is a potent inhibitor of monocarboxylate transporters MCT1 and MCT2 that binds to an intracellular site involving transmembrane helices 7-10"; Biochem J 425(3); pp. 523-530.
Parks, et al (2013) "Disrupting proton dynamics and energy metabolism for cancer therapy"; Nat Rev Cancer 13(9); pp. 611-623.

Peek AS and Behlke MA. (2007) "Design of active small interfering RNAs"; Curr Opin Mol Ther. 9(2); pp. 110-118.
Pértega-Gomes, et al. (2011) "Monocarboxylate transporter 4 (MCT4) and CD147 overexpression is associated with poor prognosis in prostate cancer"; BMC Cancer 11:312; pp. 1-9.
Petrylak et al (2004) "Docetaxel and estramustine compared with mitoxantrone and prednisone for advanced refractory prostate cancer"; N Engl J Med. 351(15); pp. 1513-1520.
Samuel, et al. (2006) "Targeting foxol in mice using antisense oligonucleotide improves hepatic and peripheral insulin action"; Diabetes 55; pp. 2042-2050.
Sanitá, P. et al. (2014) Tumor-stroma metabolic relationship based on lactate shuttle can sustain prostate cancer progression; BMC Cancer 14, pp. 2-14.
Shultz, et al (2007) "Humanized mice in translational biomedical research"; Nat Rev Immunol 7; pp. 118-130.
Siegel, R.L. et al (2015) :"Cancer statistics, 2015"; CA Cancer J Clin 65; pp. 5-29.
Tannock IF, et al .(2004) "Docetaxel plus prednisone or mitoxantrone plus prednisone for advanced prostate cancer"; N Engl J Med. 351(15); pp. 1502-1512 1512.
Tennakoon, J.B., et al. (2014) "Androgens regulate prostate cancer cell growth via an AMPK-PGC-1α-mediated metabolic switch"; Oncogene 33; pp. 5251-5261.
Thomas, C., et al (2011) "Transcription factor Stat5 knockdown enhances androgen receptor degradation and delays castration-resistant prostatecancer progression in vivo"; Mol Cancer Ther 10; pp. 347-359.
Ullah, M.S., et al (2006) "The plasma membrane lactate transporter MCT4, but not MCT1, is up-regulated by hypoxia through a HIF-1alpha-dependent mechanism"; J Biol Chem 281; pp. 9030-9037.
Vandesompele, J., et al (2002) "Accurate normalization of real-time quantitative RT-PCR data by geometric averaging of multiple internal control genes"; Genome Biol 3(7), Research0034.1; pp. 1-7.
Vaz, C.V., et al (2012) "Androgen-responsive and nonresponsive prostate cancer cells present a distinct glycolytic metabolism profile"; Int J Biochem Cell Biol 44; pp. 2077-2084.
Wang, Y., et al. (2005) An orthotopic metastatic prostate cancer model in SCID mice via grafting of a transplantable human prostate tumor line; Lab Invest 85, pp. 1392-1404.
Yuan, T.C., et al (2007). "Neuroendocrine-like prostate cancer cells: neuroendocrine transdifferentiation of prostate adenocarcinoma cells"; Endocr Relat Cancer 14; pp. 531-547.
Zhang, Y., and Yang, J.M. (2013) "Altered energy metabolism in cancer: a unique opportunity for therapeutic intervention"; Cancer Biol Ther 14; pp. 81-89.
Alves, V.A., et al., (2014) "Characterization of monocarboxylate transporter activity in hepatocellular carcinoma" World J Gastroenterol, 20:33 pp. 11780-11787.
Ames et al., (2020) "CAIX forms a transport metabolon with monocarboxylate transporters in human breast cancer cells" Oncogene 39: pp. 1710-1723.
Anderson et al., (2018) "The net acid extruders NHE1, NBCn1 and MCT4 promote mammary tumor growth through distinct but overlapping mechanisms" International Journal of Cancer 142: pp. 2529-2542.
Baek et al., (2014) "MCT4 Defines a Glycolytic Subtype of Pancreatic Cancerwith Poor Prognosis and Unique Metabolic Dependencies" Cell Reports 9: pp. 2233-2249.
Baenke, F., et al., (2015) "Functional screening identifies MCT4 as a key regulator of breast cancer cell metabolism and survival" J Pathol, 237:2 pp. 152-165.
Baltazar et al., (2014) "Monocarboxylate transporters as targets and mediators in cancer therapy response" Histology and Histopathology, 29: pp. 1511-1524.
Benjamin et al., (2018) "Dual Inhibition of the Lactate TransportersMCT1 and MCT4 is Synthetic Lethal with Metformin due to NAD+ Depletion in Cancer Cells" Cell Press 25: pp. 2047-3058.

(56) References Cited

OTHER PUBLICATIONS

Bisetto et al., (2018) "Monocarboxylate Transporter 4 (MCT4) Knockout Mice Have Attenuated 4NQO Induced Carcinogenesis; A Role for MCT4 in Driving Oral Squamous Cell Cancer" Frontiers in Oncology, 8:324 pp. 1-13.
Bovenzi, C.D., et al., (2015) "Prognostic Indications of Elevated MCT4 and CD147 across Cancer Types: A Meta-Analysis" Biomedeical Research International 24243: pp. 1-15.
Brandstetter et al., (2021) "Targeted sensitization of tumor cells for radiation through monocarboxylate transporters 1 and 4 inhibition in vitro" Clinical Oral Investigations 25: pp. 295-310.
Chen, H.L., et al., (2018) "Aberrant MCT4 and GLUT1 expression is correlated with early recurrence and poor prognosis of hepatocellular carcinoma after hepatectomy" Cancer Med, 7:11 pp. 5339-5350.
Cheng et al., (2018) "Prognostic value of monocarboxylate transporter 4 in patients with esophageal squamous cell carcinoma" Oncology Reports 40: pp. 2906-2915.
Cho, E., et al., (2015) "18F-FDG PET CT as a prognostic factor in hepatocellular carcinoma" Turk J Gastroenterol, 26:4 pp. 344-350.
Choi, S.Y., et al., (2018) "The MCT4 Gene: A Novel, Potential Target for Therapy of Advanced Prostate Cancer" Clinical Cancer Research 22:11 pp. 2721-2733.
Draoui et al., (2014) "Antitumor Activity of 7-Aminocarboxycoumarin Derivatives, a New Class of Potent Inhibitors of Lactate Influx but Not Efflux" Molecular Cancer Therapeutics 13:6 pp. 1410-1418.
Gao, H.J., et al., (2015) Monocarboxylate transporter 4 predicts poor prognosis in hepatocellular carcinoma and is associated with cell proliferation and migration. J Cancer Res Clin Oncol, 41(7): pp. 1151-1162.
Gerlinger, M., et al., (2012) "Genome-wide RNA interference analysis of renal carcinoma survival regulators identifies MCT4 as a Warburg effect metabolic target" J Pathol, 227:2 pp. 146-156.
Guan et al., (2020) "In Vitro and In Vivo Efficacy of AZD3965 and Alpha-Cyano-4-Hydroxycinnamic Acid in the Murine 4T1 Breast Tumor Model" American Association of Pharmaceutical Scientists Journal, 22: 84 pp. 1-11.
Guo et al., (2019) "Monocarboxylate transporter 1 and monocarboxylate transporter 4 in cancer-endothelial co-culturing microenvironments promote proliferation, migration, and invasion of renal cancer cells" Cancer Cell International 19:170 pp. 1-11.
Halestrap, (2013) "The SLC16 gene family—Structure, role and regulation in health and disease" Molecular Aspects of Medicine, 34: pp. 337-349.
Hamaguchi, T., et al., (2008) "Glycolysis module activated by hypoxia-inducible factor 1 alpha is related to the aggressive phenotype of hepatocellular carcinoma" Int J Oncol, 33:4 pp. 725-731.
Hasegawa et al. "Lactate Transporter Monocarboxylate Transporter 4 Induces Bone Pain in Head and Neck Squamous Cell Carcinoma" International Journal of Molecular Sciences 19:3317 pp. 1-13.
Hong et al., (2016) "MCT1 Modulates Cancer Cell Pyruvate Export and Growth of Tumors that Co-expressMCT1 and MCT4" Cell Reports, 14: pp. 1590-1601.
Javaeed et al., (2019) "MCT4 has a potential to be used as a prognostic biomarker—a systematic review and meta-analysis" Oncol Rev, 13:403 pp. 88-96.
Jonnalagadda et al., (2019) "Novel N,N-dialkyl cyanocinnamic acids as monocarboxylate transporter 1 and 4 inhibitors" Oncotarget, 10:24 pp. 2355-2368.
Khan et al., (2020) "Targeting metabolic activity in high-risk neuroblastoma through Monocarboxylate Transporter 1 (MCT1) inhibition" Oncogene, 39: pp. 3555-3570.

Kim et al., (2018) "MCT4Expression Is a Potential Therapeutic Target in Colorectal Cancer with Peritoneal Carcinomatosis" Molecular Cancer Therapeutics, 17:4 pp. 838-848.
Kong et al., (2016) "Monocarboxylate Transporters MCT1 and MCT4 Regulate Migration and Invasion of Pancreatic Ductal Adenocarcinoma Cells" Pancreas Journal, 45:7 pp. 1036-1047.
Kuo et al., (2020) "Monocarboxylate Transporter 4 is a Therapeutic Target in Non-small Cell Lung Cancerwith Aerobic Glycolysis Preference" Molecular Therapy: Oncolytics 18: 189-201.
Lai et al., (2020) "Monocarboxylate Transporter 4 Regulates Glioblastoma Motility and Monocyte Binding Ability" Cancers, 12:380 pp. 1-20.
Lee et al., (2016) "MCT4 as a potential therapeutic target for metastatic gastric cancer with peritoneal carcinomatosis" Oncotarget 7:28 pp. 43492-43503.
Lim, K.S., et al., (2014) Inhibition of monocarboxylate transporter-4 depletes stem-like glioblastoma cells and inhibits HIF transcriptional response in a lactate-independent manner. Oncogene, 33:4433-4441.
Long et al., (2018) "Downregulation of MCT4 for lactate exchange promotes the cytotoxicity of NK cells in breast carcinoma" Cancer Medicine, 7: pp. 4690-4700.
Marchiq et al., (2014) "Genetic Disruption of Lactate/Hp Symporters (MCTs) and Their Subunit CD147/BASIGIN Sensitizes Glycolytic Tumor Cells to Phenformin" Cancer Research, 75:1 171-180.
Martins, D., et al., (2013) "Loss of caveolin-1 and gain of MCT4 expression in the tumor stroma: key events in the progression from an in situ to an invasive breast carcinoma" Cell Cycle, 12:16 pp. 2684-2690.
Miranda-Gonçalves, V., et al., (2013) Monocarboxylate transporters (MCTs) in gliomas: expression and exploitation as therapeutic targets. Neuro Oncol, 15(2): pp. 172-188.
Morais-Santos, F., et al., (2015) Targeting lactate transport suppresses in vivo breast tumour growth. Oncotarget, pp. 1-13.
Payen et al., (2019) "Monocarboxylate transporters in cancer" Molecular Metabolism, 33: pp. 48-66.
Pereira-Nunes et al., (2020) "Targeting lactate production and efflux in prostate cancer" Molecular Basis of Disease 1866: 9 pages.
Puri et al., (2020) "Monocarboxylate transporter 1 and 4 inhibitors as potential therapeutics for treating solid tumours: A review with structure activity relationship insights" 199: pp. 1-14.
Shi, H., et al., (2015) "Overexpression of monocarboxylate anion transporter 1 and 4 in T24-induced cancer-associated fibroblasts regulates the progression of bladder cancer cells in a 3D microfluidic device" Cell Cycle, 2015. 14:19 pp. 3058-3065.
Simões-Sousa, S., et al., (2016) Prognostic significance of monocarboxylate transporter expression in oral cavity tumors. Cell Cycle, 2016. 15(14): pp. 1865-1873.
Spina et al., (2020) "MCT4 regulates de novo pyrimidine biosynthesis in GBM in a lactate-independent manner" Neuro-Oncology Advances, 2:1 pp. 1-11.
Todenhöfer et al., (2018) "Selective Inhibition of the Lactate Transporter MCT4 Reduces Growth of Invasive Bladder Cancer" Cancer Biology and Translational Studies, 17:12 pp. 2746-2755.
Voss et al., (2017) "Disruption of the monocarboxylate transporter-4-basigin interaction inhibits the hypoxic response, proliferation, and tumor progression" Scientific Reports, 7: 4292 pp. 1-14.
Zhao et al., (2019) "Targeted inhibition of MCT4 disrupts intracellular pH homeostasis and confers self-regulated apoptosis on hepatocellular carcinoma" Experimental Cell Research, 384 pp. 1-11.
Zhu et al., (2014) "Monocarboxylate Transporter 4 Facilitates Cell Proliferation and Migration and is Associated with Poor Prognosis in Oral Squamous Cell Carcinoma Patients" PLoS One, 9:1 e87904 pp. 1-11.

US 11,466,273 B2

MONOCARBOXYLATE TRANSPORTER 4 (MCT₄) ANTISENSE OLIGONUCLEOTIDE (ASO) INHIBITORS FOR USE AS THERAPEUTICS IN THE TREATMENT OF CANCER

CROSS REFERENCE TO RELATED APPLICATION

This application is a continuation of U.S. application Ser. No. 15/779,419, filed May 25, 2018, now U.S. Pat. No. 10,889,814, issued on Jan. 12, 2021, which application is a U.S. national phase application under 35 U.S.C. § 371 of International Application Serial No. PCT/CA2016/000296, filed Nov. 30, 2016, which application claims the benefit of U.S. Provisional Patent Application Ser. No. 62/260,837 filed on 30 Nov. 2015, entitled "ANTISENSE OLIGO-NUCLEOTIDES AS MONOCARBOXYLATE TRANSPORTER 4 THERAPEUTIC COMPOSITIONS AND METHODS FOR THEIR USE IN THE TREATMENT OF CANCER".

TECHNICAL FIELD

The present invention provides compounds, compositions and methods for modulating the expression of monocarboxylate transporter 4 (MCT4). In particular, this invention relates to antisense oligonucleotides (ASOs) capable of modulating human MCT4 mRNA expression, and their uses and methods for the treatment obrieff various indications, including various cancers. In particular the invention relates to therapies and methods of treatment for cancers such as prostate cancer, including castration-resistant prostate cancer (CRPC).

BACKGROUND

Prostate cancer is the most common non-cutaneous cancer and the second leading cause of cancer-related deaths for males in the Western world (Siegel R, et al., 2012, 62(1): 10-29). Prostate cancers are initially androgen-dependent, and while androgen deprivation therapy (ADT) can induce marked tumor regression, resistance to ADT inevitably emerges, leading to castration-resistant prostate cancer (CRPC). The current standard care for treating CRPC is systemic, docetaxel-based chemotherapy, increasing the overall survival of patients by about 2 months compared to mitoxantrone-based therapy (Petrylak D P, et al., N Engl J Med. 2004; 351(15):1513-1520; Tannock I F, et al., N Engl J Med. 2004; 351(15):1502-1512). Recently, sipuleucel-T, cabazitaxel, abiraterone, MDV3100 and Radium-223 have shown more prolonged overall survival benefit and are approved by the FDA for treatment of the CRPC (Bishr M and Saad F., Nat Rev Urol. 2013; 10(9):522-528). Although the efficacy of metastatic castration-resistant prostate cancer (mCRPC) treatment has recently been improved by using more powerful chemotherapeutics targeting the androgen receptor (AR)-signaling axis, such as enzalutamide (Ning et al., 2013) and abiraterone (de Bono et al., 2011), the overall survival of patients has only marginally increased (Badrising et al., 2014; Loriot et al., 2013; Tannock et al., 2004). Moreover, it is thought that further improved versions of such drugs can promote transdifferentiation of prostatic adenocarcinoma to neuroendocrine prostate cancer (NEPC), a subtype of the disease that is currently incurable (Beltran et al., 2011; Nadal et al., 2014; Yuan et al., 2007) However, none of these drugs are curative and they incrementally improve overall survival. The establishment of more effective therapeutic targets and drugs, specifically those targeting the molecular drivers of metastatic CRPC and mCRPC, is of critical importance for improved disease management and patient survival (Lin D, et al., Curr Opin Urol. 2013; 23(3):214-219).

There is increasing evidence that targeting reprogrammed energy metabolism of cancers offers a unique approach for effective therapeutic intervention (Zhang and Yang, 2013). For glucose utilization, cancer cells, as distinct from normal resting cells, in general have a preference for glycolysis coupled to lactic acid production, i.e. a process called aerobic glycolysis or the Warburg effect (Warburg, 1956). This leads to elevated glucose consumption, a near-universal property of primary and metastatic cancers. In addition, aberrant utilization of glutamine, also leading to elevated lactic acid production, has been observed to be highly common for cancers (Koochekpour et al., 2012). These metabolic energy pathways lead to increased lactic acid secretion by the cancer cells into their microenvironment, facilitating multiple oncogenic, lactate-stimulated processes, including tissue invasion/metastasis, neo-angiogenesis and responses to hypoxia (Choi et al., 2013; Choi et al., 2014; Doherty and Cleveland, 2013; Ullah et al., 2006). Furthermore, lactic acid-induced acidification of the cancer cell microenvironment (to pH 6.0-6.5) can lead to suppression of local host anticancer immunity (Choi et al., 2013; Parks et al., 2013). The phenomenon of enhanced glucose metabolism by cancers is most commonly exploited clinically by 18F-fluorodeoxyglucose positron emission tomography (FDG-PET). Although this imaging technique is not generally used for prostate cancer (Jadvar, 2009), there is evidence suggesting that glucose metabolism of prostate cancer cells is increased by AR signaling and progression to treatment resistance (Tennakoon et al., 2014; Vaz et al., 2012). As such, targeting the aerobic glycolytic pathway could be effective for treating advanced prostate cancers.

The monocarboxylate transporter (MCT) family consists of plasma membrane transporter proteins involved in the transport of lactic acid and other metabolic monocarboxylates. In particular, the cellular efflux of lactic acid/H+ is thought to be predominantly mediated by MCT4 (SLC16A3) (Dimmer et al., 2000). Expression of MCT4 has been associated with highly glycolytic cells (Halestrap, 2013; Manning Fox et al., 2000; Ullah et al., 2006), and elevated expression of MCT4 in tumours is clinically relevant as it has been associated with poor patient prognosis in multiple types of cancer (Fisel et al., 2013; Lisanti et al., 2013; Ohno et al., 2014), including prostate cancer (Hao et al., 2010; Pertega-Gomes et al., 2011). Furthermore, elevated MCT4 expression may be important in cancer-stroma interactions facilitating prostate cancer progression (Sanita et al., 2014). This information, together with the cancer growth-promoting ability of cancer-generated lactic acid, suggests that inhibition of the expression or function of MCTs provides a promising therapeutic strategy for a wide variety of neoplasms (Marchiq et al., 2015). However, a therapeutic strategy specifically targeting MCT4-mediated efflux of lactic acid is still lacking.

Therapeutic options for castration resistant prostate cancer (CRPC) treatment have changed considerably with the recent FDA approvals of newer agents that improve patient survival. In particular, Enzalutamide (ENZ), a second generation androgen receptor antagonist approved for treating metastatic CRPC in post-docetaxel and more recently, pre-docetaxel setting. However, within 2 years of clinical practice, development of ENZ resistance was evident in majority of patients (Claessens et al. 2014) and no known therapies were shown to be effective to ENZ-resistant CRPC to-date. Thus, a novel therapeutic agent that can effectively suppress ENZ-resistant CRPC would be useful.

SUMMARY

The present invention is based in part on the discovery that the inhibition of MCT4 expression with MCT4 antisense oligonucleotides (ASOs) (SEQ ID NO:1-23 and SEQ ID NO:46-50) may be useful in the treatment of cancer. The inhibition of MCT4 expression with certain ASOs leads to reduced proliferation of cancer cells. Furthermore, that reduction in proliferation extends to castration-resistant prostate cancer (CRPC).

In a first aspect, there is provided a composition for the treatment of a cancer cell, the method including administering one or more oligonucleotides selected from SEQ ID NO:1-23 or SEQ ID NO:46-50 to the cell.

In a further aspect, there is provided a pharmaceutical composition, the composition including (a) an antisense oligonucleotide (ASO) may be selected from one or more oligonucleotides of SEQ ID NO:1-23 and SEQ ID NO:46-50; and (b) a pharmaceutically acceptable carrier.

In accordance with a further aspect, there is provided a commercial package including (a) an antisense oligonucleotide sequence described herein and a pharmaceutically acceptable carrier; and (b) instructions for the use thereof for modulating MCT4 activity.

In a further aspect, there is provided a commercial package, including: (a) an ASO may be selected from an oligonucleotide of SEQ ID NOs:1-23 or SEQ ID NOs:46-50; and (b) instructions for the treatment of cancer.

In a further aspect, there is provided a method of treating cancer, the method including administering an antisense oligonucleotide (ASO) which may have a sequence selected from one or more of: SEQ ID NOs:1-23 and SEQ ID NOs:46-49.

In a further aspect, there is provided a method of treating cancer, the method including administering an MCT4 antisense oligonucleotide (ASO) having a sequence selected from one or more of: SEQ ID NOs:1-23 and SEQ ID NOs:46-49.

In a further aspect, there is provided an antisense oligonucleotide (ASO), wherein the oligonucleotide may have a sequence selected from the following: (a) TCCCATGGCCAGGAGGGTTG (SEQ ID NO:1); (b) GTCCCGGAAGACGCTCAGGT (SEQ ID NO:2); (c) AAGGACGCAGCCACCATGCC (SEQ ID NO:3); (d) TTGGCGTAGCTCACCACGAA (SEQ ID NO:4); (e) AGATGCAGAAGACCACGAGG (SEQ ID NO:5); (f) CCACTCTGGAATGACACGGT (SEQ ID NO:6); (g) GTAGGAGAAGCCAGTGATGAC (SEQ ID NO:7); (h) AGCATGGCCAGCAGGATGGA (SEQ ID NO:8); (i) GGCTGGAAGTTGAGTGCCAA (SEQ ID NO:9); (j) CATGCCGTAGGAGATGCCAA (SEQ ID NO:10); (k) CTCAGGCTGTGGCTCTITGG (SEQ ID NO:11); (l) TAGCGGGTTCAGCATGATGA (SEQ ID NO:12); (m) AGCACGGCCCAGCCCCAGCC (SEQ ID NO:13); (n) GAGCTCCTTGAAGAAGACACT (SEQ ID NO:14); (o) CAGGATGGAGGAGATCCAGG (SEQ ID NO:15); (p) AGACCCCCACAAGCATGAC (SEQ ID NO:16); (q) GAAGTTGAGTGCCAAACCCAA (SEQ ID NO:17); (r) CCCGTTGGCCATGGGGCGCC (SEQ ID NO:18); (s) GCCAGCCCGTTGGCCATGGG (SEQ ID NO:19); (t) AGGAAGACAGGGCTACCTGC (SEQ ID NO:20); (u) GCACACAGGAAGACAGGGCT (SEQ ID NO:21); (v) CAGGGCACACAGGAAGACAG (SEQ ID NO:22); (w) CAGCAGTTGAGCAGCAGGCC (SEQ ID NO:23); (x) ATGGCCAGGAGGGTTG (SEQ ID NO:46); (y) CATGGCCAGGAGGGTT (SEQ ID NO:47); (z) CCATGGCCAGGAGGGT (SEQ ID NO:48); and (aa) CCCATGGCCAGGAGGG (SEQ ID NO:49).

In a further aspect, there is provided a pharmaceutical composition, the composition including (a) an antisense oligonucleotide (ASO) having a sequence selected from one or more of: SEQ ID NOs:1-23 and SEQ ID NOs:46-49; and (b) a pharmaceutically acceptable carrier.

In a further aspect, there is provided a use of an antisense oligonucleotide (ASO) having a sequence selected from one or more of: SEQ ID NOs:1-23 and SEQ ID NOs:46-49 for treating cancer.

In a further aspect, there is provided a use of an antisense oligonucleotide (ASO) having a sequence selected from one or more of: SEQ ID NOs:1-23 and SEQ ID NOs:46-49 in the manufacture of a medicament for treating cancer.

In a further aspect, there is provided a combination therapy, the combination comprising (a) an antisense oligonucleotide (ASO) having a sequence selected from one or more of: SEQ ID NOs:1-23 and SEQ ID NOs:46-49; and (b) Docetaxel. The combination therapy may further include a pharmaceutically acceptable carrier or excipient.

In a further aspect, there is provided a commercial package, including an ASO having a sequence selected from one or more of: SEQ ID NOs:1-23 and SEQ ID NOs:46-49; and instructions for the treatment of cancer.

The antisense oligonucleotide (ASO) may have the sequence of SEQ ID NOs:1-23 or SEQ ID NOs:46-49. The antisense oligonucleotide (ASO) may have the sequence of SEQ ID NO:1. The antisense oligonucleotide (ASO) may have the sequence of SEQ ID NO:2. The antisense oligonucleotide (ASO) may have the sequence of SEQ ID NO:3. The antisense oligonucleotide (ASO) may have the sequence of SEQ ID NO:4. The antisense oligonucleotide (ASO) may have the sequence of SEQ ID NO:5. The antisense oligonucleotide (ASO) may have the sequence of SEQ ID NO:6. The antisense oligonucleotide (ASO) may have the sequence of SEQ ID NO:7. The antisense oligonucleotide (ASO) may have the sequence of SEQ ID NO:8. The antisense oligonucleotide (ASO) may have the sequence of SEQ ID NO:9. The antisense oligonucleotide (ASO) may have the sequence of SEQ ID NO:10. The antisense oligonucleotide (ASO) may have the sequence of SEQ ID NO:11. The antisense oligonucleotide (ASO) may have the sequence of SEQ ID NO:12. The antisense oligonucleotide (ASO) may have the sequence of SEQ ID NO:13. The antisense oligonucleotide (ASO) may have the sequence of SEQ ID NO:14. The antisense oligonucleotide (ASO) may have the sequence of SEQ ID NO:15. The antisense oligonucleotide (ASO) may have the sequence of SEQ ID NO:16. The antisense oligonucleotide (ASO) may have the sequence of SEQ ID NO:17. The antisense oligonucleotide (ASO) may have the sequence of SEQ ID NO:18. The antisense oligonucleotide (ASO) may have the sequence of SEQ ID NO:19. The antisense oligonucleotide (ASO) may have the sequence of SEQ ID NO:20. The antisense oligonucleotide (ASO) may have the sequence of SEQ ID NO:21. The antisense oligonucleotide (ASO) may have the sequence of SEQ ID NO:22. The antisense oligonucleotide (ASO) may have the sequence of SEQ ID NO:23. The antisense oligonucleotide (ASO) may have the sequence of SEQ ID NO:46. The antisense oligonucleotide (ASO) may have the sequence of SEQ ID NO:47. The antisense oligonucleotide (ASO) may have the sequence of SEQ ID NO:48. The antisense oligonucleotide (ASO) may have the sequence of SEQ ID NO:49.

The ASO may further include a modified internucleoside linkage. The modified internucleoside linkage may be a peptide-nucleic acid linkage, a morpholino linkage, a N3' to P5' phosphoramidate linkage, a methylphosphonate linkage or a phosphorothioate linkage. The modified internucleoside linkage may be a peptide-nucleic acid linkage. The modified internucleoside linkage may be a morpholino linkage. The modified internucleoside linkage may be a N3' to P5' phosphoramidate linkage. The modified internucleoside linkage may be a methylphosphonate linkage. The modified internucleoside linkage may be a phosphorothioate linkage. The ASO may further include a modified sugar moiety. The modified sugar moiety may be 2'-O-alkyl oligoribonucleotide. The ASO may have a 2'MOE gapmer modification. The ASO may further include a modified nucleobase. The modified nucleobase may be a 5-methyl pyrimidine or a 5-propynyl pyrimidine. The cell may be a human cell. The cancer may be characterized by elevated expression of MCT4. The cancer may be selected from one or more of the following: prostate cancer; renal cell carcinoma; breast cancer; cervical cancer; liver cancer; bladder cancer; and small cell lung cancer. The cancer may be selected from one or more of the following: prostate cancer; renal cell carcinoma; breast cancer; cervical cancer; liver cancer; and bladder cancer. The cancer may be selected from one or more of the following: prostate cancer; renal cell carcinoma; breast cancer; cervical cancer; and liver cancer. The cancer may be selected from one or more of the following: prostate cancer; renal cell carcinoma; breast cancer; and cervical cancer. The cancer may be selected from one or more of the following: prostate cancer; renal cell carcinoma; and breast cancer. The cancer may be selected from one or more of the following: prostate cancer; and renal cell carcinoma. The cancer may be selected from one or more of the following: prostate cancer; and small cell lung cancer. The cancer may be selected from one or more of the following: prostate cancer; renal cell carcinoma; breast cancer; cervical cancer; liver cancer; and small cell lung cancer. The cancer may be selected from one or more of the following: prostate cancer; renal cell carcinoma; breast cancer; cervical cancer; bladder cancer; and small cell lung cancer. The cancer may be selected from one or more of the following: prostate cancer; renal cell carcinoma; breast cancer; liver cancer; bladder cancer; and small cell lung cancer. The cancer may be selected from one or more of the following: prostate cancer; renal cell carcinoma; cervical cancer; liver cancer; bladder cancer; and small cell lung cancer. The cancer may be prostate cancer. The prostate cancer may be castration-resistant prostate cancer (CRPC). The cancer may be selected from one or more of the following: prostate cancer; renal cell carcinoma; breast cancer; liver cancer; and bladder cancer. The prostate cancer may be enzalutamide (ENZ) resistant CRPC. The cancer may be metastatic prostate cancer. The ASO may be substantially complementary to the mRNA of MCT4. The ASO may be administered intravenously. The ASO may be topically administered to a tissue. The ASO may be mixed with lipid particles prior to administration. The ASO may be encapsulated in liposomes prior to administration.

The ASO may further include a modified internucleoside linkage. The modified internucleoside linkage may be a peptide-nucleic acid linkage, a morpholino linkage, a N3' to P5' phosphoramidate linkage, a methylphosphonate linkage or a phosphorothioate linkage. The ASO may further include a modified sugar moiety. The modified sugar moiety may be a 2'-O-alkyl oligoribonucleotide. The ASO may further have a 2'MOE gapmer modification. The ASO may further include a modified nucleobase. The modified nucleobase may be a 5-methyl pyrimidine or a 5-propynyl pyrimidine.

The cell may be a human cell. The cancer may be characterized by elevated expression of MCT4. The cancer may be selected from one or more of the following: prostate cancer; renal cell carcinoma; breast cancer; cervical cancer; liver cancer; bladder cancer; and small cell lung cancer. The prostate cancer may be castration-resistant prostate cancer (CRPC). The prostate cancer may be enzalutamide (ENZ) resistant CRPC or metastatic CRPC (m CRPC).

The ASO may be substantially complementary to the mRNA of MCT4. The ASO may be administered intravenously. The ASO may be topically administered to a tissue. The ASO may be mixed with lipid particles prior to administration. The ASO may be encapsulated in liposomes prior to administration. Antisense oligonucleotides and may be used as neoadjuvant (prior), adjunctive (during), and/or adjuvant (after) therapy with surgery, radiation (brachytherapy or external beam), or other therapies (eg. HIFU). For example, MCT4 antisense oligonucleotides may be used in combination with docetaxel, MDV3100, or with modulators of glucose metabolism (including doxycycline or other mitochondrial inhibitors).

BRIEF DESCRIPTION OF THE DRAWINGS

FIG. 1C) shows plot of wherein high MCT4 expression is associated with earlier time to relapse as measured by increases in serum PSA; and FIG. 1D) and FIG. 1E) show two bar graphs representing patients undergoing prolonged neoadjuvant hormone therapy (NHT) and those with CRPC also show elevated MCT4 expression.

FIG. 2A) shows siRNA-silencing of MCT4 in PC-3 cells showed significant inhibition of cell proliferation, indicating that inhibition of MCT4 expression could have potential therapeutic efficacy; FIG. 2B) shows screening of ten MCT4-targeting ASOs revealed varying inhibitory effects on cell proliferation, with sequences #1 (SEQ ID NO: 1) and #14 (SEQ ID NO: 5) showing the most profound inhibitions; FIG. 2C) shows MCT4 ASOs inducing various levels of MCT4 knockdown as measured by qPCR and Western blot, with ASOs #1 and #14 being the most effective; FIG. 2D) shows a strong correlation (p<0.001) was found between the MCT4 mRNA expression and the resulting cell numbers, indicating that the inhibitory effects on cell proliferation are strongly related to decreased MCT4 expression (dotted lines represent the 95% confidence interval); FIG. 2E) wherein transfection of 5 nM to 200 nM of MCT4 ASOs shows that the inhibition of cell proliferation and expression of MCT4 is similarly dose dependent ($IC_{50}$=32 nM for ASO #14, $IC_{50}$=50 nM for ASO #1); and FIG. 2F) shows a time course experiment demonstrates that the inhibition of cell proliferation and MCT4 expression following MCT4 ASO transfections persists up to at least 96 hours post-transfection.

FIG. 3A) shows candidate MCT4 ASOs are also able to inhibit C4-2 human prostate cancer cell proliferation and expression of MCT4 in a dose-dependent manner with $IC_{50}$ values comparable to those observed with PC-3 cells; FIG. 3B) shows candidate MCT4 ASOs also inhibit DU145 human prostate cancer cell proliferation in a dose-dependent manner with $IC_{50}$ values similar to those obtained with the other cell lines, wherein the inhibition of cell proliferation is accompanied by a decrease in MCT4 expression; and FIG. 3C) shows that candidate MCT4 ASOs do not have any appreciable effects on TRAMPC2 mouse prostate cancer cells and they neither affect cell proliferation nor mouse MCT4 expression levels even at the highest tested concentration of 200 nM, showing that the tested ASOs are specific for human MCT4 and that the inhibition of cell proliferation is a phenomenon related to MCT4 knock-down.

FIG. 4A) shows that MCT4 ASOs significantly inhibited lactic acid secretion and that corresponding accumulation of intracellular lactate and inhibition of glucose consumption is also observed (u.d.=undetectable) 48 hours post-transfection; and FIG. 4B) shows a schematic of the glycolysis pathway and the changes in metabolism caused by MCT4 knock-down and characterized by qPCR analysis of gene expression levels of various genes involved in glycolysis and lactic acid conversion, wherein a significant decrease in expression of various genes in glycolysis suggests an overall decrease in glucose metabolism and the decreased expression of LDHA and PDK1 suggest a redirection of pyruvate away from lactic acid production toward the TCA cycle for oxidative phosphorylation.

FIG. 5A) shows a plot representing percent tumour volume by treatment day comparing MCT4 ASOs in relation to the rate of tumour growth; FIG. 5B) shows bar graphs representing caspase 3 positive cells and percent Ki-67 positive cells following treatment with MCT4 ASOs as attributable to an increase in cell apoptosis and a decrease in cell proliferation; and FIG. 5C) shows treatment with MCT4 ASOs decreased MCT4 expression in the tumour as measured by IHC staining.

FIG. 6A) shows a bar graph wherein the immunomodulatory effects of treatment with MCT4 ASO are partially exerted through a significant increase in the extent of such immune cell aggregations; FIG. 6B) shows a bar graph wherein the treatment with MCT4 ASO increased the proportion of NK cells associated with the tumour; and FIG. 6C) shows a bar graph representing the proportion of CD3 positive cells as a marker for activated NK cells (since nude mice lack T cells) in the presence of MCT4 ASOs as compared to control.

FIG. 7A) shows MCT4 ASOs are able to inhibit LNCaP cell proliferation to levels comparable to those observed with other human prostate cancer cell lines; and FIG. 7B) shows that a decrease in cell proliferation is associated with a decrease in MCT4 expression, which suggests that the inhibitory effect of MCT4 ASOs may be more associated with a glycolytic phenotype than with androgen receptor status.

FIG. 8A) shows treatment of PC3 cells with candidate MCT4 ASOs resulted in an inhibition of cell migration through a transwell, as indicated by a reduction in the number of migrated cells observed; and FIG. 8B) shows that the treatment with MCT4 ASO also inhibited the ability of PC-3 cells to invade Matrigel, and suggests that MCT4-mediated lactic acid secretion could play an important role in cancer metastasis.

FIG. 9A) shows a plot of animal weights throughout the duration of the in vivo study, and treatment with MCT4 ASOs did not significantly affect the average animal weight of each group; and FIG. 9B) shows that the individual animal weights also remained stable throughout the treatment period.

FIG. 10(A) shows the total live PC3 cell numbers for SEQ ID NO:5 ASO and Metformin; FIG. 10(B) shows the total live PC3 cell numbers for SEQ ID NO:5 ASO and Doxycycline; FIG. 10(C) shows the total live PC3 cell numbers for SEQ ID NO:5 ASO and Docetaxel; and FIG. 10(D) shows the total live C4-2 cell numbers for SEQ ID NO:5 ASO and MDV3100.

DETAILED DESCRIPTION

Figure 1A:
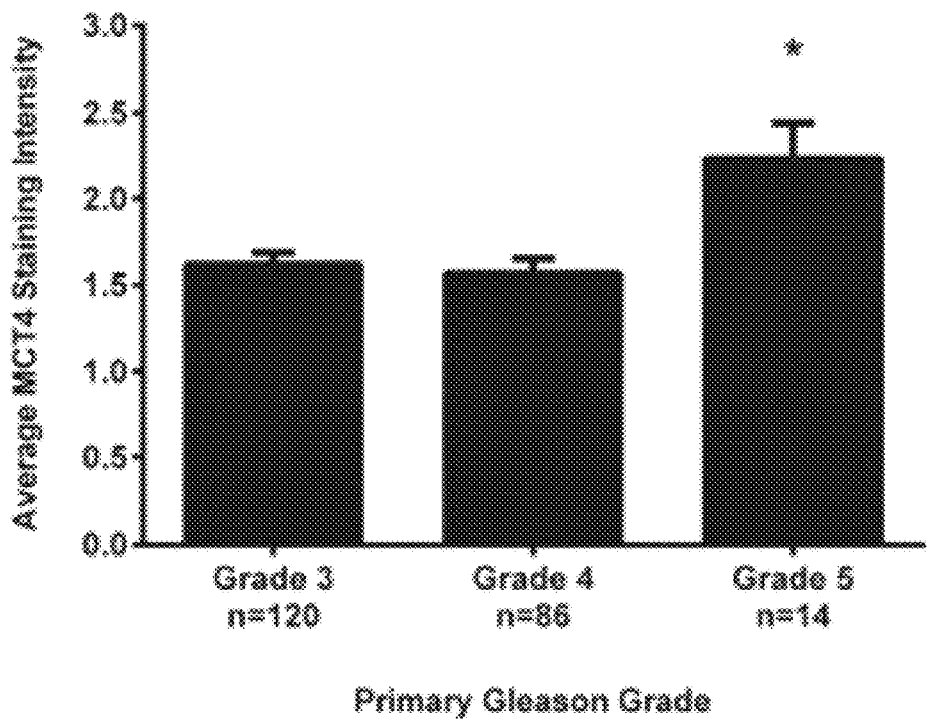
FIGS. 1A-1E shows MCT4 expression in tissue microarrays (TMA) from patient-derived prostate cancer samples available at the Vancouver Prostate Centre Tissue Bank and stained for MCT4 expression, wherein FIG. 1A) and FIG. 1B) show bar graphs confirming that elevated MCT4 expression is associated with high Gleason grade.
Figure 1B:
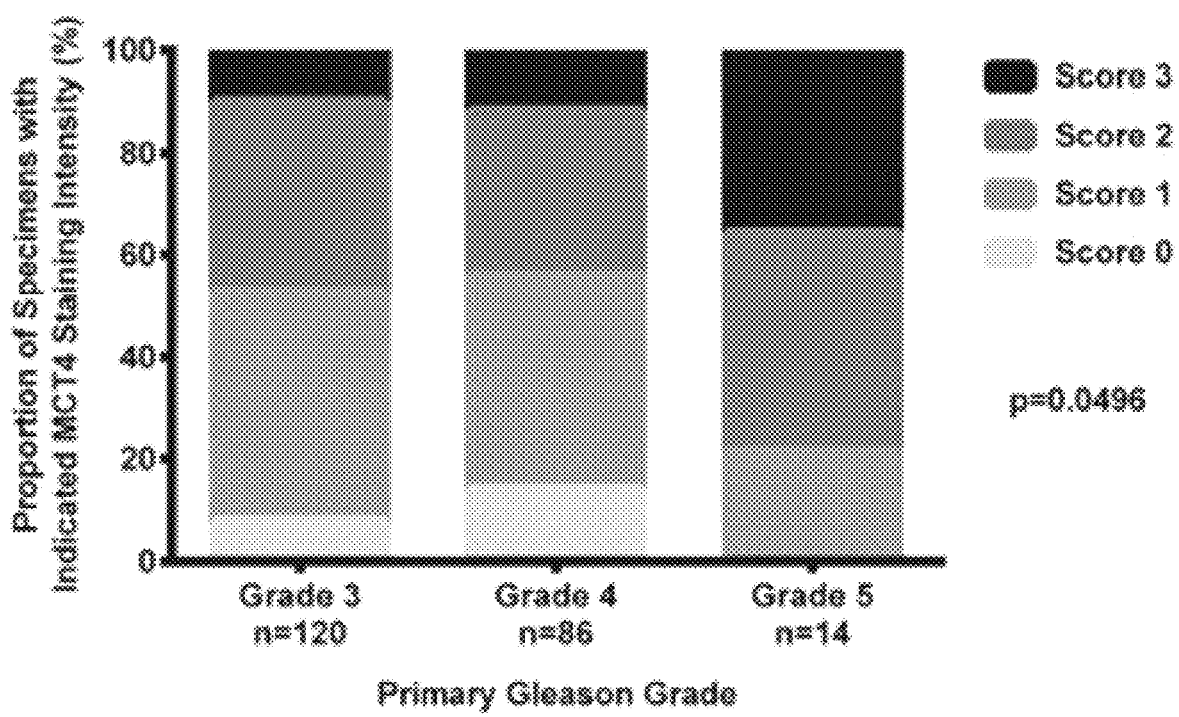

Any terms not directly defined herein shall be understood to have the meanings commonly associated with them as understood within the present field of art. Certain terms are discussed below, or elsewhere in the specification, to provide additional guidance to the practitioner in describing the compositions, devices, methods and the like of embodiments, and how to make or use them. It will be appreciated that the same thing may be said in more than one way. Consequently, alternative language and synonyms may be used for any one or more of the terms discussed herein. No significance is to be placed upon whether or not a term is elaborated or discussed herein. Some synonyms or substitutable methods, materials and the like are provided. Recital of one or a few synonyms or equivalents does not exclude use of other synonyms or equivalents, unless it is explicitly stated. Use of examples in the specification, including examples of terms, is for illustrative purposes only and does not limit the scope and meaning of the embodiments described herein.

A method is provided for "treating" a cancer cell, wherein treating is meant to encompass preventing proliferation of the cell, ameliorating symptoms associated with the cancer, and eradicating the cancer cell. The term "treating" as used herein is also meant to include the administration at any stage of the cancer, including early administration of a compound or late administration. A person of skill in the art would appreciate that the term "ameliorating" is meant to include the prospect of making a cancer more tolerable for a subject afflicted therewith (for example, by reducing tumour load). A person of skill in the art would also appreciate that the term "eradication" with regards to cancer would include elimination of the cancer cells in whole or in part from a subject. Accordingly, as used herein "treatment" may refer to the prevention of cancer cell proliferation in a subject, the amelioration of symptoms associated with the cancer, the eradication of the cancer from a subject, or combinations thereof.

Antisense oligonucleotide compounds are typically single stranded RNA compounds which bind to complementary RNA compounds, such as target mRNA molecules, and block translation from the complementary RNA compounds by sterically interfering with the normal translational machinery. This process is usually passive, in that it does not require or involve additional enzymes to mediate the RNA interference process. Specific targeting of antisense RNA compounds to inhibit the expression of a desired gene may generally involve designing the antisense RNA compound to have a homologous, complementary sequence to the desired gene. Perfect homology is not necessary for the RNA interference effect. In one embodiment of the invention, the antisense RNA compounds include any RNA compound with sufficient complementary homology to bind to the MCT4 mRNA transcript causing a reduction in translation of the MCT4 protein. In another embodiment of the invention, the antisense RNA compounds include any RNA compound with sufficient complementary homology to bind to the MCT4 mRNA transcript causing a reduction in translation of the MCT4 protein. The antisense compounds may be modified to enhance the stability of the oligonucleotides, particularly for in vivo use. Numerous examples of methods for designing and optimizing antisense RNA compounds are found in the journal literature (i.e. Pan and Clawson 2006; Patzel 2007; Peek and Behlke 2007). Perfect sequence complementarity is not necessary for the antisense compound to modulate expression of the target gene. The present inventors provide non-limiting examples of antisense compounds which modulate the expression of MCT4.

Antisense oligonucleotide sequences as described herein (see TABLES A and B) or for use as described herein may be administered by means of a medical device or appliance such as an implant, graft, prosthesis, stent, etc. Also, implants may be devised which are intended to contain and release such compounds or compositions. An example would be an implant made of a polymeric material adapted to release the compound over a period of time.

The percent inhibition for all tested MCT4 ASOs is shown below in TABLE A. Generally a 50% inhibition was considered active for MCT4 ASOs.

TABLE A

MCT4 ASO Sequences and Percent Inhibition of MCT4.

| SEQ ID No. | Sequence (5' to 3') | Nucleotide Range | % MCT4 Inhibition | Previous Identif. |
|---|---|---|---|---|
| 1 | TCCCATGGCCAGGAGGGTTG | 137-156 | 65.52 | MCT4 ASO #1 |
| 2 | GTCCCGGAAGACGCTCAGGT | 806-825 | 86.33 | MCT4 ASO #3 |
| 3 | AAGGACGCAGCCACCATGCC | 451-470 | 71.19 | MCT4 ASO #12 |
| 4 | TTGGCGTAGCTCACCACGAA | 892-911 | 77.13 | MCT4 ASO #13 |
| 5 | AGATGCAGAAGACCACGAGG | 1110-1129 | 78.16 | MCT4 ASO #14 |
| 6 | CCACTCTGGAATGACACGGT | 1719-1738 | 78.67 | MCT4 ASO #20 |
| 7 | GTAGGAGAAGCCAGTGATGAC | 238-257 | 66.31 | MCT4 ASO #21 |
| 8 | AGCATGGCCAGCAGGATGGA | 343-362 | 80.77 | MCT4 ASO #22 |
| 9 | GGCTGGAAGTTGAGTGCCAA | 526-545 | 76.03 | MCT4 ASO #23 |
| 10 | CATGCCGTAGGAGATGCCAA | 1133-1152 | 76.51 | MCT4 ASO #24 |
| 11 | CTCAGGCTGTGGCTCTTTGG | 1391-1410 | 63.01 | MCT4 ASO #27 |
| 12 | TAGCGGTTCAGCATGATGA | 551-569 | 70.36 | MCT4 siRNA ASO #3 |
| 13 | AGCACGGCCCAGCCCCAGCC | 205-224 | 66.85 | MCT4 +1 ASO #1 |
| 14 | GAGCTCCTTGAAGAAGACACT | 277-296 | 72.00 | MCT4 +1 ASO #2 |
| 15 | CAGGATGGAGGAGATCCAGG | 332-351 | 75.58 | MCT4 +1 ASO #3 |
| 16 | AGACCCCCACAAGCATGAC | 418-437 | 55.47 | MCT4 +1 ASO #4 |

TABLE A-continued

MCT4 ASO Sequences and Percent Inhibition of MCT4.

| SEQ ID No. | Sequence (5' to 3') | Nucleotide Range | % MCT4 Inhibition | Previous Identif. |
|---|---|---|---|---|
| 17 | GAAGTTGAGTGCCAAACCCAA | 520-539 | 70.93 | MCT4 +1 ASO #5 |
| 18 | CCCGTTGGCCATGGGGCGCC | 581-600 | 71.14 | MCT4 +1 ASO #6 |
| 19 | GCCAGCCCGTTGGCCATGGG | 586-605 | 80.26 | MCT4 +1 ASO #7 |
| 20 | AGGAAGACAGGGCTACCTGC | 610-629 | 66.26 | MCT4 +1 ASO #8 |
| 21 | GCACACAGGAAGACAGGGCT | 616-635 | 60.36 | MCT4 +1 ASO #9 |
| 22 | CAGGGCACACAGGAAGACAG | 620-639 | 79.96 | MCT4 +1 ASO #10 |
| 23 | CAGCAGTTGAGCAGCAGGCC | 703-722 | 65.41 | MCT4 +1 ASO #11 |
| 24 | GACCTGTCCCGTAGAGCATG | 357-396 | 47.24 | MCT4 ASO #2 |
| 25 | TTCCCAAGCCCCGCCACGAA | 997-1016 | 22.88 | MCT4 ASO #4 |
| 26 | AATGCTCCACCTCCCGCAAG | 1467-1486 | 9.55 | MCT4 ASO #5 |
| 27 | ACCTCCCCGTTTTTCTCAGG | 1501-1520 | 3.17 | MCT4 ASO #6 |
| 28 | TGTGAACCACCTCCCCGTTT | 1509-1528 | 29.91 | MCT4 ASO #7 |
| 29 | TCTGTACCTCCTCCCTGTGC | 1570-1589 | 16.31 | MCT4 ASO #8 |
| 30 | GAATGACACGGTTCCCACCC | 1711-1730 | 25.51 | MCT4 ASO #9 |
| 31 | GCCCACCCACCCTCCCATTA | 1870-1889 | -43.4 | MCT4 ASO #10 |
| 32 | AAGAGACCCCCCACAAGCAT | 421-440 | 18.67 | MCT4 ASO #11 |
| 33 | CCCACCATGCCGTAGGAGAT | 1138-1157 | 49.00 | MCT4 ASO #15 |
| 34 | AGTCCACCCCCGAGTCTGCA | 1449-1468 | 20.5 | MCT4 ASO #16 |
| 35 | CTTCACCGCAGATCCACTCT | 1732-1751 | -10.07 | MCT4 ASO #17 |
| 36 | AACACTCCACCCACACGCAG | 2028-2047 | 9.33 | MCT4 ASO #18 |
| 37 | CCAGCCACTCAGACACTTGT | 1537-1556 | 33.14 | MCT4 ASO #19 |
| 38 | GGCCACCGCCTCCATCAGCA | 1229-1248 | 45.92 | MCT4 ASO #25 |
| 39 | CCTGAGCCAGTCCAGTTTGT | 1616-1635 | 39.46 | MCT4 ASO #26 |
| 40 | CCCACCCACCCTCCCATTAA | 1869-1888 | -42.05 | MCT4 ASO #28 |
| 41 | GCTTCTGTACCTCCTCCCTG | 1573-1592 | 17.02 | MCT4 ASO #29 |
| 42 | TGTCGCTGTAGCCGATCCC | 310-328 | 21.20 | MCT4 siRNA ASO #1 |
| 43 | TTAAAGTCACGTTGTCTCG | 1854-1872 | 0.27 | MCT4 siRNA ASO #2 |
| 44 | TTGCGGCTTGGCTTCACCG | 1744-1762 | 31.16 | MCT4 siRNA ASO #4 |
| 45 | CACAGCTCCTCCCATGGCCAGG | | 22.4 | Suzuki Rat MCT4 ASO |
| 46 | ATGGCCAGGAGGGTTG | 137-152 | 76.03 | MCT4 ASO #1.1 |
| 47 | CATGGCCAGGAGGGTT | 138-153 | 81.21 | MCT4 ASO #1.2 |

TABLE A-continued

MCT4 ASO Sequences and Percent Inhibition of MCT4.

| SEQ ID No. | Sequence (5' to 3') | Nucleotide Range | % MCT4 Inhibition | Previous Identif. |
|---|---|---|---|---|
| 48 | CCATGGCCAGGAGGGT | 139-154 | 77.65 | MCT4 ASO #1.3 |
| 49 | CCCATGGCCAGGAGGG | 140-155 | 65.76 | MCT4 ASO #1.4 |
| 50 | TCCCATGGCCAGGAGG | 141-156 | 30.52 | MCT4 ASO #1.5 |
| 51 | CCTTCCCTGAAGGTTCCTCC | | 0.00 | Control ASO |

Antisense oligonucleotides (ASOs) that target MCT4 are provided herein. The use of MCT4 ASOs for administration to a cell is encompassed by the methods described herein. Some of the ASOs as used in the Examples section had modified internucleoside linkages. In particular, the ASOs had phosphorothioate linkages between all nucleosides. MCT4 ASOs are 16 to 20-mer oligonucleotides with modified phosphorothioate linkages. However, variations of MCT4 ASOs may also have unmodified phosphodiester linkages or partially modified linkages (i.e. any integer between 1 and 19 phosphorothioate linkage(s) or other modified linkages). Alternative modifications are also known in the art.

Antisense oligonucleotides (ASOs) of 16 to 20-mer in length that target MCT4 are provided herein. However, it would be apparent to a person skilled in the art that biologically active oligonucleotide comprising the 16, 19 or 20 nucleotides of SEQ ID NO: 1-23 or SEQ ID NO. 46-49 may also be used.

A phosphorothioate oligonucleotide bond modification alters the phosphate linkage by replacing one of the non-bridging oxygens with sulfur. The introduction of phosphorothioate linkages alters the chemical properties of the oligonucleotide. In particular, the addition of phosphorothioate linkages reduces nuclease degradation of the oligonucleotide and thereby increasing the half-life in situ. Accordingly, this modification is particularly useful for antisense oligonucleotides, which when introduced into cells or biological matrices can interact with target nucleic acids to silence the expression of a particular transcript. Oligonucleotides containing phosphorothioate linkages accomplish this feat either through direct blockage of translation or enable enzymatic degradation of the target transcript (for example, via RNase H).

Although phosphorothioate linkages provide improved half-life, the introduction of these linkages into an oligonucleotide may also introduce limitations to their function as antisense oligonucleotides. Each phosphorothioate linkage creates a chiral center at each bond, which may result in multiple isomers of the oligonucleotide generated during synthesis and the isomers may have differential characteristics and functional properties. However much of the isomer effects may be mitigated through careful positioning of the modifications or by using additional modifications in conjunction with the phosphorothioate bonds.

One or more of the phosphorothiodiester linkages of the oligonucleotide moiety may be modified by replacing one or both of the two bridging oxygen atoms of the linkage with analogues such as —NH, —CH2, or —S. Other oxygen analogues known in the art may also be used.

A "modified oligonucleotide" as used herein is meant to include oligonucleotides that are substituted or modified. In addition to the naturally occurring primary bases adenine, guanine, cytosine, and thymine, or other natural bases such as inosine, deoxyinosine, and hypoxanthine, there are numerous other modifications. For example, isosteric purine 2' deoxy-furanoside analogues, 2'-deoxynebularine or 2' deoxyxanthosine, or other purine and pyrimidine analogues such as 5-methyl pyrimidine or a 5-propynyl pyrimidine may also be utilized to improve stability and target hybridization.

A "modified sugar" as used herein when discussing an oligonucleotide moiety, a sugar modified or replaced so as to be ribose, glucose, sucrose, or galactose, or any other sugar. Alternatively, the oligonucleotide may have one or more of its sugars substituted or modified in its 2' position, i.e. 2' alkyl or 2'-O-alkyl. An example of a 2'-O-allyl sugar is a 2'-O-methylribonucleotide. Furthermore, the oligonucleotide may have one or more of its sugars substituted or modified to form an α-anomeric sugar.

"Second-generation" oligonucleotides as used herein mat be defined as oligonucleotides that are resistant to degradation by cellular nucleases and capable of hybridizing specifically to their target mRNA with equal or higher affinity than first generation ASOs. An example of a $2^{nd}$ generation ASO is a 2'-O-(2-Methoxyethyl)-RNA (2'MOE gapmer modification). With a 2'-MOE gapmer the 5' and 3' ends may have 2'-MOE modified nucleotides to protect against degradation, but the gap between the 5' and 3' ends may be unmodified phosphodiester linkages. Numerous other chemical modifications have been developed to improve ASOs. For example, morpholino, N3' to P5' phosphoramidate, and methylphosphonate chemical modifications are known in the art (N. Dias, and C. A. Stein 2002). Furthermore, peptide nucleic acids (PNAs) may also be used.

An alignment of tested 16 mer truncations of SEQ ID NO:1 are shown in TABLE B along with their % MCT4 inhibitions,

TABLE B

Alignment of SEQ ID NO 1 with 16 mer Truncations

| SEQ ID NO | SEQUENCE | % MCT4 Inhibition |
|---|---|---|
| 1 | TCCCATGGCCAGGAGGGTTG | 65.52 |
| 46 | ATGGCCAGGAGGGTTG | 76.03 |
| 47 | CATGGCCAGGAGGGTT | 81.21 |
| 48 | CCATGGCCAGGAGGGT | 77.65 |

TABLE B-continued

Alignment of SEQ ID NO 1 with 16 mer Truncations

| SEQ ID NO | SEQUENCE | % MCT4 Inhibition |
|---|---|---|
| 49 | CCCATGGCCAGGAGGG | 65.76 |
| 50 | TCCCATGGCCAGGAGG | 30.52 |

The compounds, as described herein, may be in isolation, or may be linked to or in combination with tracer compounds, liposomes, carbohydrate carriers, polymeric carriers or other agents or excipients as will be apparent to one of skill in the art. In alternate embodiments, such compounds may further comprise an additional medicament, wherein such compounds may be present in a pharmacologically effective amount.

The term "medicament" as used herein refers to a composition that may be administered to a patient or test subject and is capable of producing an effect in the patient or test subject. The effect may be chemical, biological or physical, and the patient or test subject may be human, or a non-human animal, such as a rodent (for example, a transgenic mouse, a mouse or a rat), dog, cat, cow, sheep, horse, hamster, guinea pig, rabbit or pig. The medicament may be comprised of the effective chemical entity alone or in combination with a pharmaceutically acceptable excipient.

The term "pharmaceutically acceptable excipient" may include any and all solvents, dispersion media, coatings, antibacterial, antimicrobial or antifungal agents, isotonic and absorption delaying agents, and the like that are physiologically compatible. An excipient may be suitable for intravenous, intraperitoneal, intramuscular, subcutaneous, intrathecal, topical or oral administration. An excipient may include sterile aqueous solutions or dispersions for extemporaneous preparation of sterile injectable solutions or dispersion. Use of such media for preparation of medicaments is known in the art.

Compositions or compounds according to some embodiments described herein may be administered in any of a variety of known routes. Examples of methods that may be suitable for the administration of a compound include orally, intravenous, inhalation, intramuscular, subcutaneous, topical, intraperitoneal, intra-rectal or intra-vaginal suppository, sublingual, and the like. The compounds described herein may be administered as a sterile aqueous solution, or may be administered in a fat-soluble excipient, or in another solution, suspension, patch, tablet or paste format as is appropriate. A composition comprising the compounds described herein may be formulated for administration by inhalation. For instance, a compound may be combined with an excipient to allow dispersion in an aerosol. Examples of inhalation formulations will be known to those skilled in the art. Other agents may be included in combination with the compounds described herein to aid uptake or metabolism, or delay dispersion within the host, such as in a controlled-release formulation. Examples of controlled release formulations will be known to those of skill in the art, and may include microencapsulation, embolism within a carbohydrate or polymer matrix, and the like. Other methods known in the art for making formulations are found in, for example, "Remington's Pharmaceutical Sciences", (19th edition), ed. A. Gennaro, 1995, Mack Publishing Company, Easton, Pa.

The dosage of the compositions or compounds of some embodiments described herein may vary depending on the route of administration (oral, intravenous, inhalation, or the like) and the form in which the composition or compound is administered (solution, controlled release or the like). Determination of appropriate dosages is within the ability of one of skill in the art. As used herein, an "effective amount", a "therapeutically effective amount", or a "pharmacologically effective amount" of a compound refers to an amount of an ASO as described herein present in such a concentration to result in a therapeutic level of the compound delivered over the term that the compound is used. This may be dependent on the mode of delivery, time period of the dosage, age, weight, general health, sex and diet of the subject receiving the compound. Methods of determining effective amounts are known in the art. It is understood that it could be potentially beneficial to restrict delivery of the compounds described herein to the target tissue or cell in which inhibition of MCT4 expression is desired. It is also understood that it may be desirable to target the compounds described herein to a desired tissue or cell type. The compounds described herein may thus be coupled to a targeting moiety. The compounds may be coupled to a cell uptake moiety. The targeting moiety may also function as the cell uptake moiety.

In general, antisense oligonucleotides as described herein may be used without causing substantial toxicity. Toxicity of the compounds as described herein can be determined using standard techniques, for example, by testing in cell cultures or experimental animals and determining the therapeutic index, i.e., the ratio between the LD50 (the dose lethal to 50% of the population) and the LD100 (the dose lethal to 100% of the population). In some circumstances however, such as in severe disease conditions, it may be appropriate to administer substantial excesses of the compositions. Some antisense oligonucleotides as described herein may be toxic at some concentrations. Titration studies may be used to determine toxic and non toxic concentrations. Toxicity may be evaluated by examining a particular antisense oligonucleotide's specificity across cell lines. Animal studies may be used to provide an indication if the compound has any effects on other tissues.

In some embodiments, at least one antisense oligonucleotide as described herein may be used, for example, and without limitation, for treating a cancer cell. As used herein "at least one" is intended to mean one or more, i.e. 1, 2, 3, 4, 5, 6, 7, 8, 9, 10, 11, 12, 13, 14, 15, 16, 17, 18, 19, 20, 21, 22, 23, 24, 25, 26, 27 etc.

In some embodiments, antisense oligonucleotides as described herein may be used, for example, and without limitation, in combination with other treatment methods for at least one indication selected from malignancies in which elevated expression of MCT4 is observed. These include, but are not limited to, prostate cancer; renal cell carcinoma; breast cancer; cervical cancer; liver cancer; bladder cancer; and small cell lung cancer in mammals, including humans. Antisense oligonucleotides and may be used as neoadjuvant (prior), adjunctive (during), and/or adjuvant (after) therapy with surgery, radiation (brachytherapy or external beam), or other therapies (for example, HIFU). For example, MCT4 antisense oligonucleotides as described herein may be used in combination with docetaxel, MDV3100, or with modulators of glucose metabolism (including doxycycline or other mitochondrial inhibitors).

Methods and Materials

The following methods and materials were employed with respect to the EXAMPLES described herein.

Cell Cultures

Human PC-3 and DU145 CRPC cells, human LNCaP prostate cancer cells, and mouse TRAMPC2 prostate cancer cells were purchased from the American Type Culture Collection (ATCC); C4-2 CRPC cells were from the Vancouver Prostate Centre, Vancouver, BC, Canada. Human monolayer cultures were maintained in RPMI-1640 (GE Healthcare Hyclone™, Logan, Utah) supplemented with 10% fetal bovine serum (FBS) (GE Healthcare Hyclone™, Logan, Utah) while TRAMPC2 cells were maintained in DMEM (GE Healthcare Hyclone™, Logan, Utah) supplemented with 5% FBS. For cell counting, cells were trypsinized to form a single cell suspension and counted using a TC20 Automated Cell Counter (Bio-Rad, Hercules, Calif.). Cell viability was assessed by trypan blue exclusion.

Human Prostate Cancer Tissue Microarray (TMA) Construction and Immunohistochemistry TMAs were manually constructed, as previously described (Chiang et al., 2014; Thomas et al., 2011), using various Gleason grades-exhibiting prostate cancer specimens (n=342), obtained from the Vancouver Prostate Centre Tissue Bank with written informed patients' consent, clinical information and institutional study approval. All specimens were obtained through radical prostatectomy, except CRPC samples that were obtained via transurethral resection of the prostate (TURP). Immunohistochemical staining was conducted using a Ventana™ autostainer (model Discover XT™; Ventana Medical System™, Tucson, Ariz.) with an enzyme-labelled biotin-streptavidin system and a solvent-resistant DAB Map kit (Ventana™). Staining intensity was scored by a trained pathologist on a four-point scale: 0 represents no staining on any tumor cells, 1 represents a faint or focal, questionably present stain, 2 represents a stain of convincing intensity in a minority of cells, and 3 represents a stain of convincing intensity in a majority of cells.

Antibodies

The following antibodies and conjugates were used: rabbit anti-MCT4 antibody (Santa Cruz™, Santa Cruz, Calif.; WB 1:4000, IHC 1:100), mouse anti-vinculin antibody (Sigma™; WB 1:1000), rabbit anti-cleaved caspase 3 antibody (Cell Signalling Technology™, Danvers, Mass.; IHC 1:50), mouse anti-Ki67 antibody (Dako™, Burlington, ON; IHC 1:50), rat anti-CD31 antibody (Dianova™, Hamburg, Germany; IHC 1:20), mouse anti-pan-T cell marker CD3 antibody (Dako™; IHC 1:50), biotinylated mouse anti-NK1.1 (Cedarlane™, Burlington, ON; IHC 1:100), IRDye 800CW goat anti-mouse antibody (Li-Cor Biosciences™, Lincoln, Nebr.; WB 1:10,000), IRDye 680RD goat anti-rabbit antibody (Li-Cor Biosciences™; WB 1:10,000), biotinylated goat anti-rabbit antibody (Vector Laboratories™, Burlingame, Calif.; IHC 1:200), biotinylated goat anti-rat antibody (Vector Laboratories™; IHC 1:200), and biotinylated goat anti-mouse antibody (Vector Laboratories™; IHC 1:200).

ASO Design and Selection

First-generation phosphorothioate-modified ASOs against human MCT4 were rationally designed by selecting sequences containing favourable motifs while excluding unfavourable ones (Matveeva et al., 2000). Specificity of MCT4-targeting sequences, compared to human and mouse genes (at least 3 of 20 bases mismatched), was evaluated using BLAST. Ten sequences SEQ ID No: 1, 4, 5, 9, 11, 30, 36, 37, 40 and 41 (see TABLE A) distributed throughout the length of the transcript with perfect complementarity to all human MCT4 transcript variants (NM_001042422.2, NM_001042423.2, NM_001206950.1, NM_001206951.1, NM_001206952.1, and NM_004207.3) were selected and synthesized by Eurofins MWG Operon. The knock-down efficiencies of these ten ASOs were tested by determining target mRNA and protein expression 48 hours after transfection of cells using qPCR and Western blotting. Two candidate ASOs (#1 and #14—SEQ ID NOs: 1 and 5, respectively) were selected for further studies. Sequences: ASO #1 (SEQ ID NO: 1), 5'-TCCCATGGCCAG-GAGGGTIG-3'; ASO #14 (SEQ ID NO: 5), 5'-AG-ATGCAGAAGACCACGAGG-3'; a published non-targeting control ASO, 5'-CCTTCCCTGAAGGTTCCTCC-3' (Mullick et al., 2011; Samuel et al., 2006).

A person of skill in the art based on the general knowledge in the art and the information provided herein would be able to synthesize the ASOs described herein or modify the ASOs described herein.

ASO and siRNA Transfection

Cells were transfected in 6-well plates with ASOs at 100 nM for 48 hours (unless otherwise indicated) using Oligofectamine™ (Invitrogen™, Carlsbad, Calif.) or with MCT4-targeting siRNAs and controls (Dharmacon™, Chicago, Ill.) at 50 nM for 48 hours using Lipofectamine™ 2000 (Invitrogen™), following the manufacturer's instructions.

Quantitative PCR

Total RNA was isolated using the RNeasy Mini Kit™ (Qiagen Inc.™, Hilden, Germany) and cDNA synthesized using the QuantiTect Reverse Transcription Kit™ (Qiagen™). Primers were designed using Primer-BLAST™. qRT-PCR reactions using KAPA SYBR Fast Universal™ (Kapa Biosystems™, Woburn, Mass.) were performed in triplicate in a ViiA 7 Real-Time PCR™ system (Applied Biosystems™, Foster City, Calif.). Target genes were normalized to a geometric average of 3 internal reference genes (Vandesompele et al., 2002).

Western Blotting

Cells were harvested and lysed in RIPA buffer (50 mM Tris-Cl pH 7.4, 150 mM NaCl, 1% Igepal, 0.5% Na-deoxycholate, 0.1% SDS) supplemented with a complete protease inhibitor cocktail (Roche, Nutley, N.J.). The protein concentration of the lysate was determined by Pierce BCA Protein Assay™ (Thermo Scientific™, Waltham, Mass.). The lysate was run on 8% SDS polyacrylamide gel (20 ug of protein per lane) and proteins were transferred onto PVDF membrane (Millipore™, Billerica, Mass.). The blot was blocked with the Odyssey™ blocking buffer (Li-cor Biosciences™) and probed with anti-MCT4 antibody. Vinculin was used as a loading control. Following overnight incubation at 4° C., the primary antibody was probed with the corresponding secondary antibody and detected using the Odyssey Infrared Imaging System™ (Li-cor Biosciences™) and Image Studio Version 3.1™ (Li-cor Biosciences™). Densitometry analysis was done using ImageJ (U.S. National Institutes of Health, Bethesda, Md.).

Modified Boyden Chamber Assay

The migration and invasion potential of PC-3 cells following treatment with MCT4 ASOs was investigated using Matrigel-coated modified Boyden chambers (BD Bioscience™, San Jose, Calif.) as previously described (Chiang et al., 2014). Briefly, ASO-treated cells were seeded into the top chamber at 50,000 live cells per well. The cells were then re-suspended after 48 hours using dissociation buffer (Trevigen™, Gaithersburg, Md.) containing calcein AMS (12.5 mM; Trevigen™). The number of migrated/invaded cells in the lower chamber was determined by fluorescence measurement (485 nm excitation, 520 nm emission) of the cell suspensions using the Infinite F500 Fluorometer™ (Tecan™, Männedorf, Switzerland).

Lactate and Glucose Determination

PC-3 cells transfected with ASOs for 48 hours were assessed for lactate and glucose levels. Cells were incubated with fresh media for 4 hours. A sample of the media was then taken and deproteinated with 10K Spin Columns™ (BioVision™, Milpitas, Calif.) prior to determination of lactate concentration using Lactate Assay Kit (BioVision) and glucose concentration using Glucose Assay Kit™ (BioVision™). Intracellular lactate levels were determined by lysing ASO-transfected cells in MQH2O. Final concentrations were determined by normalizing to the total number of live cells.

Treatment with MCT4 ASO of PC-3 Tumor-Bearing Nude Mice

PC-3 cells (106 cells in 1:1 HBSS:Matrigel) were injected subcutaneously into both flanks of 24 male athymic nude mice (Simonsen Laboratories™, Gilroy, Calif.). Once the mean tumour volume had reached approximately 100 mm3, mice were randomized into four groups and treated with intraperitoneal injections of MCT4 ASO #1 (SEQ ID NO: 1), #14 (SEQ ID NO: 5), control ASO, or vehicle (PBS) at 10 mg/kg daily for 5 days followed by 2 days off treatment for a total of 15 days. The health of the mice was monitored throughout the study by measuring body weights and checking for abnormal behaviour such as lethargy, lack of hydration, and additional signs of weakness. Tumour size was measured twice weekly and tumour volume calculated using the formula: Volume=Length×width×depth×0.5236 (mm3). Mice were sacrificed 1 hour after the final dose for tissue harvesting.

Immunohistochemistry of Tumour Tissue

Tumour tissue was formalin-fixed and paraffin-embedded for immunohistochemical analysis. Tissues were sectioned, probed, and stained with DAB (Sigma™) as previously described (Wang et al., 2005). For Ki-67 and cleaved caspase 3 staining, images of five random fields at 400× magnification were taken per tumour and cells counted to determine the percentage of positively stained cells. For MCT4, images of five random fields at 200× magnification were taken per tumour and staining intensity was assessed by percentage scoring, using the formula: Intensity=(% area score 3)×3+(% area score 2)×2+(% area score 1)×1. The extent of immune cell aggregation was quantified following CD31 staining by imaging the five most prominent regions of aggregates per tumour at 200× magnification and determining the percent area of the field they occupied. The proportions of immune cells were evaluated as the area of positive staining normalized to the area occupied by immune cell aggregates in the same five prominent regions.

Statistical Analysis

All pooled results are represented as Mean f SEM. Statistical analysis was performed using GraphPad Prism 6T™ (GraphPad Software, Inc., La Jolla, Calif.). The Student t-test was carried out to compare means between two groups. One-way ANOVA followed by the post-hoc Dunnett's test was used to compare means of more than two groups. Two-way ANOVA followed by post-hoc multiple comparison was applied to compare tumour growth. A contingency test was done to compare staining intensity between patient cohorts on the tissue microarray. A Log-rank test was done to compare patient survival curves. Chi-squared tests were done to correlate MCT4 expression levels with various clinical parameters. Results with a p-value <0.05 were considered statistically significant and are indicated by * for p<0.05,  for p<0.01, and * for p<0.001.

EXAMPLES

Example 1: Elevated MCT4 Protein Expression is Associated with CRPC

Figure 1C:
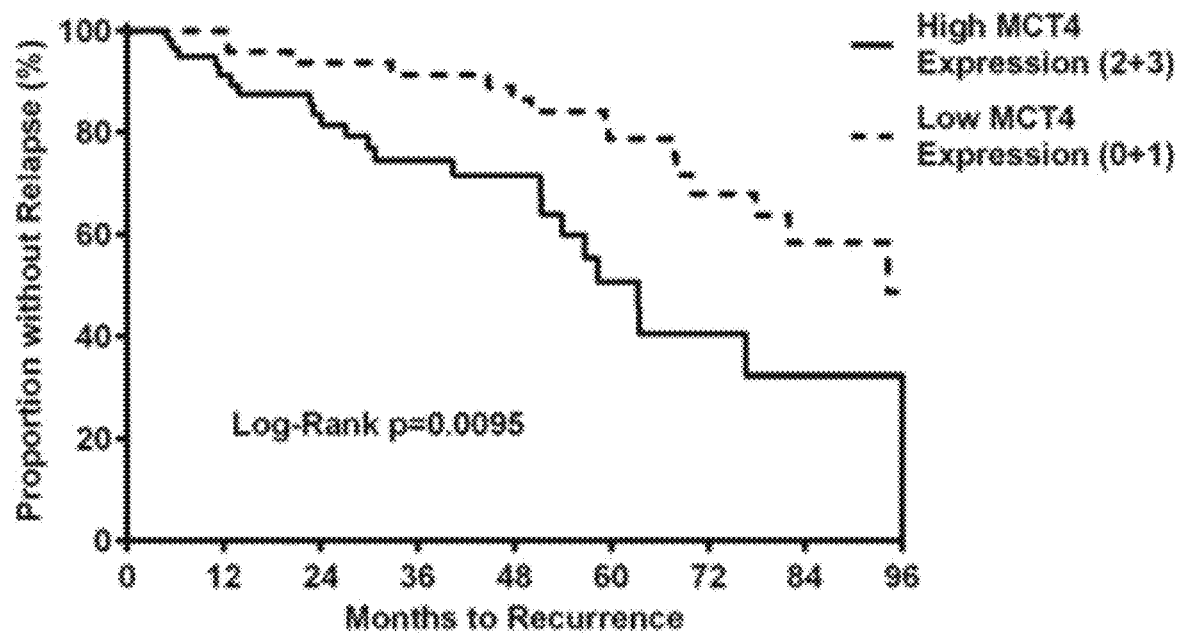
Figure 1D:
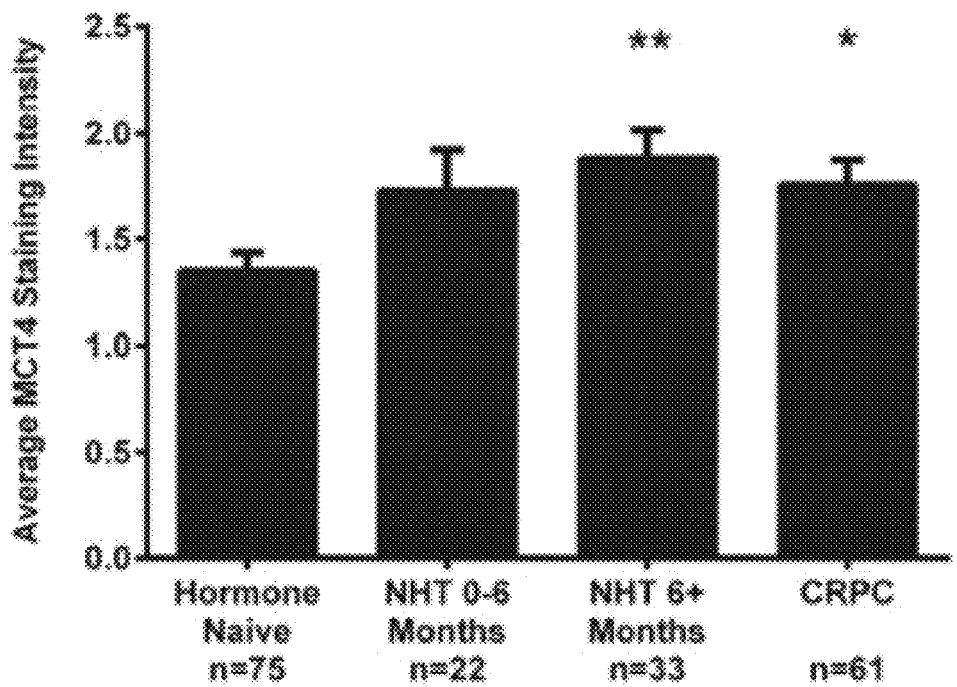
Figure 1E:
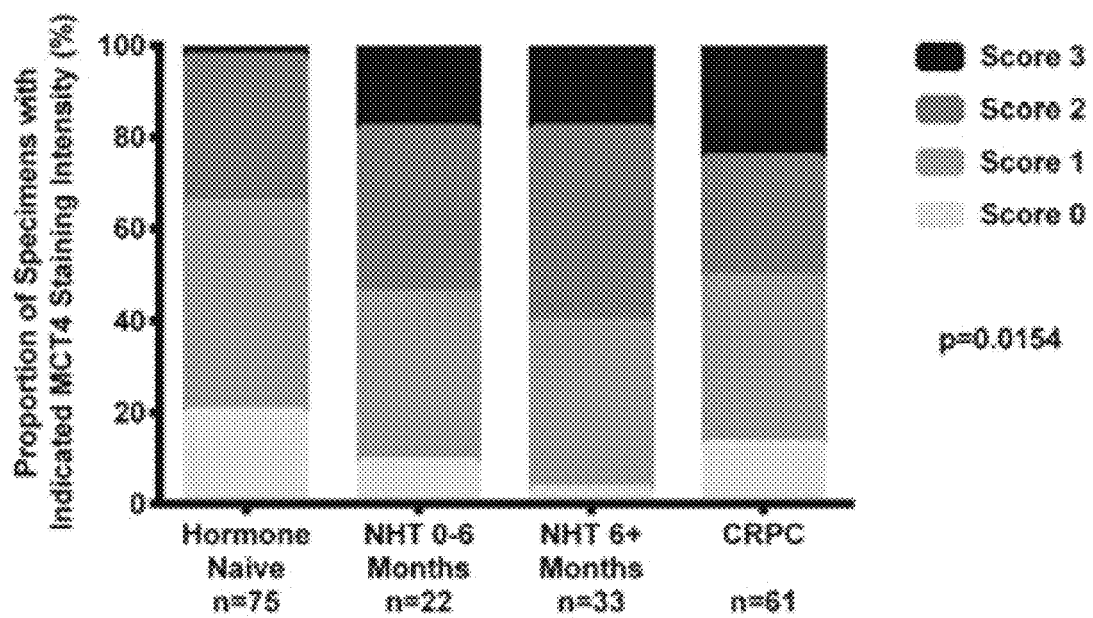

A tissue microarray (TMA) composed of tissues from Gleason grade 3, 4 and 5 human prostate cancers was stained for MCT4 protein. As shown in FIGS. 1A and B, Gleason grade 5 prostate cancers had significantly increased MCT4 protein expression relative to Gleason grade 3 and 4 specimens. Also, elevated MCT4 expression was associated with an earlier time to relapse from primary treatment as measured by increases in serum PSA levels, with the high MCT4-expressing cohort having a median time to relapse of 63.3 months vs. 94.2 months for the low MCT4-expressing cohort (FIG. 1C). Additionally, high MCT4 expression was correlated with other clinical characteristics associated with poor prognosis, such as higher serum PSA levels at diagnosis and clinical T stage (TABLE C). Furthermore, elevated MCT4 protein expression was found in tumours from patients subjected to prolonged neo-adjuvant hormone therapy (>6 months) and CRPC patients (FIGS. 1D and E), indicating that elevated expression of MCT4 protein in prostate cancer is associated with development of CRPC.

TABLE C

Clinico-pathological Characteristics Associated with High MCT4 Expression in Patient Samples

|  | Low MCT4 (0 + 1) | High MCT4 (2 + 3) | p-value |
|---|---|---|---|
| Gleason |  |  |  |
| <7 | 60.7% (17/28) | 39.3% (11/28) | 0.0061** |
| 7 | 52.0% (53/102) | 48.0% (49/102) |  |
| >7 | 29.1% (16/55) | 70.9% (39/55) |  |
| PSA |  |  |  |
| ≤10 ng/mL | 56.3% (71/126) | 43.7% (55/126) | 0.0157* |
| >10 ng/mL | 37.3% (22/59) | 62.7% (37/59) |  |
| T Stage |  |  |  |
| ≤pT2 | 55.4% (51/92) | 44.6% (41/92) | 0.0040** |
| ≥pT3 | 34.4% (32/93) | 65.6% (61/93) |  |
| Surgical Margin |  |  |  |
| Negative | 48.5% (50/103) | 51.5% (53/103) | 0.2595 |
| Positive | 40.2% (33/82) | 59.8% (49/82) |  |
| Capsule Invasion |  |  |  |
| Negative | 52.1% (49/94) | 47.9% (45/94) | 0.0435* |
| Positive | 37.4% (34/91) | 62.6% (57/91) |  |
| SV Invasion |  |  |  |
| Negative | 48.3% (72/149) | 51.7% (77/149) | 0.0544 |
| Positive | 30.6% (11/36) | 69.4% (25/36) |  |

Example 2: Knockdown of MCT4 Inhibits PC-3 Cell Proliferation

Figure 2A:
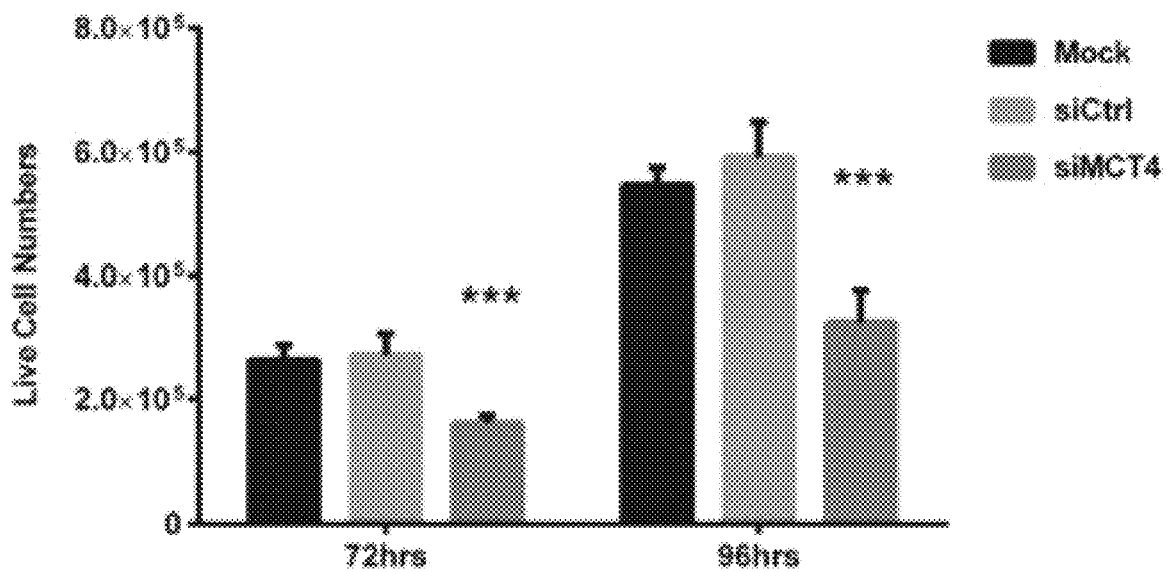
FIGS. 2A-2F shows the efficacy screening of MCT4-targeting ASOs using PC-3 cells in vitro for inhibition of MCT4 expression and cell proliferation, wherein MCT4 ASOs #1 (SEQ ID NO: 1) and #14 (SEQ ID NO: 5) exert their in vitro effects in a dose dependent manner, and the effects persist past 96 hours after transfection.
Figure 2B:
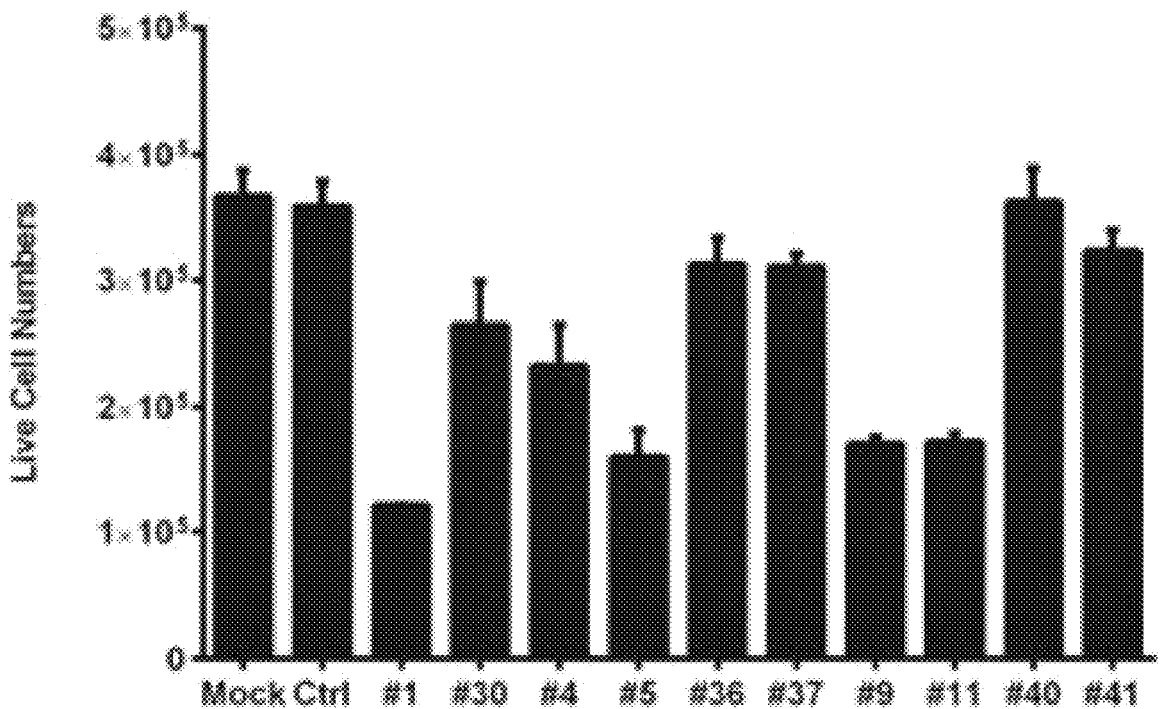
Figure 2D:
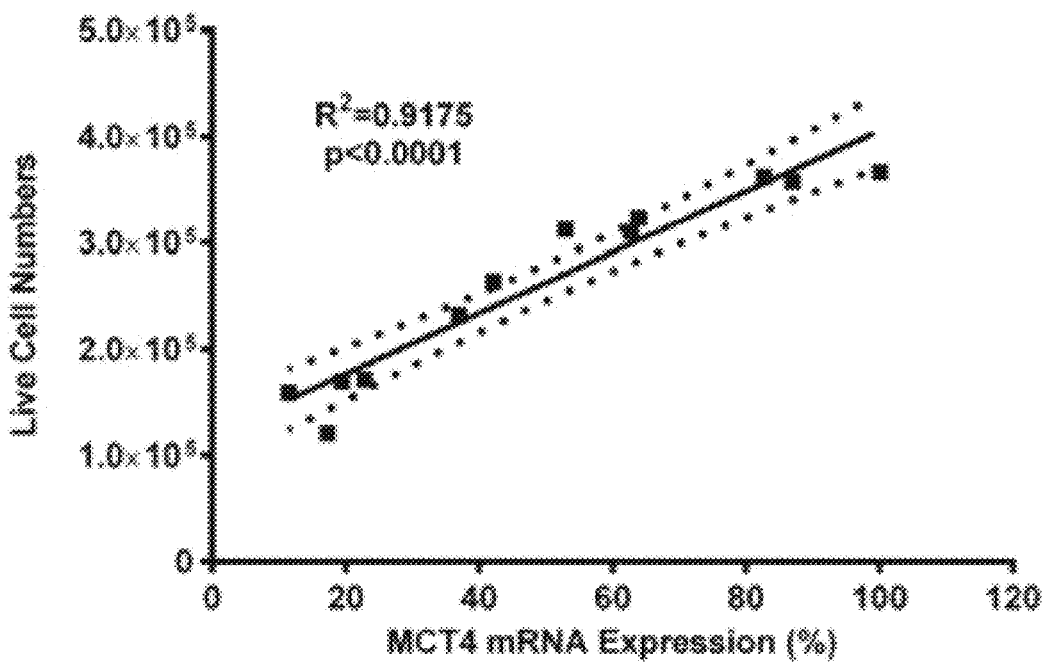
Figure 2C:
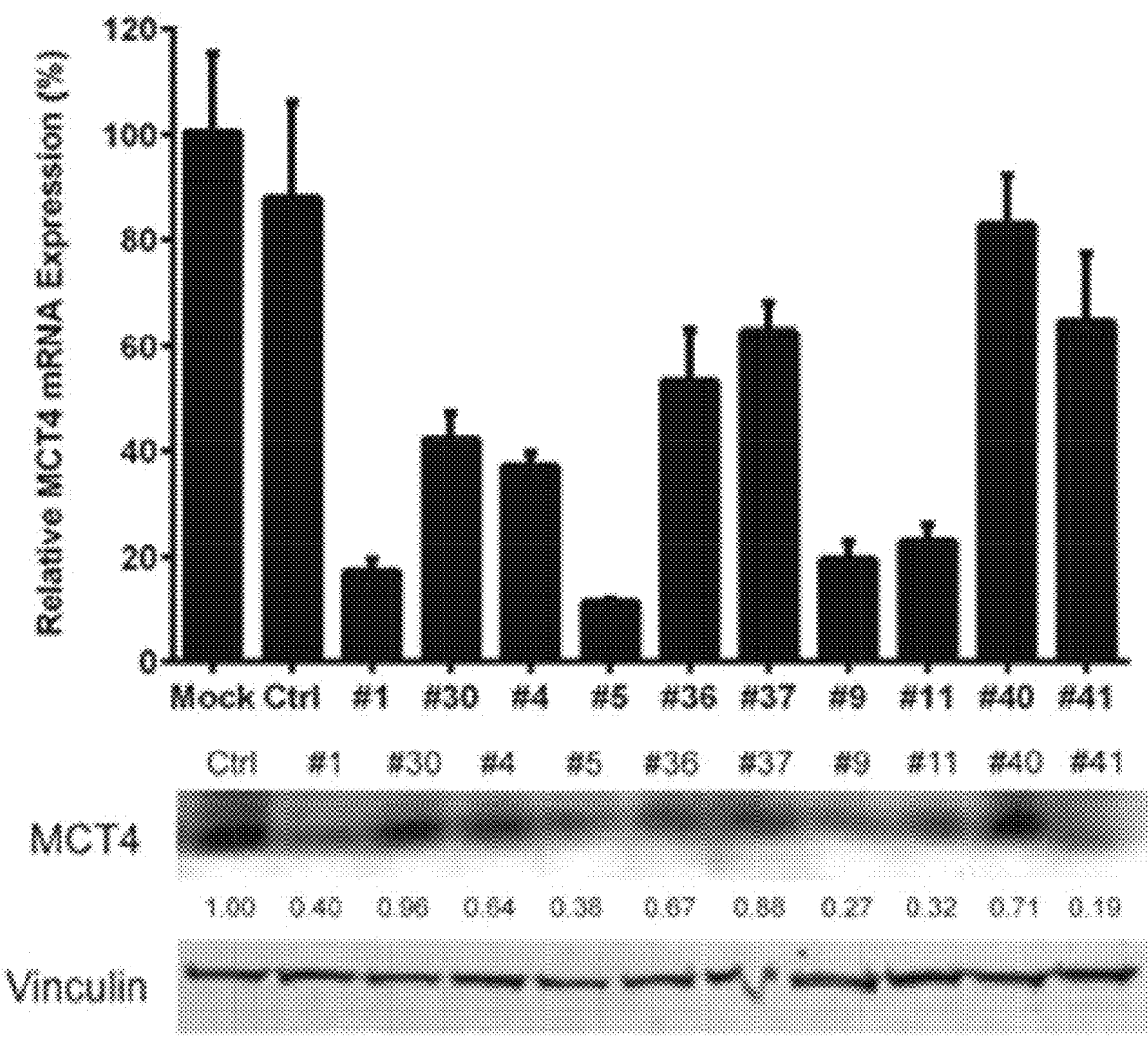

The potential therapeutic efficacy of inhibiting MCT4 expression was investigated using MCT4-targeting siRNAs and ASOs. Human PC-3 CRPC cells were used as they present a distinct glycolytic metabolic profile, a property associated with MCT4 expression (Vaz et al., 2012). As shown in FIG. 2A, treatment of PC-3 cells with MCT4 siRNA led to an inhibition of cell proliferation, suggesting potential therapeutic efficacy of an MCT4 knockdown approach. Accordingly, ASOs specifically targeting human MCT4 were designed. Screening of ten MCT4 ASOs revealed varying capacities of inhibiting PC-3 cell proliferation and MCT4 expression, with ASOs #1 (SEQ ID NO: 1) and #14 (SEQ ID NO: 5) showing the greatest potency (FIGS. 2B and 2C). A strong correlation was found between the reduced levels of MCT4 mRNA in PC-3 cells treated with the various ASOs and the resulting cell numbers (FIG. 2D), indicating that the growth inhibition by the ASOs was directly related to MCT4 knockdown.

Example 3: MCT4 ASOs Inhibit PC-3 Cell Proliferation

Figure 2E:
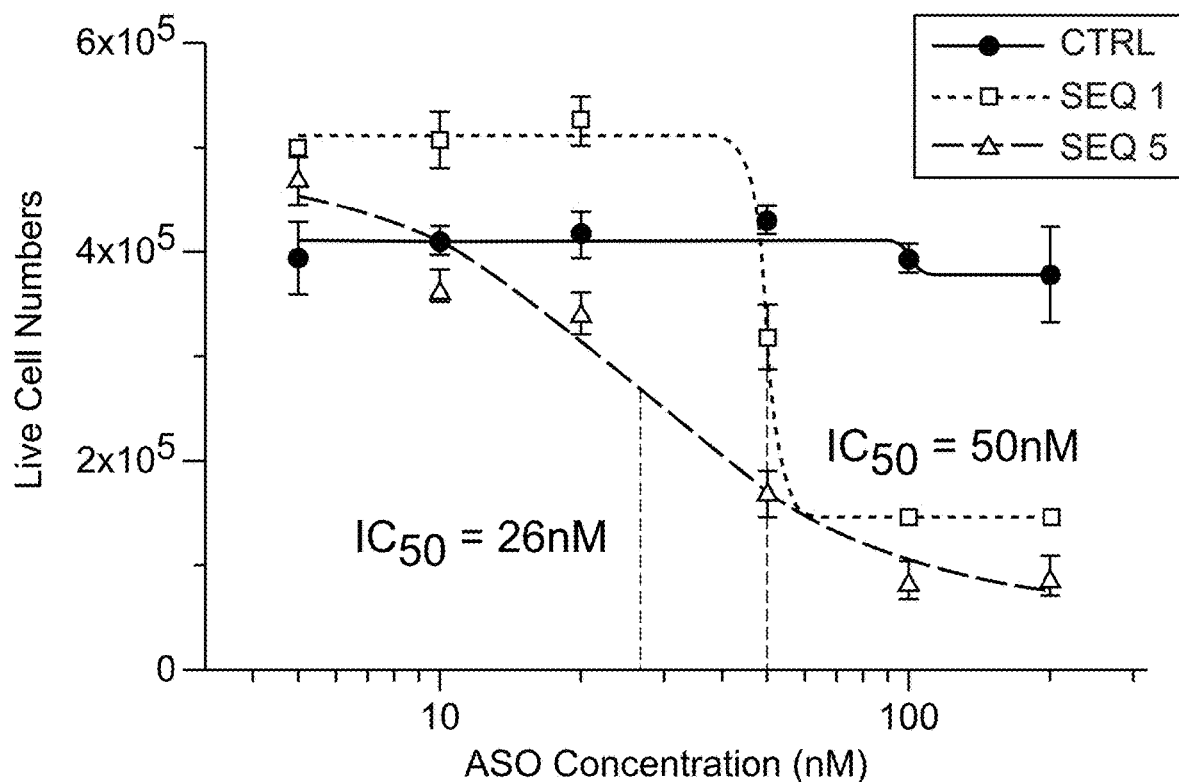
Figure 2E:
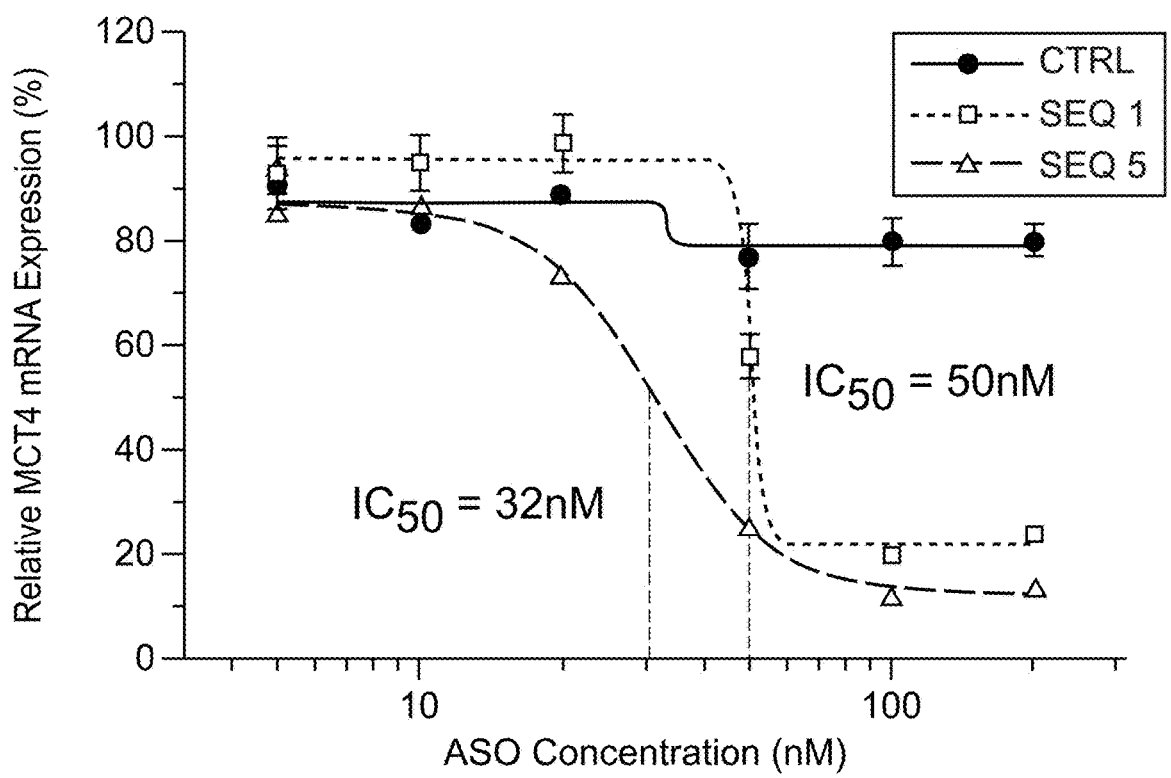
Figure 2E:
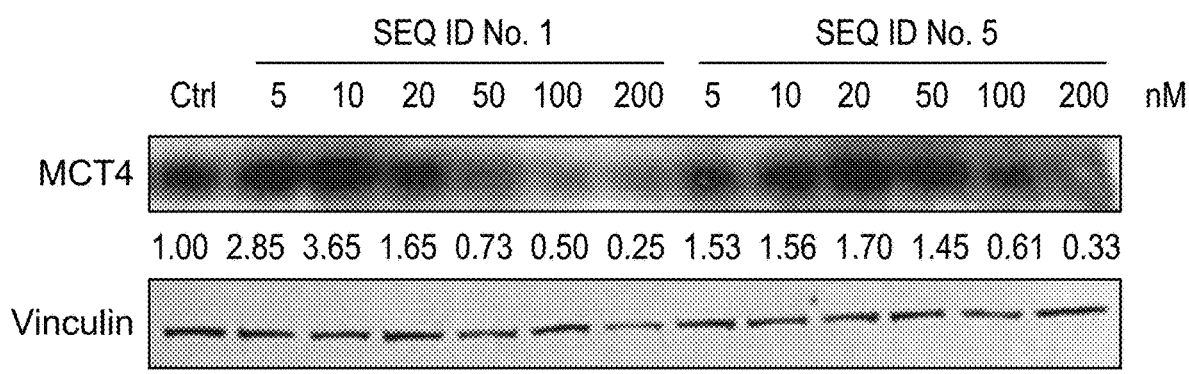
Figure 2F:
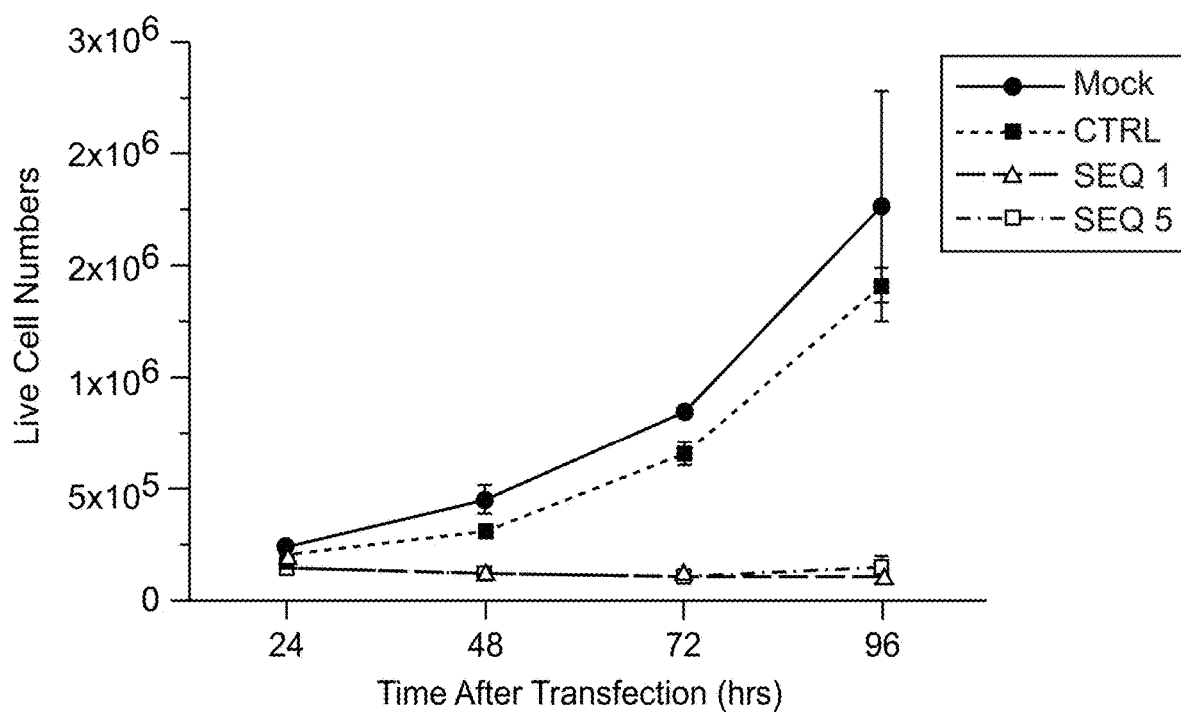
Figure 2F:
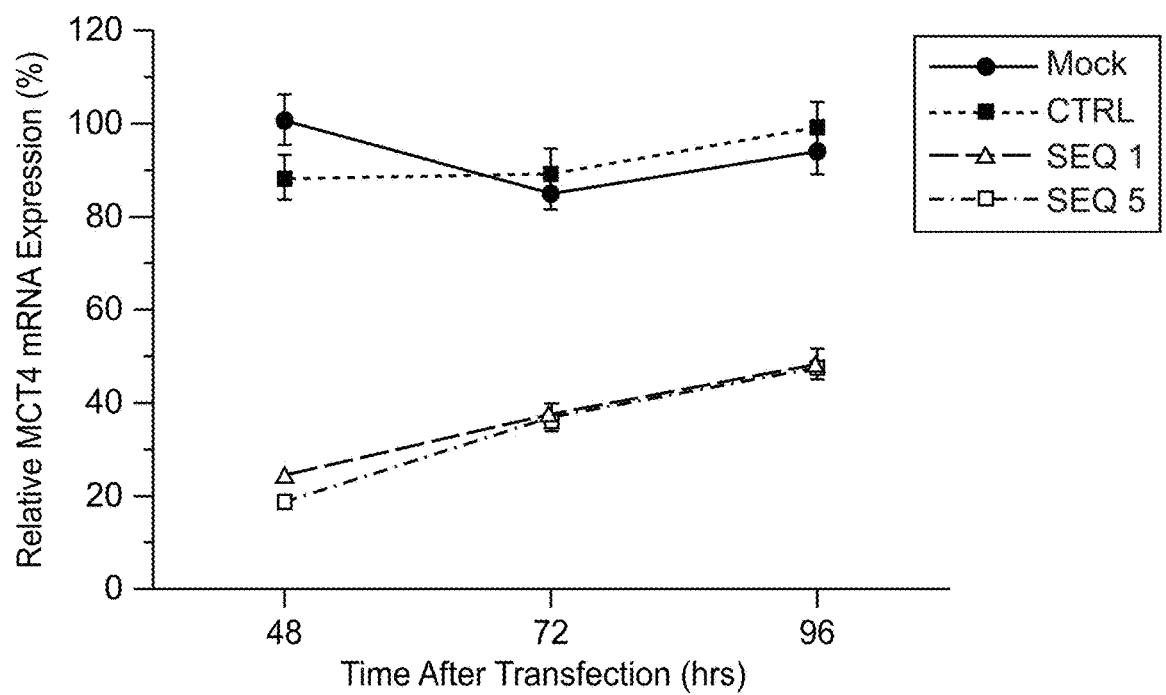
Figure 2F:
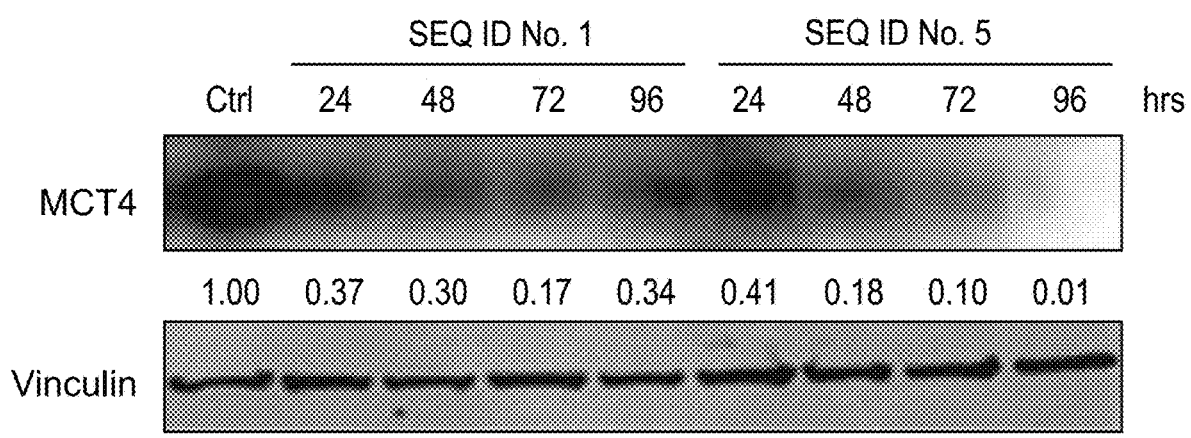

The growth-inhibitory activities of MCT4 ASOs #1 (SEQ ID NO: 1) and #14 (SEQ ID NO: 5) were further characterized. As shown in FIG. 2E, PC-3 cell proliferation was inhibited by both ASOs in a dose-dependent manner, with ASO #14 being slightly more effective (IC50=26 nM) than ASO #1 (IC50=50 nM). The ASOs also reduced MCT4 mRNA levels in a dose-dependent manner, mirroring their inhibition of cell proliferation (IC50 ASO #14=32 nM, IC50 ASO #1=50 nM). As shown in FIG. 2F, both ASOs maintained the inhibition of cell proliferation even at 96 hours post-transfection. While MCT4 mRNA levels began to increase slightly starting after 48 hours of transfection, MCT4 protein levels remained low even at 96 hours.

Example 4: MCT4 ASOs Exert Growth-Inhibition and a Reduction in MCT4 Expression in a Variety of Human Prostate Cancer Cell Lines and not Mouse MCT4

Figure 3A:
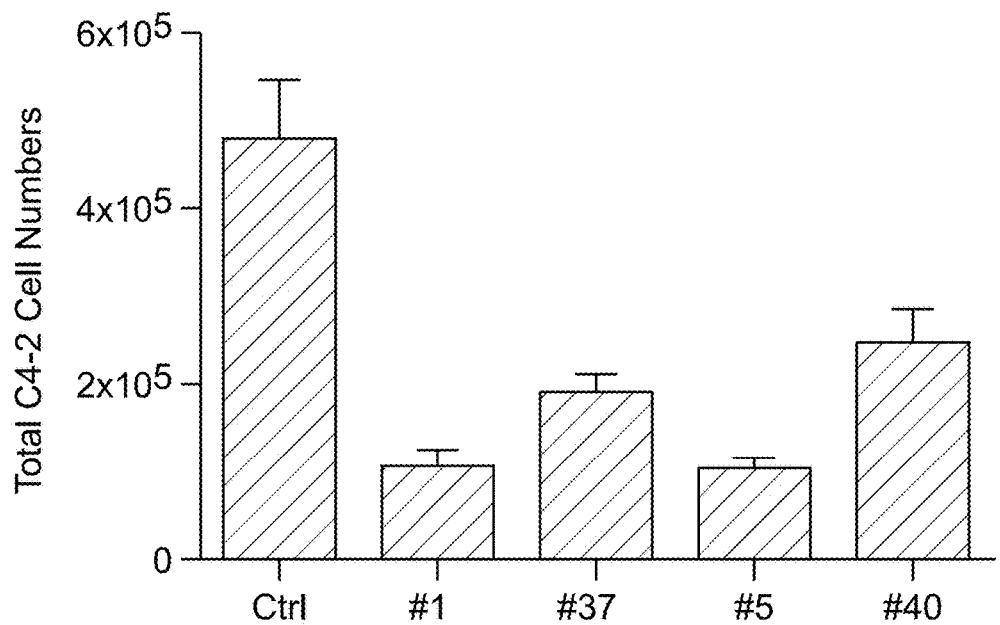
FIGS. 3A-3C shows MCT4 ASOs #1 (SEQ ID NO: 1) and #14 (SEQ ID NO: 5) are effective in vitro against human prostate cancer cells other than PC-3, but not against mouse prostate cancer cells.
Figure 3A:
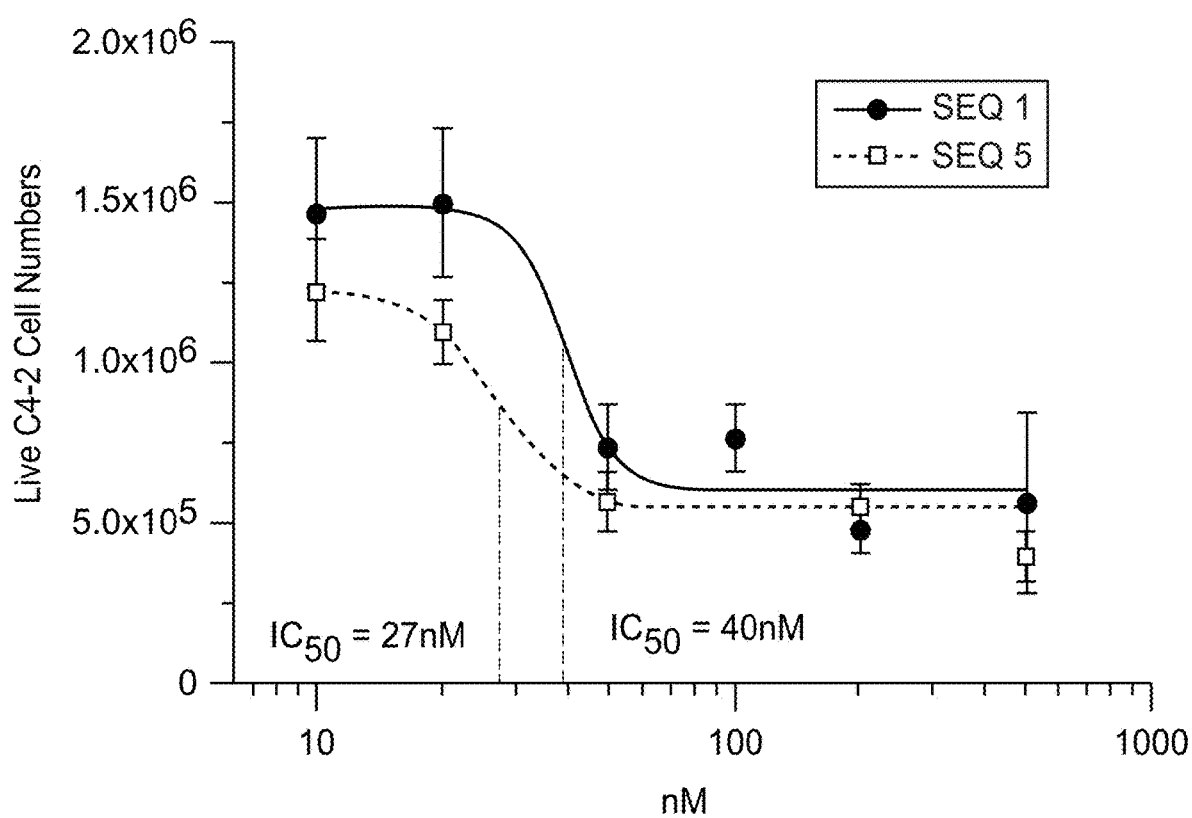
Figure 3A:
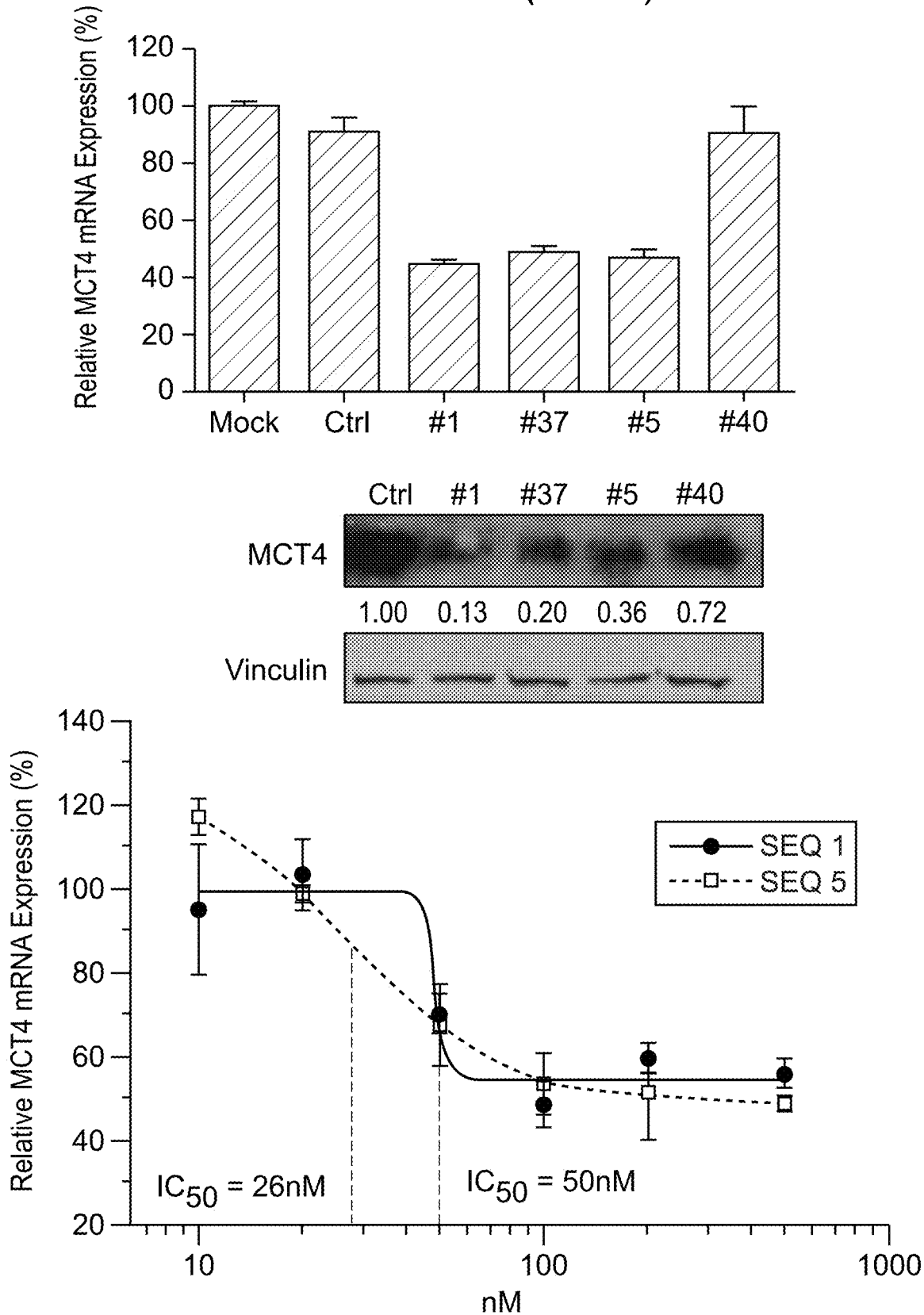
Figure 3B:
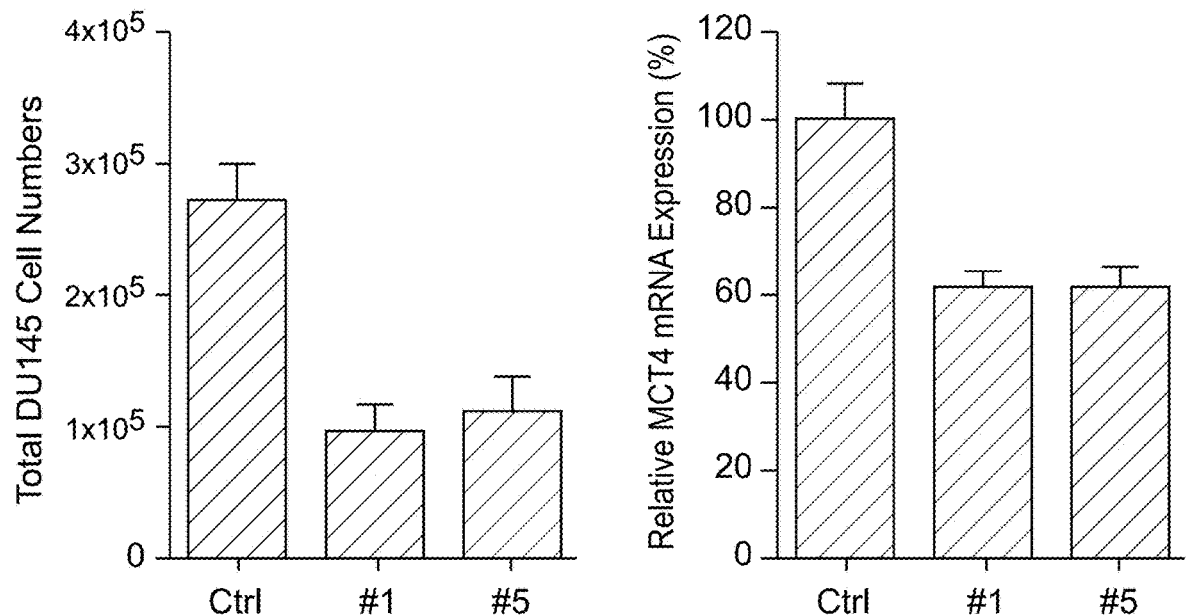
Figure 3B:
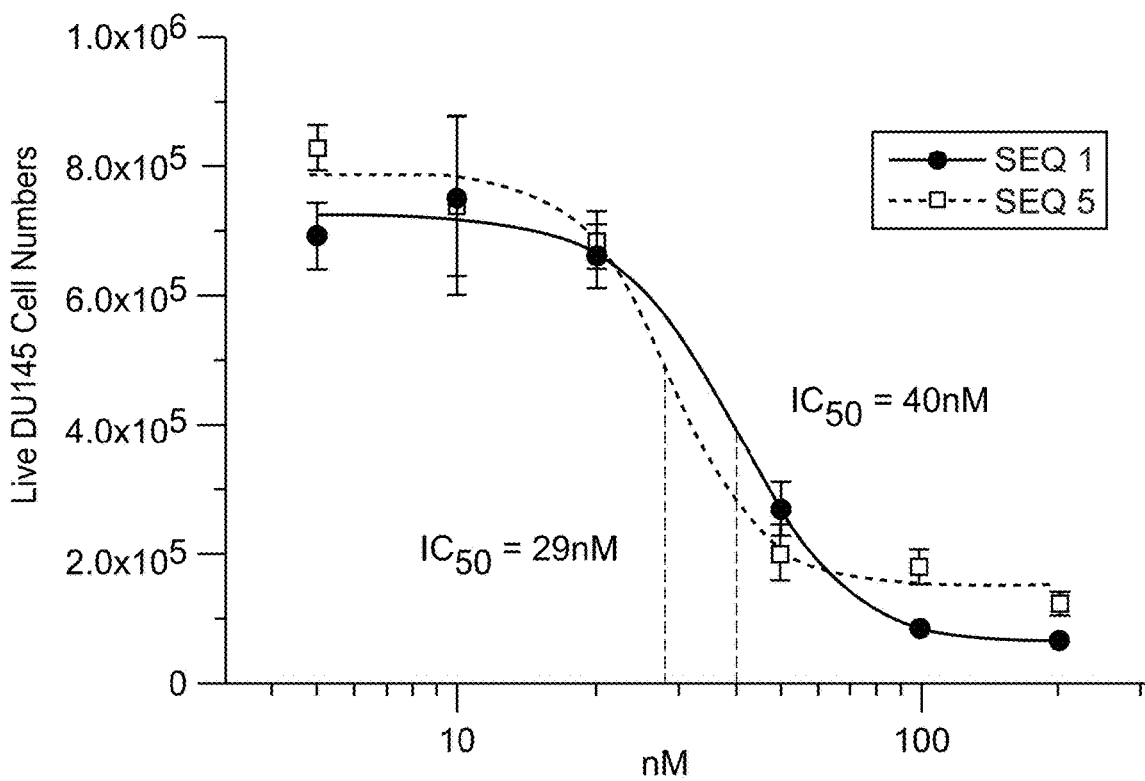
Figure 3C:
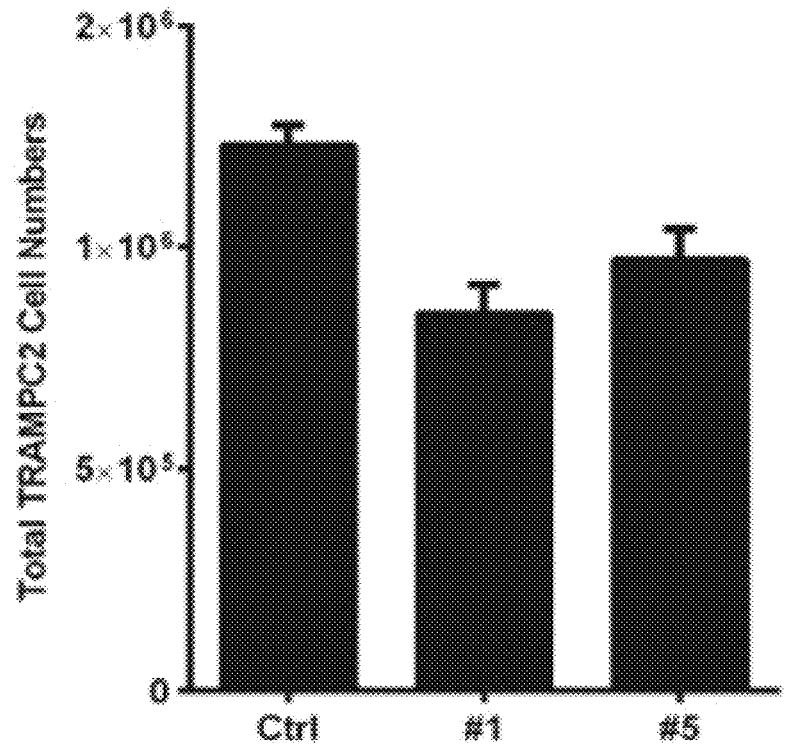
Figure 3C:
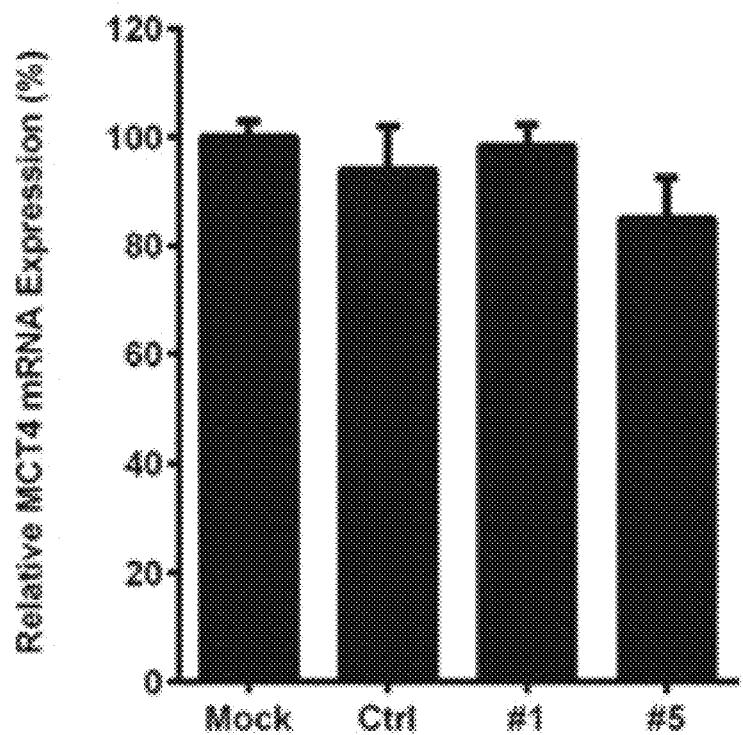
Figure 7A:
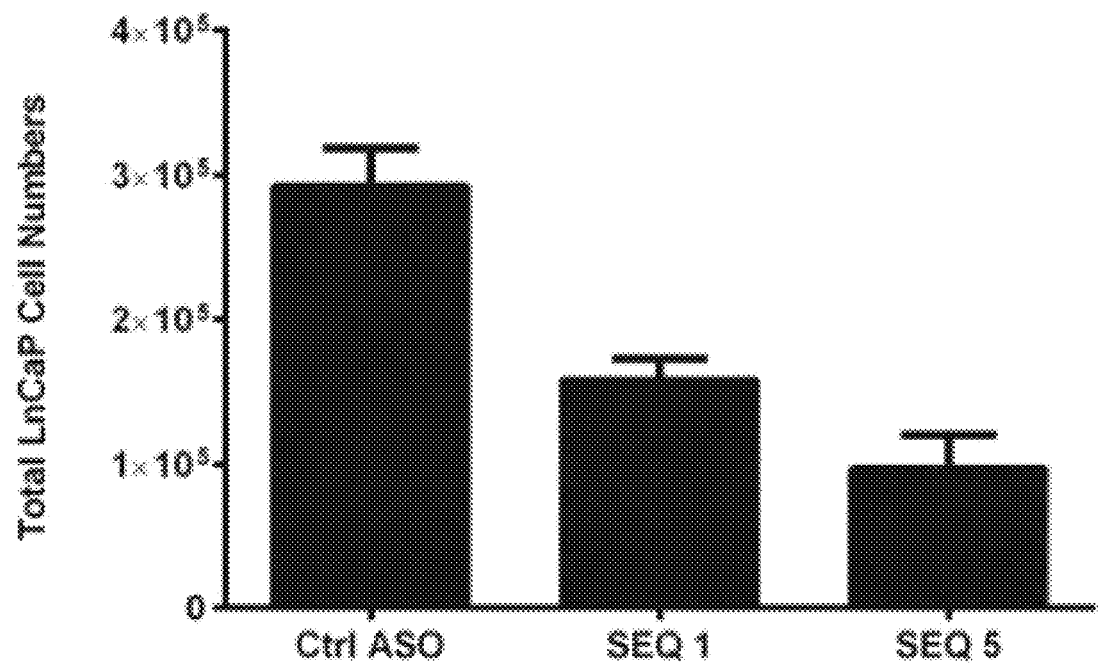
FIGS. 7A-7B shows that candidate MCT4-targeting ASOs are able to inhibit cell proliferation and MCT4 expression of LNCaP human prostate cancer cells 48 hours after transfection.
Figure 7B:
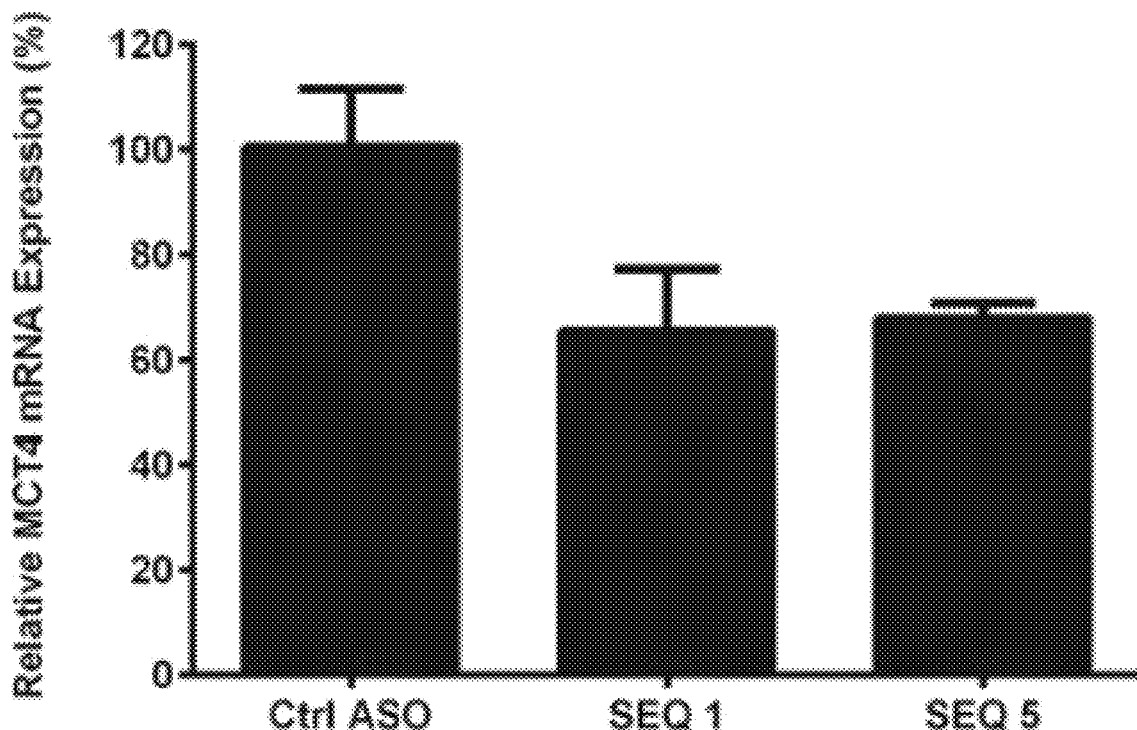

When the MCT4 ASOs #1 (SEQ ID NO: 1) and #14 (SEQ ID NO: 5) were transfected into human C4-2 CRPC cells they inhibited their proliferation with IC50 values comparable to those observed with PC-3 cells, i.e. ASO #1=40 nM, ASO #14=27 nM. Similarly, they reduced the MCT4 expression with IC50 values of 50 nM for ASO #1 and 26 nM for ASO #14 (FIG. 3A). Furthermore, when the ASOs were transfected into human DU145 prostate cancer cells, a similar inhibitory effect on cell proliferation and MCT4 expression was observed with almost identical IC50 values (FIG. 3B). Transfection of ASOs into LNCaP prostate cancer cells also showed a similar inhibition of cell proliferation and MCT4 expression (FIGS. 7A-7B), suggesting that the inhibitory effect is more associated with a glycolytic phenotype than androgen receptor status. Importantly, transfection of MCT4 ASOs #1 and #14 into mouse TRAMPC2 prostate cancer cells did not lead to a significant reduction in cell proliferation or mouse MCT4 expression (FIG. 3C). Taken together, the results suggest that these ASOs specifically target human MCT4 and that their inhibitory effect on cell proliferation is a consequence of MCT4 knock-down.

Figure 4A:
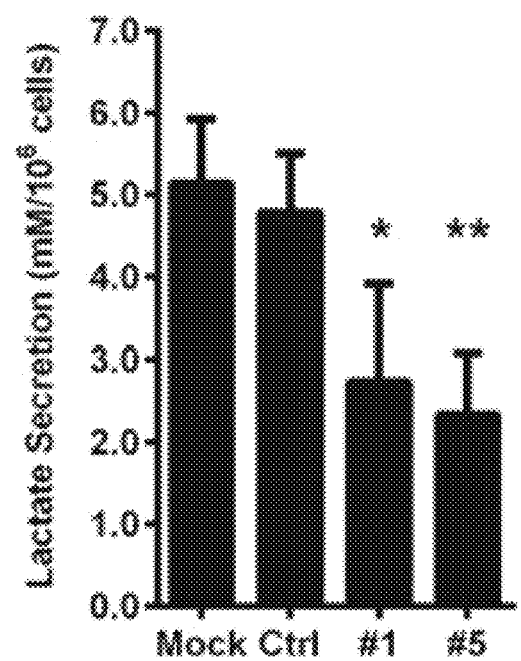
FIGS. 4A-4B shows that transfection of candidate MCT4 ASOs leads to inhibition of glucose metabolism of PC-3 cells.
Figure 4A:
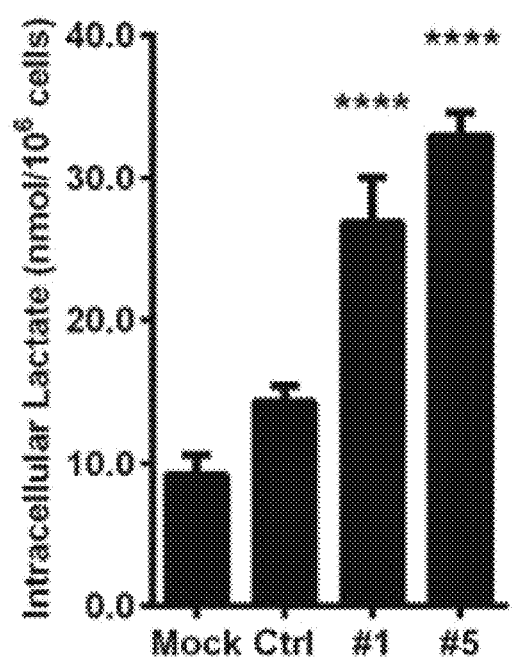
Figure 4B:
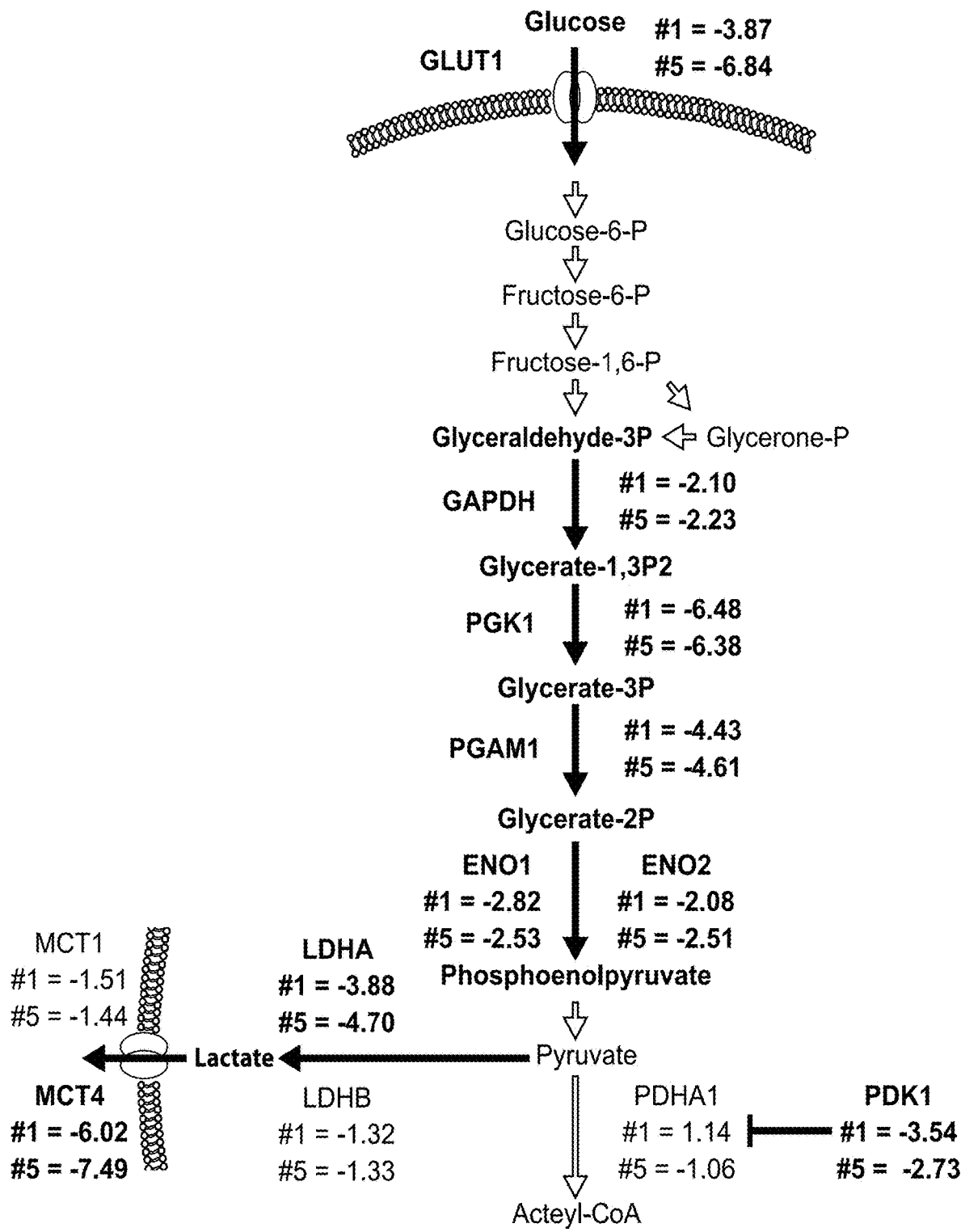

Example 5: Candidate MCT4 ASOs Inhibit Glucose Metabolism and Tissue Invasion/Migration of CRPC Cells In Vitro To further examine the effects of MCT4-targeting ASOs on prostate cancer cells, we measured their effects on lactic acid secretion, intracellular lactate concentrations, and glucose consumption of PC-3 cells. Transfection of the cells with MCT4 ASOs #1 (SEQ ID NO: 1) and #14 (SEQ ID NO: 5) led to a marked inhibition of lactic acid secretion, a corresponding accumulation of intracellular lactate and an extensive decrease in glucose consumption, measured after 48 hours of transfection (FIG. 4A). Furthermore, as shown in FIG. 4B, treatment with the ASOs resulted in down regulation of various genes involved in glycolysis, i.e. GAPDH, PGK1, PGAM1 and ENO1. In addition, expression of lactate dehydrogenase A (LDHA) was found to be depressed, indicative of a decrease in the conversion of pyruvate to lactic acid. Moreover, decreased expression was found for pyruvate dehydrogenase kinase-1 (PDK1), an enzyme that shunts pyruvate away from the TCA cycle and promotes its conversion to lactic acid. Thus the treatment with the MCT4 ASOs led to inhibition of aerobic glycolysis.

Figure 8A:
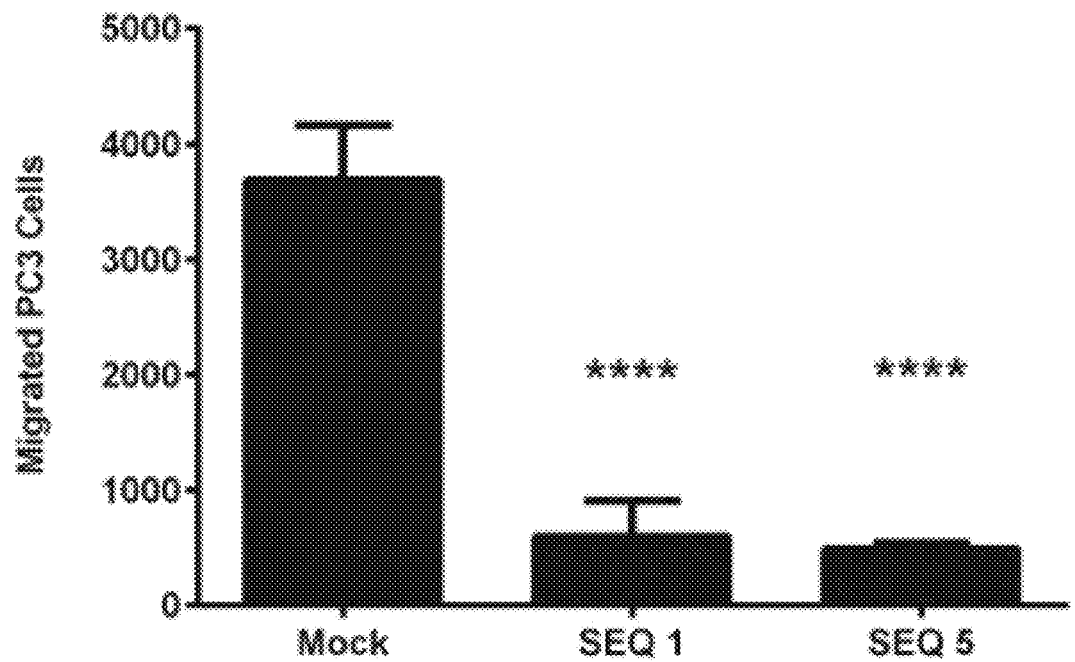
FIGS. 8A-8B shows that candidate MCT4 ASOs are able to inhibit PC-3 cell migration and tissue invasion in vitro.
Figure 8B:
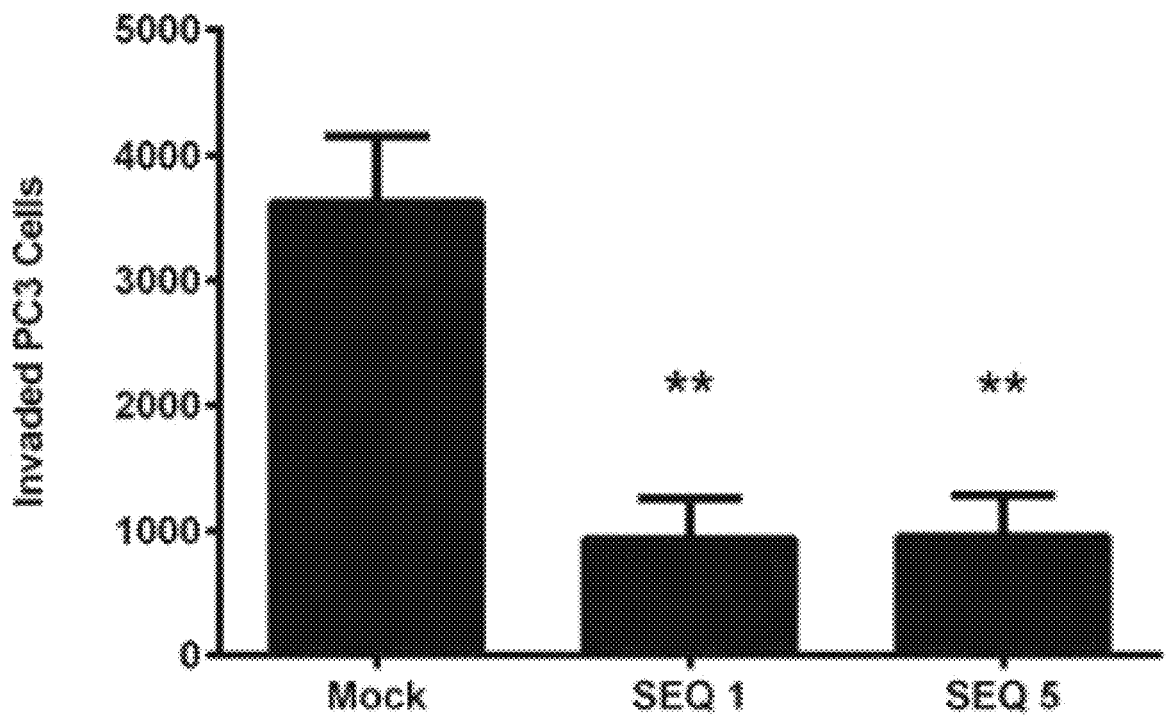

Treatment with MCT4 ASOs also inhibited the migration and tissue invasion of PC-3 cells in modified Boyden chambers (FIGS. 8A-8B), suggesting that lactic acid secretion as facilitated by MCT4 could also play an important role in the metastatic process.

Example 6: Growth of PC-3 Xenografts in Nude Mice Treated with MCT4 ASOs

Figure 5A:
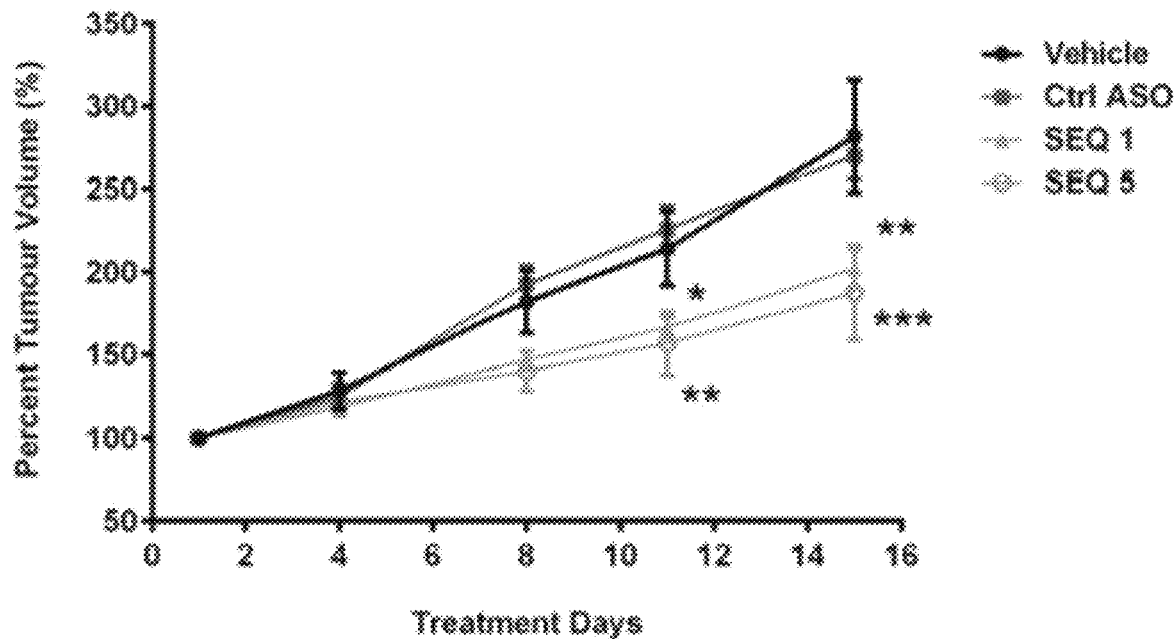
FIGS. 5A-5C shows MCT4 ASO-induced reduction of MCT4 expression in PC-3 tumour cells in vivo was associated with inhibition of PC-3 tumour growth, characterized by an increase in apoptosis and inhibition of cell proliferation, based on athymic nude mice bearing subcutaneous PC-3 tumours treated with intraperitoneal injections of MCT4 ASOs #1 (SEQ ID NO: 1), #14 (SEQ ID NO: 5), control ASO, or vehicle (PBS) at 10 mg/kg daily for 5 days followed by 2 days off treatment for a total of 15 days.
Figure 5C:
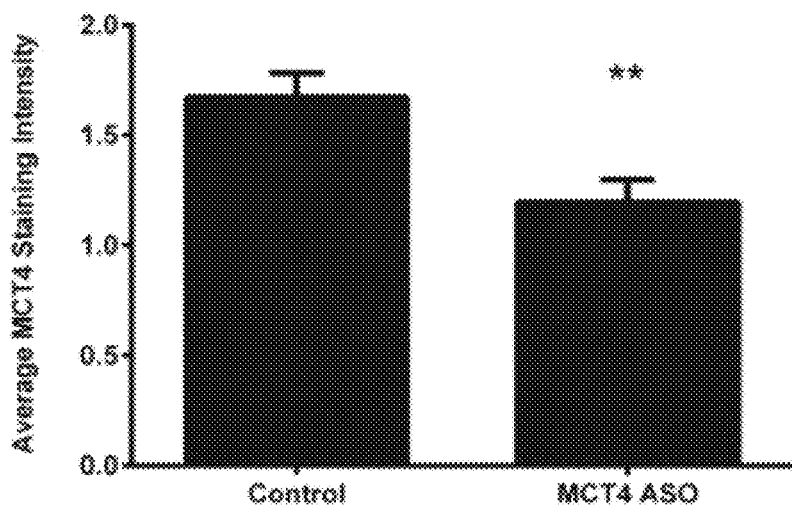
Figure 5B:
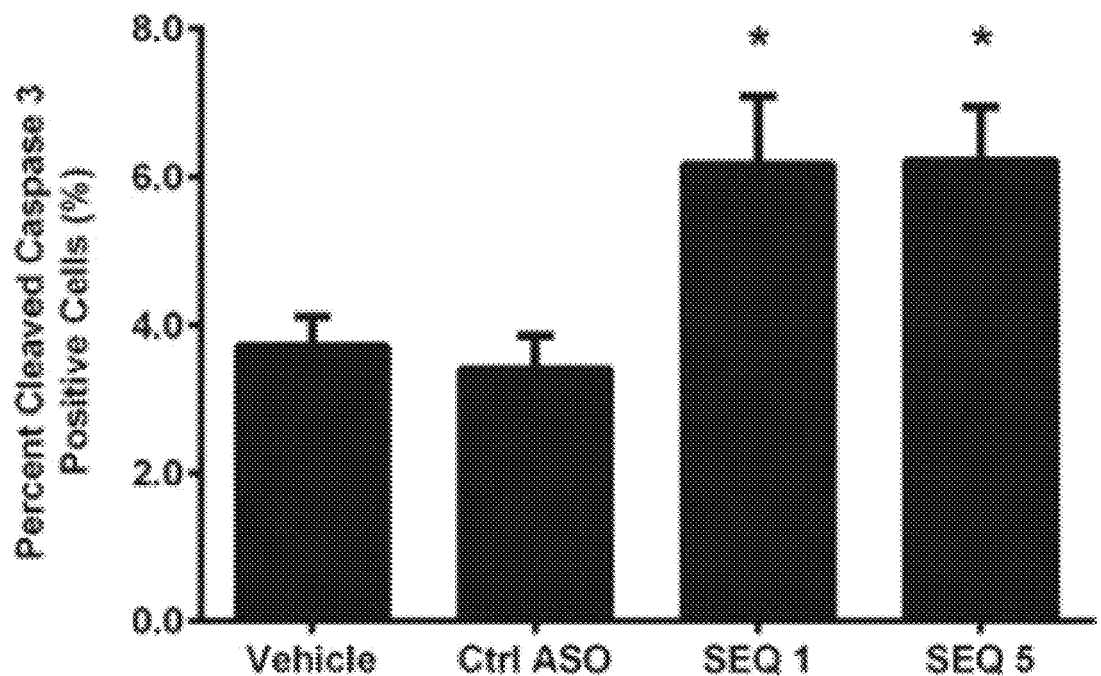
Figure 5B:
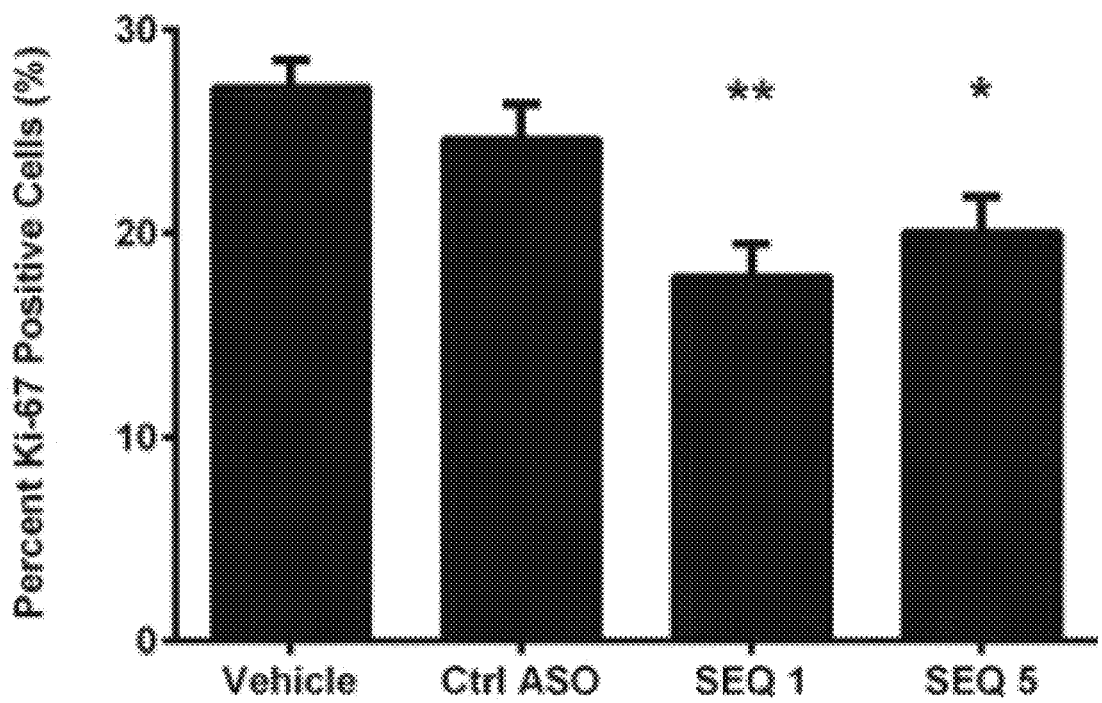
Figure 9A:
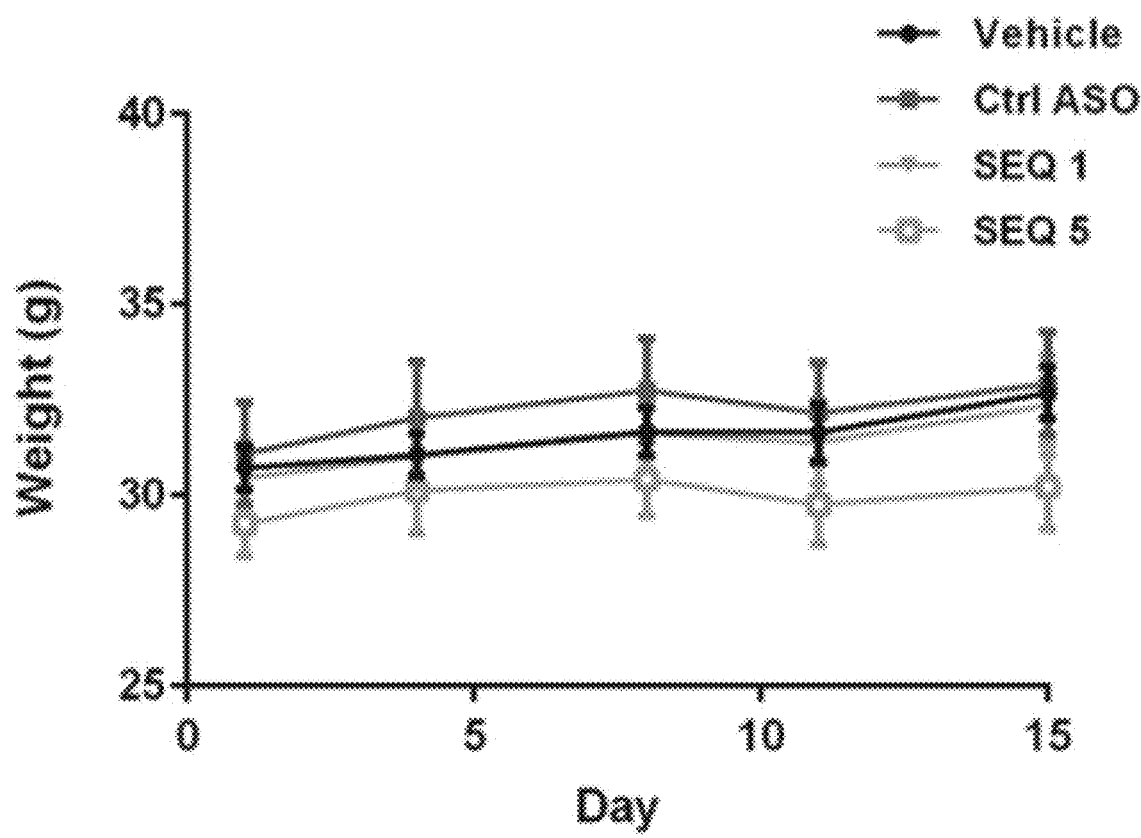
FIGS. 9A-9B shows that the treatment of nude mice with MCT4 ASO did not cause host toxicity as measured by animal weights.
Figure 9B:
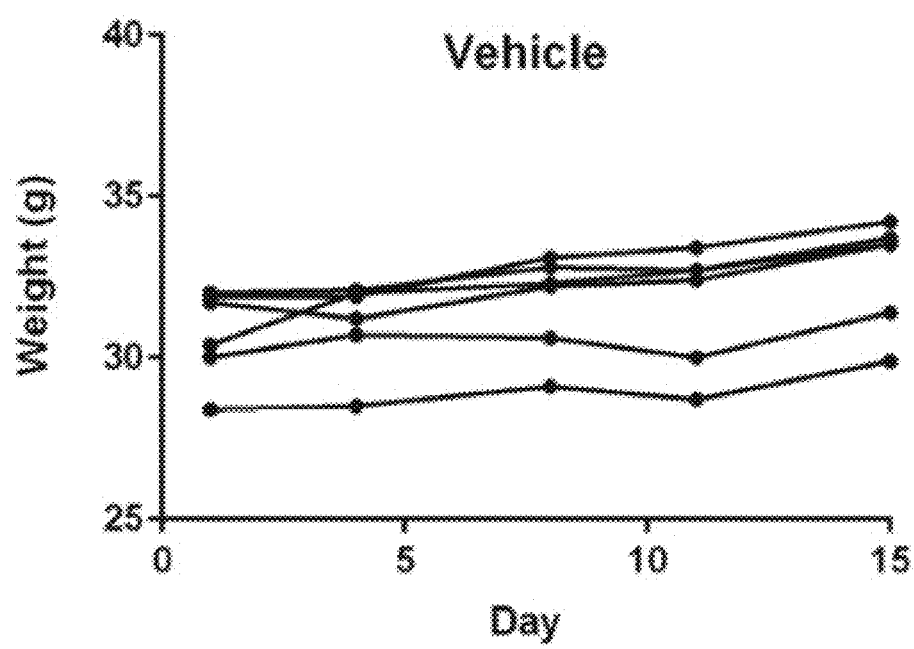
Figure 9B:
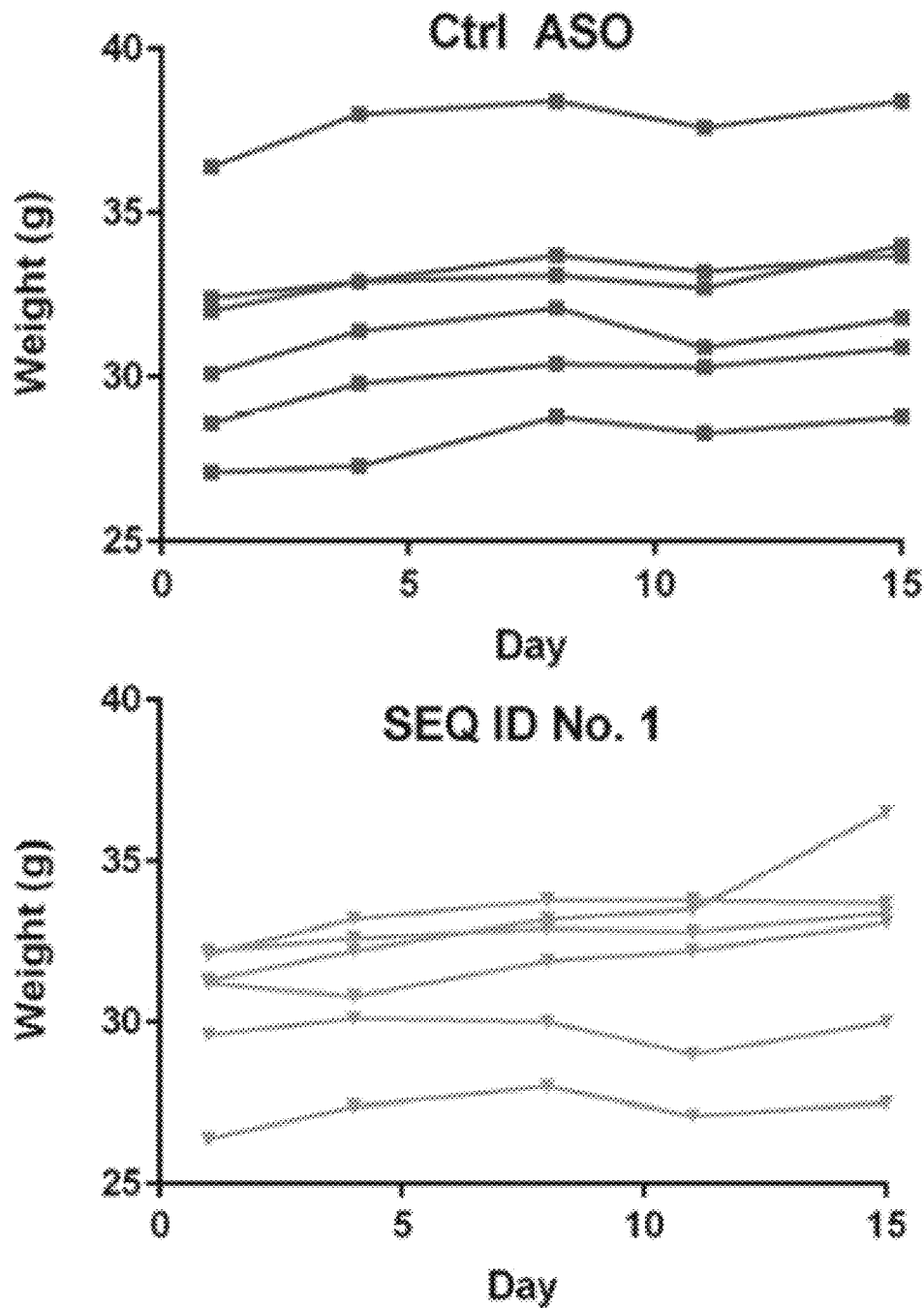
Figure 9B:
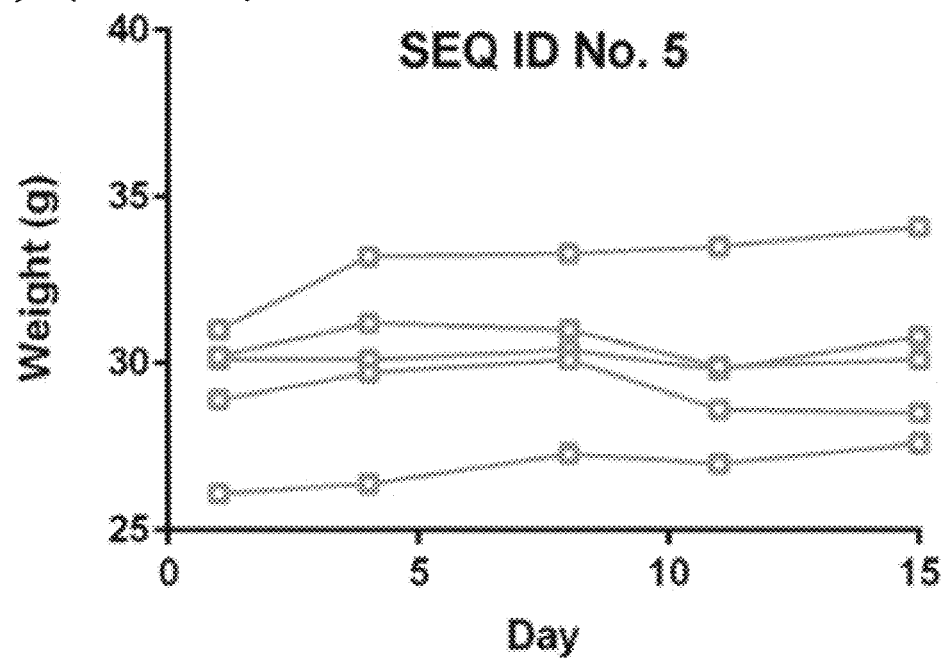

Male athymic nude mice bearing subcutaneous PC-3 tumours were treated with MCT4 ASOs #1 (SEQ ID NO: 1) and #14 (SEQ ID NO: 5) for a total of 15 days. Both ASOs markedly inhibited the growth of the tumours (FIG. 5A) without inducing major host toxicity as assessed by monitoring animal weights (FIGS. 9A-9B) and behaviour. Immunohistochemical analysis revealed that the ASO-induced inhibition of tumour growth was associated with an increase in cell apoptosis, as measured by cleaved-caspase 3 staining, and a decrease in cell proliferation, as measured by Ki-67 staining (FIG. 5B). The decrease in tumour growth was associated with a decrease in MCT4 protein expression (FIG. 5C), consistent with an anti-proliferative effect generated by MCT4 knockdown. Representative images of tumours from each group showed presence of strong membrane staining in the control tumours, which was absent in the MCT4 ASO-treated tumours (micrographs not shown).

Example 7: Effects of MCT4 ASOs on Immune Cell Aggregates in Nude Mice

Figure 6A:
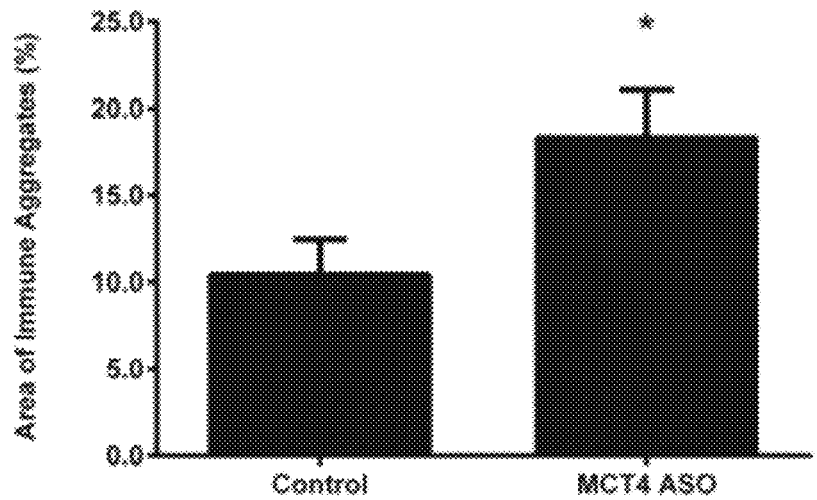
FIGS. 6A-6C shows that MCT4-targeting ASOs increase immune cell aggregation and alter tumour-associated immune cell proportions in vivo (i.e. NK cells and CD3 positive cells)
Figure 6B:
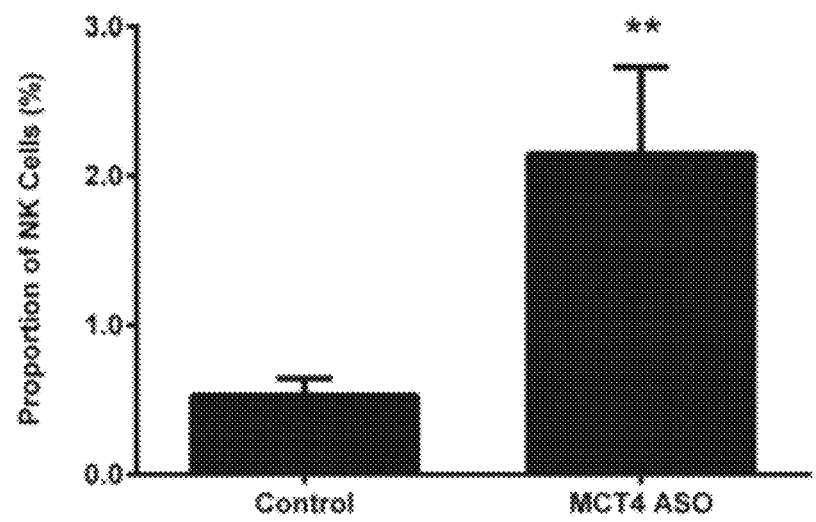
Figure 6C:
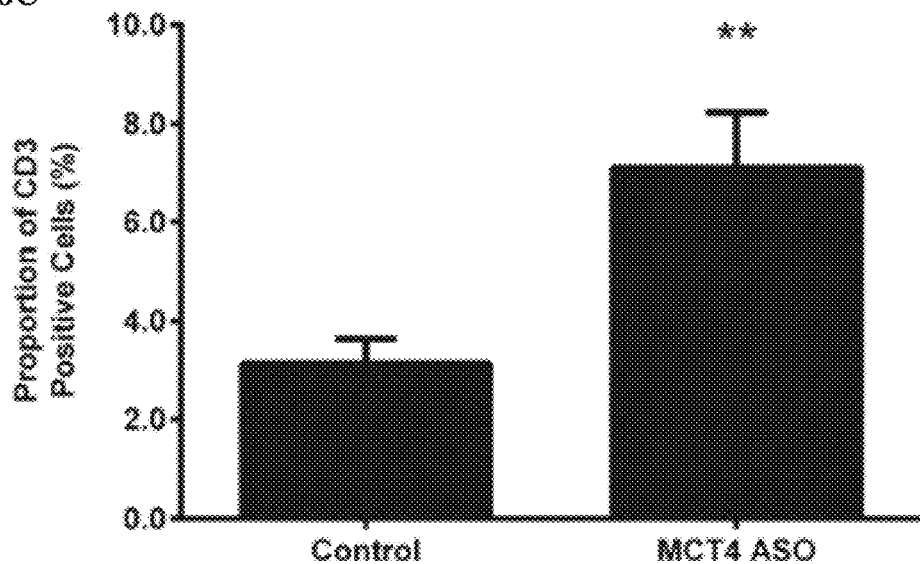

As lactic acid-induced acidification of tumours has been linked to suppression of local host anticancer immunity (Choi et al., 2013), it is of interest to determine whether the treatment of the PC-3 tumour-bearing nude mice with MCT4 ASOs causes changes in the local host immune response of these mice even though their immune reactivity was very limited. To that end, immune cell aggregates that had extravasated from CD31-positive blood vessels, particularly in the tumour periphery, were quantified. As shown in FIG. 6A, xenografts treated with the two MCT4 ASOs had significantly larger immune cell aggregates compared to control tumours. When micrographs were examined they showed immune aggregates are characterized by areas of small, circular, densely packed nuclei that are distinct from the surrounding tumour cells and staining for CD31 reveals that these immune cells have extravasated and surround the blood vessels in the tumour periphery (micrographs not shown). Quantification of the natural killer (NK) cell population, the predominant cytotoxic immune cell subtype in nude mice (Shultz et al., 2007), revealed that the treatment with the MCT4 ASOs markedly increased the proportion of tumour-associated NK cells (FIG. 6B). Furthermore, activation of NK cells is facilitated by CD3 (Koch et al., 2013), a molecule commonly regarded as a T-cell marker for its association with the T-cell receptor complex. Its expression in NK cells is detectable by immunohistochemistry (Morice, 2007), and in view of the absence of T cells in nude mice, can be used as an indicator of NK cell activation (Lanier et al., 1992). Treatment with MCT4 ASO also significantly altered the composition of the immune cells present in the aggregates, whereby staining using the NK cell marker NK1.1 revealed that there was an increased proportion of NK cells associated with the tumour (mircrographs not shown). As shown in FIG. 6C, the proportion of CD3 positive cells increased with MCT4 ASO treatment. While staining revealed that the proportion of activated NK cells associated with the ASO-treated tumours had also increased, suggesting stimulation of anti-cancer immunity.

Example 8: Combination Therapies with SEQ ID NO: 5

Figure 10A:
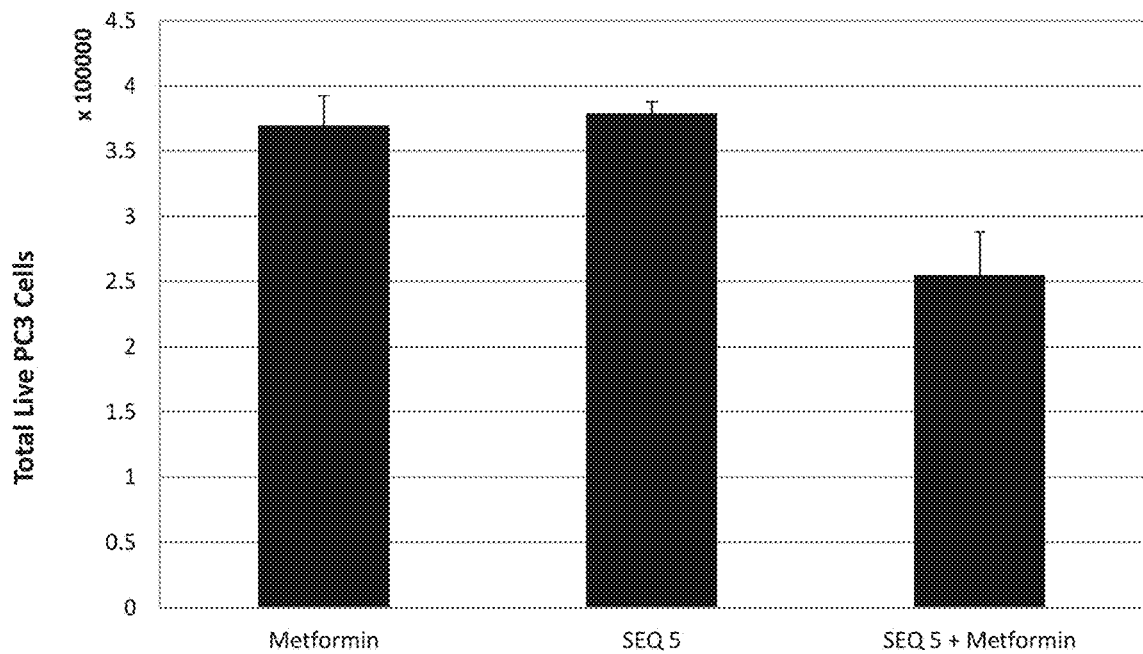
FIG. 10A-10D shows a comparison the total live cell numbers assessed 48 hours after treatment with SEQ ID NO:5 ASO, Metformin, Doxycycline, Docetaxel and MDV3100, wherein SEQ ID NO:5 ASO was tested in comparison to each of Metformin, Doxycycline, Docetaxel and MDV3100, alone and in combination.
Figure 10B:
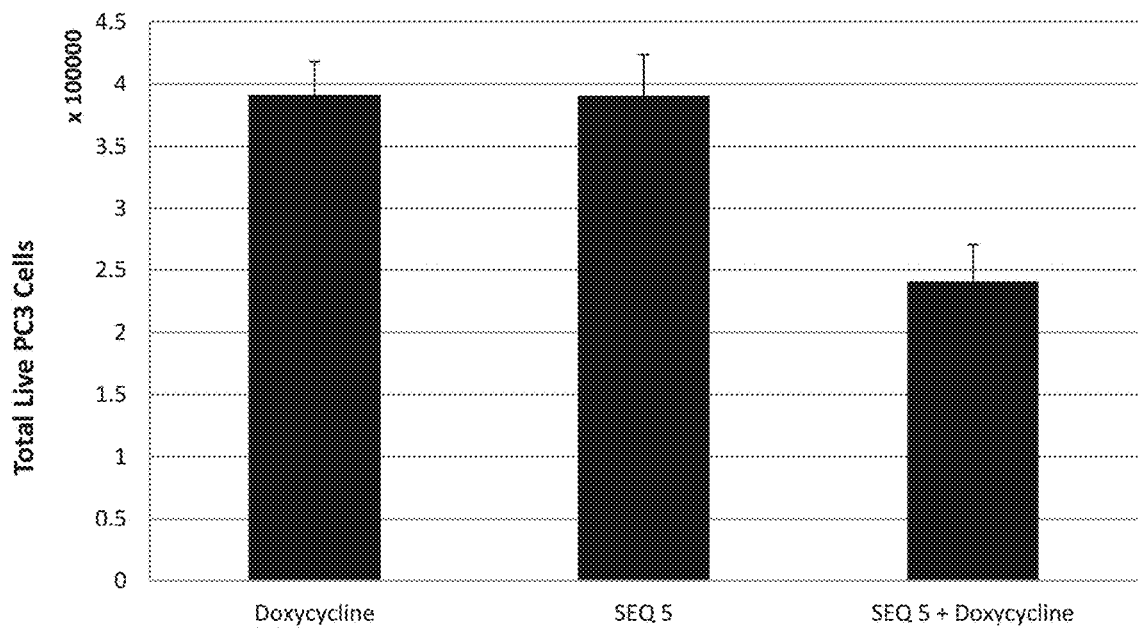
Figure 10C:
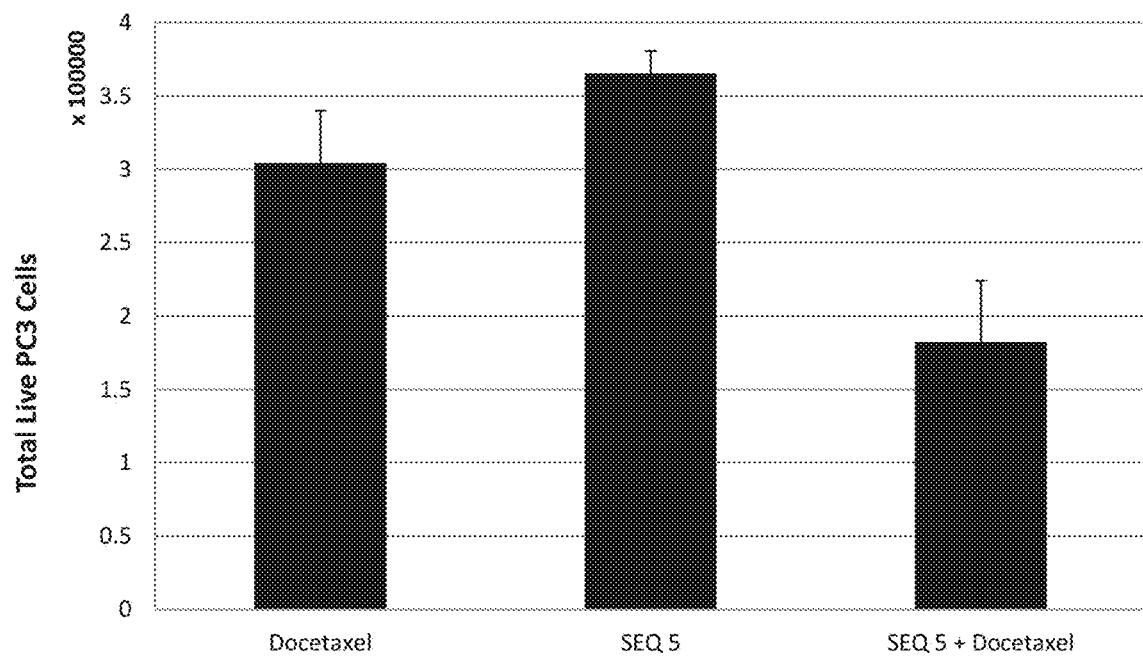
Figure 10D:
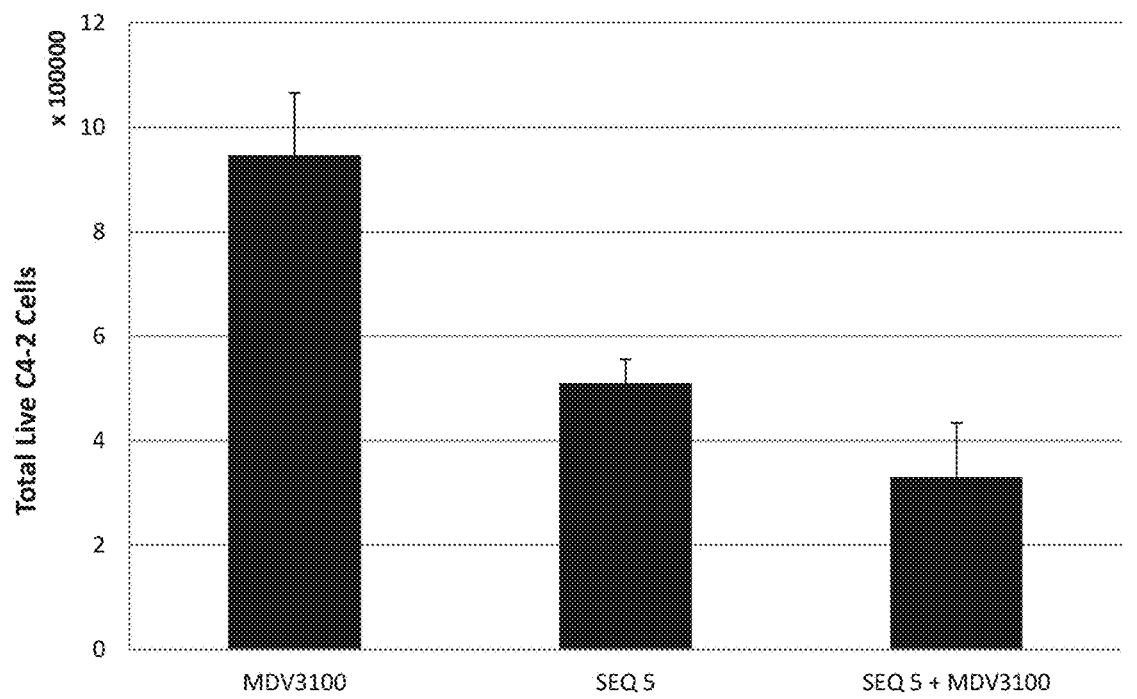

Various combination strategies were screened at the approximate $IC_{50}$ concentrations to determine whether synergistic effects may be found by combining current cancer therapeutics (see TABLE D) with MCT4 ASO SEQ ID NO:5. In FIGS. 10A-C, the total live PC3 cell numbers were assessed 48 hours after treatment with Metformin, Doxycycline and docetaxel both alone and in combination with MCT4 ASO SEQ ID NO:5. However, C4-2 cells were used to test MDV3100, SEQ ID NO:5 and a combination of SEQ ID NO:5 and MDV3100 (FIG. 10D). The combination of Docetaxel with MCT4 ASO SEQ ID NO:5 showed synergistic effect with Combination Index=0.780.

TABLE D $IC_{50}$ Concentrations of SEQ ID No. 5, Metformin, Doxycycline, Docetaxel MDV3100

| Drug | $IC_{50}$ Concentration | Drug Category |
| --- | --- | --- |
| SEQ ID No. 5 | 50 nM | MCT4 inhibitory ASO |
| Metformin | 4 mM | Modulator of glucose metabolism |
| Doxycycline | 15 µM | Possible mitochondrial inhibitor |
| Docetaxel | 2.5 nM | Approved chemotherapy for prostate cancer |
| MDV3100 | 50 µM | Approved second-generation anti-androgen for prostate cancer |

Although embodiments described herein have been described in some detail by way of illustration and example for the purposes of clarity of understanding, it will be readily apparent to those of skill in the art in light of the teachings described herein that changes and modifications may be made thereto without departing from the spirit or scope of the appended claims. Such modifications include the substitution of known equivalents for any aspect of the invention in order to achieve the same result in substantially the same way. Numeric ranges are inclusive of the numbers defining the range. The word "comprising" is used herein as an open ended term, substantially equivalent to the phrase "including, but not limited to", and the word "comprises" has a corresponding meaning. As used herein, the singular forms "a", "an" and "the" include plural referents unless the context clearly dictates otherwise. Thus, for example, reference to "a thing" includes more than one such thing. Citation of references herein is not an admission that such references are prior art to an embodiment of the present invention. The invention includes all embodiments and variations substantially as herein described and with reference to the figures.

REFERENCES

Albertsen, P. C., Hanley, J. A., and Fine, J. (2005). 20-year outcomes following conservative management of clinically localized prostate cancer. JAMA 293, 2095-2101.

Badrising, S., van der Noort, V., van Oort, I. M., van den Berg, H. P., Los, M., Hamberg, P., Coenen, J. L., van den Eertwegh, A. J., de Jong, L. J., Kerver, E. D., et al. (2014). Clinical activity and tolerability of enzalutamide (MDV3100) in patients with metastatic, castration-resistant prostate cancer who progress after docetaxel and abiraterone treatment. Cancer 120, 968-975.

Beltran, H., Rickman, D. S., Park, K., Chae, S. S., Sboner, A., MacDonald, T. Y., Wang, Y., Sheikh, K. L., Terry, S., Tagawa, S. T., et al. (2011). Molecular characterization of neuroendocrine prostate cancer and identification of new drug targets. Cancer Discov 1, 487-495.

Bishr M and Saad F. Overview of the latest treatments for castration-resistant prostate cancer. Nat Rev Urol. 2013; 10(9):522-528.

Chiang, Y. T., Wang, K., Fazli, L., Qi, R. Z., Gleave, M. E., Collins, C. C., Gout, P. W., and Wang, Y. (2014). GATA2 as a potential metastasis-driving gene in prostate cancer. Oncotarget 5, 451-461.

Choi, S. Y., Collins, C. C., Gout, P. W., and Wang, Y. (2013). Cancer-generated lactic acid: a regulatory, immunosuppressive metabolite? J Pathol 230, 350-355.

Choi, S. Y., Lin, D., Gout, P. W., Collins, C. C., Xu, Y., and Wang, Y. (2014). Lessons from patient-derived xenografts for better in vitro modeling of human cancer. Adv Drug Deliv Rev 79-80, 222-237.

Claessens F, Helsen C, Prekovic S, Van den Broeck T, Spans L, Van Poppel H and Joniau S. Emerging mechanisms of enzalutamide resistance in prostate cancer. Nat Rev Urol. 2014; 11(12):712-716.

de Bono, J. S., Logothetis, C. J., Molina, A., Fizazi, K., North, S., Chu, L., Chi, K. N., Jones, R. J., Goodman, O. B., Saad, F., et al. (2011). Abiraterone and increased survival in metastatic prostate cancer. N Engl J Med 364, 1995-2005.

Dias, N., and Stein, C. A. (2002). Antisense oligonucleotides: basic concepts and mechanisms. Mol Cancer Ther 1, 347-355.

Dimmer, K. S., Friedrich, B., Lang, F., Deitmer, J. W., and Bröer, S. (2000). The low-affinity monocarboxylate transporter MCT4 is adapted to the export of lactate in highly glycolytic cells. Biochem J 350 Pt 1, 219-227.

Doherty, J. R., and Cleveland, J. L. (2013). Targeting lactate metabolism for cancer therapeutics. J Clin Invest 123, 3685-3692.

Fisel, P., Kruck, S., Winter, S., Bedke, J., Hennenlotter, J., Nies, A. T., Scharpf, M., Fend, F., Stenzl, A., Schwab, M., et al. (2013). DNA methylation of the SLC16A3 promoter regulates expression of the human lactate transporter MCT4 in renal cancer with consequences for clinical outcome. Clin Cancer Res 19, 5170-5181.

Gerlinger, M., Santos, C. R., Spencer-Dene, B., Martinez, P., Endesfelder, D., Burrell, R. A., Vetter, M., Jiang, M., Saunders, R. E., Kelly, G., et al. (2012). Genome-wide RNA interference analysis of renal carcinoma survival regulators identifies MCT4 as a Warburg effect metabolic target. J Pathol 227, 146-156.

Gravel, S. P., Andrzejewski, S., Avizonis, D., and St-Pierre, J. (2014a). Stable isotope tracer analysis in isolated mitochondria from mammalian systems. Metabolites 4, 166-183.

Gravel, S. P., Hulea, L., Toban, N., Birman, E., Blouin, M. J., Zakikhani, M., Zhao, Y., Topisirovic, I., St-Pierre, J., and Pollak, M. (2014b). Serine deprivation enhances antineoplastic activity of biguanides. Cancer Res 74, 7521-7533.

Halestrap, A. P. (2013). The SLC16 gene family—structure, role and regulation in health and disease. Mol Aspects Med 34, 337-349.

Hanahan, D., and Weinberg, R. A. (2011). Hallmarks of cancer: the next generation. Cell 144, 646-674.

Hao, J., Chen, H., Madigan, M. C., Cozzi, P. J., Beretov, J., Xiao, W., Delprado, W. J., Russell, P. J., and Li, Y. (2010). Co-expression of CD147 (EMMPRIN), CD44v3-10, MDR1 and monocarboxylate transporters is associated with prostate cancer drug resistance and progression. Br J Cancer 103, 1008-1018.

Jadvar, H. (2009). Molecular imaging of prostate cancer with 18F-fluorodeoxyglucose PET. Nat Rev Urol 6, 317-323.

Koch, J., Steinle, A., Watzl, C., and Mandelboim, O. (2013). Activating natural cytotoxicity receptors of natural killer cells in cancer and infection. Trends Immunol 34, 182-191.

Koochekpour, S., Majumdar, S., Azabdaftari, G., Attwood, K., Scioneaux, R., Subramani, D., Manhardt, C., Lorusso, G. D., Willard, S. S., Thompson, H., et al. (2012). Serum Glutamate Levels Correlate with Gleason Score and Glutamate Blockade Decreases Proliferation, Migration, and Invasion and Induces Apoptosis in Prostate Cancer Cells. Clin Cancer Res 18, 5888-5901.

Lanier, L. L., Chang, C., Spits, H., and Phillips, J. H. (1992). Expression of cytoplasmic CD3 epsilon proteins in activated human adult natural killer (NK) cells and CD3 gamma, delta, epsilon complexes in fetal NK cells. Implications for the relationship of NK and T lymphocytes. J Immunol 149, 1876-1880.

Lin D, Gout P W and Wang Y. Lessons from in-vivo models of castration-resistant prostate cancer. Curr Opin Urol. 2013; 23(3):214-219.

Lisanti, M. P., Sotgia, F., Pestell, R. G., Howell, A., and Martinez-Outschoorn, U. E. (2013). Stromal glycolysis and MCT4 are hallmarks of DCIS progression to invasive breast cancer. Cell Cycle 12, 2935-2936.

Loriot, Y., Bianchini, D., Ileana, E., Sandhu, S., Patrikidou, A., Pezaro, C., Albiges, L., Attard, G., Fizazi, K., De Bono, J. S., et al. (2013). Antitumour activity of abiraterone acetate against metastatic castration-resistant prostate cancer progressing after docetaxel and enzalutamide (MDV3100). Ann Oncol 24, 1807-1812.

Manning Fox, J. E., Meredith, D., and Halestrap, A. P. (2000). Characterisation of human monocarboxylate transporter 4 substantiates its role in lactic acid efflux from skeletal muscle. J Physiol 529 Pt 2, 285-293.

Marchiq, I., Le Floch, R., Roux, D., Simon, M. P., and Pouysségur, J. (2015). Genetic Disruption of Lactate/H+ Symporters (MCTs) and Their Subunit CD147/BASIGIN Sensitizes Glycolytic Tumor Cells to Phenformin. Cancer Res 75, 171-180.

Matveeva, O. V., Tsodikov, A. D., Giddings, M., Freier, S. M., Wyatt, J. R., Spiridonov, A. N., Shabalina, S. A., Gesteland, R. F., and Atkins, J. F. (2000). Identification of sequence motifs in oligonucleotides whose presence is correlated with antisense activity. Nucleic Acids Res 28, 2862-2865.

Morice, W. G. (2007). The immunophenotypic attributes of NK cells and NK-cell lineage lymphoproliferative disorders. Am J Clin Pathol 127, 881-886.

Mullick, A. E., Fu, W., Graham, M. J., Lee, R. G., Witchell, D., Bell, T. A., Whipple, C. P., and Crooke, R. M. (2011). Antisense oligonucleotide reduction of apoB-ameliorated atherosclerosis in LDL receptor-deficient mice. J Lipid Res 52, 885-896.

Nadal, R., Schweizer, M., Kryvenko, O. N., Epstein, J. I., and Eisenberger, M. A. (2014). Small cell carcinoma of the prostate. Nat Rev Urol 11, 213-219.

Ning, Y. M., Pierce, W., Maher, V. E., Karuri, S., Tang, S. H., Chiu, H. J., Palmby, T., Zirkelbach, J. F., Marathe, D., Mehrotra, N., et al. (2013). Enzalutamide for treatment of patients with metastatic castration-resistant prostate cancer who have previously received docetaxel: U.S. Food and Drug Administration drug approval summary. Clin Cancer Res 19, 6067-6073.

Ohno, A., Yorita, K., Haruyama, Y., Kondo, K., Kato, A., Ohtomo, T., Kawaguchi, M., Marutuska, K., Chijiiwa, K., and Kataoka, H. (2014). Aberrant expression of monocarbohydrate transporter 4 (MCT4) in tumor cells predicts an unfavorable outcome in patients with hepatocellular carcinoma. Liver Int.

Ovens, M. J., Davies, A. J., Wilson, M. C., Murray, C. M., and Halestrap, A. P. (2010). AR-C155858 is a potent inhibitor of monocarboxylate transporters MCT1 and MCT2 that binds to an intracellular site involving transmembrane helices 7-10. Biochem J 425, 523-530.

Pan W H, Clawson G A. Identifying accessible sites in RNA: the first step in designing antisense reagents. Curr Med Chem. 2006; 13(25):3083-103.

Parks, S. K., Chiche, J., and Pouysségur, J. (2013). Disrupting proton dynamics and energy metabolism for cancer therapy. Nat Rev Cancer 13, 611-623.

Patzel V. In silico selection of active siRNA. Drug Discov Today. 2007 February; 12(3-4):139-48.

Peek A S, Behlke M A. Design of active small interfering RNAs. Curr Opin Mol Ther. 2007 April; 9(2):110-8.

Pértega-Gomes, N., Vizcaino, J. R., Miranda-Gongalves, V., Pinheiro, C., Silva, J., Pereira, H., Monteiro, P., Henrique, R. M., Reis, R. M., Lopes, C., et al. (2011). Monocarboxylate transporter 4 (MCT4) and CD147 overexpression is associated with poor prognosis in prostate cancer. BMC Cancer 11, 312.

Petrylak D P, Tangen C M, Hussain M H, Lara P N, Jr., Jones J A, Taplin M E, Burch P A, Berry D, Moinpour C, Kohli M, Benson M C, Small E J, Raghavan D and Crawford E D. Docetaxel and estramustine compared with mitoxantrone and prednisone for advanced refractory prostate cancer. N Engl J Med. 2004; 351(15):1513-1520.

Samuel, V. T., Choi, C. S., Phillips, T. G., Romanelli, A. J., Geisler, J. G., Bhanot, S., McKay, R., Monia, B., Shutter, J. R., Lindberg, R. A., et al. (2006). Targeting fox01 in mice using antisense oligonucleotide improves hepatic and peripheral insulin action. Diabetes 55, 2042-2050.

Sanità, P., Capulli, M., Teti, A., Galatioto, G. P., Vicentini, C., Chiarugi, P., Bologna, M., and Angelucci, A. (2014). Tumor-stroma metabolic relationship based on lactate shuttle can sustain prostate cancer progression. BMC Cancer 14, 154.

Shultz, L. D., Ishikawa, F., and Greiner, D. L. (2007). Humanized mice in translational biomedical research. Nat Rev Immunol 7, 118-130.

Siegel, R. L., Miller, K. D., and Jemal, A. (2015). Cancer statistics, 2015. CA Cancer J Clin 65, 5-29.

Tannock I F, de Wit R, Berry W R, Horti J, Pluzanska A, Chi K N, Oudard S, Theodore C, James N D, Turesson I, Rosenthal M A and Eisenberger M A. Docetaxel plus prednisone or mitoxantrone plus prednisone for advanced prostate cancer. N Engl J Med. 2004; 351(15):1502-1512.

Tennakoon, J. B., Shi, Y., Han, J. J., Tsouko, E., White, M. A., Burns, A. R., Zhang, A., Xia, X., Ilkayeva, O. R., Xin, L., et al. (2014). Androgens regulate prostate cancer cell growth via an AMPK-PGC-1α-mediated metabolic switch. Oncogene 33, 5251-5261.

Thomas, C., Zoubeidi, A., Kuruma, H., Fazli, L., Lamoureux, F., Beraldi, E., Monia, B. P., MacLeod, A. R., Thüroff, J. W., and Gleave, M. E. (2011). Transcription factor Stat5 knockdown enhances androgen receptor degradation and delays castration-resistant prostate cancer progression in vivo. Mol Cancer Ther 10, 347-359.

Ullah, M. S., Davies, A. J., and Halestrap, A. P. (2006). The plasma membrane lactate transporter MCT4, but not MCT1, is up-regulated by hypoxia through a HIF-1alpha-dependent mechanism. J Biol Chem 281, 9030-9037.

Vandesompele, J., De Preter, K., Pattyn, F., Poppe, B., Van Roy, N., De Paepe, A., and Speleman, F. (2002). Accurate normalization of real-time quantitative RT-PCR data by geometric averaging of multiple internal control genes. Genome Biol 3, RESEARCH0034.

Vaz, C. V., Alves, M. G., Marques, R., Moreira, P. I., Oliveira, P. F., Maia, C. J., and Socorro, S. (2012). Androgen-responsive and nonresponsive prostate cancer cells present a distinct glycolytic metabolism profile. Int J Biochem Cell Biol 44, 2077-2084.

Wang, Y., Xue, H., Cutz, J. C., Bayani, J., Mawji, N. R., Chen, W. G., Goetz, L. J., Hayward, S. W., Sadar, M. D., Gilks, C. B., et al. (2005). An orthotopic metastatic prostate cancer model in SCID mice via grafting of a transplantable human prostate tumor line. Lab Invest 85, 1392-1404.

Warburg, O. (1956). On respiratory impairment in cancer cells. Science 124, 269-270.

Yuan, T. C., Veeramani, S., and Lin, M. F. (2007). Neuroendocrine-like prostate cancer cells: neuroendocrine transdifferentiation of prostate adenocarcinoma cells. Endocr Relat Cancer 14, 531-547.

Zhang, Y., and Yang, J. M. (2013). Altered energy metabolism in cancer: a unique opportunity for therapeutic intervention. Cancer Biol Ther 14, 81-89.

What is claimed is:

1. A method of treating cancer in a subject, the method comprising
administering to the subject a therapeutically effective amount of the antisense oligonucleotide (ASO), wherein the ASO oligonucleotide has a sequence selected from the following:

(a) TCCCATGGCCAGGAGGGTTG; (SEQ ID NO: 1)

(b) GTCCCGGAAGACGCTCAGGT; (SEQ ID NO: 2)

(c) AAGGACGCAGCCACCATGCC; (SEQ ID NO: 3)

(d) TTGGCGTAGCTCACCACGAA; (SEQ ID NO: 4)

(e) AGATGCAGAAGACCACGAGG; (SEQ ID NO: 5)

(f) CCACTCTGGAATGACACGGT; (SEQ ID NO: 6)

(g) GTAGGAGAAGCCAGTGATGAC; (SEQ ID NO: 7)

(h) AGCATGGCCAGCAGGATGGA; (SEQ ID NO: 8)

(i) GGCTGGAAGTTGAGTGCCAA; (SEQ ID NO: 9)

(j) CATGCCGTAGGAGATGCCAA; (SEQ ID NO: 10)

(k) CTCAGGCTGTGGCTCTTTGG; (SEQ ID NO: 11)

(l) AGCACGGCCCAGCCCCAGCC; (SEQ ID NO: 13)

(m) GAGCTCCTTGAAGAAGACACT; (SEQ ID NO: 14)

(n) CAGGATGGAGGAGATCCAGG; (SEQ ID NO: 15)

(o) AGACCCCCACAAGCATGAC; (SEQ ID NO: 16)

(p) GAAGTTGAGTGCCAAACCCAA; (SEQ ID NO: 17)

(q) CCCGTTGGCCATGGGCGCC; (SEQ ID NO: 18)

(r) GCCAGCCCGTTGGCCATGGG; (SEQ ID NO: 19)

(s) AGGAAGACAGGGCTACCTGC; (SEQ ID NO: 20)

(t) GCACACAGGAAGACAGGGCT; (SEQ ID NO: 21)

(u) CAGGGCACACAGGAAGACAG; (SEQ ID NO: 22)

(v) CAGCAGTTGAGCAGCAGGCC; (SEQ ID NO: 23)

(w) ATGGCCAGGAGGGTTG; (SEQ ID NO: 46)

(x) CATGGCCAGGAGGGTT; (SEQ ID NO: 47)

(y) CCATGGCCAGGAGGGT; (SEQ ID NO: 48)
and (z) CCCATGGCCAGGAGGG; (SEQ ID NO: 49)

and wherein the ASO comprises a modified internucleoside linkage, a modified sugar moiety, or a modified nucleobase, and wherein the ASO is not longer than 21 nucleotides in length, and wherein the cancer is selected from one or more of the following: renal cell cancer; breast cancer; cervical cancer; liver cancer; bladder cancer; and lung cancer.

2. The method of claim 1, wherein the ASO further comprises a modified internucleoside linkage.

3. The method of claim 2, wherein the modified internucleoside linkage is a peptide-nucleic acid linkage, a morpholino linkage, a N3' to P5' phosphoramidate linkage, a methylphosphonate linkage or a phosphorothioate linkage.

4. The method of claim 1, wherein the ASO further comprises a modified sugar moiety.

5. The method of claim 4, wherein the modified sugar moiety is 2'-O-alkyl oligoribonucleotide.

6. The method of claim 1, wherein the ASO has a 2'MOE gapmer modification.

7. The method of claim 1, wherein the ASO further comprises a modified nucleobase.

8. The method of claim 7, wherein the modified nucleobase is a 5-methyl pyrimidine or a 5-propynyl pyrimidine.

9. The method of claim 1, wherein the cancer is characterized by elevated expression of MCT4.

10. The method of claim 1, wherein the ASO is complementary to the mRNA of MCT4.

11. The method of claim 1, wherein the ASO is administered intravenously.

12. The method of claim 1, wherein the ASO is topically administered to a tissue.

13. The method of claim 1, wherein the ASO is mixed with lipid particles prior to administration.

14. The method of claim 1, wherein the ASO is encapsulated in liposomes prior to administration.

15. The method of claim 2, wherein the ASO is encapsulated in liposomes prior to administration.

16. The method of claim 3, wherein the ASO is encapsulated in liposomes prior to administration.

17. The method of claim 4, wherein the ASO is encapsulated in liposomes prior to administration.

18. The method of claim 5, wherein the ASO is encapsulated in liposomes prior to administration.

19. The method of claim 6, wherein the ASO is encapsulated in liposomes prior to administration.

20. The method of claim 7, wherein the ASO is encapsulated in liposomes prior to administration.

21. The method of claim 8, wherein the ASO is encapsulated in liposomes prior to administration.

22. The method of claim 1, wherein the ASO comprises a modified internucleoside linkage; and a modified sugar moiety.

23. The method of claim 22, wherein the modified internucleoside linkage is a peptide-nucleic acid linkage, a morpholino linkage, a N3' to P5' phosphoramidate linkage, a methylphosphonate linkage or a phosphorothioate linkage; and the modified sugar moiety is 2'-O-alkyl oligoribonucleotide.

\* \* \* \* \*

SEQUENCE LISTING

```
<160> NUMBER OF SEQ ID NOS: 51

<210> SEQ ID NO 1
<211> LENGTH: 20
<212> TYPE: DNA
<213> ORGANISM: Homo sapiens

<400> SEQUENCE: 1
tcccatggcc aggagggttg                                              20

<210> SEQ ID NO 2
<211> LENGTH: 20
<212> TYPE: DNA
<213> ORGANISM: Homo sapiens

<400> SEQUENCE: 2
gtcccggaag acgctcaggt                                              20

<210> SEQ ID NO 3
<211> LENGTH: 20
<212> TYPE: DNA
<213> ORGANISM: Homo sapiens

<400> SEQUENCE: 3
aaggacgcag ccaccatgcc                                              20

<210> SEQ ID NO 4
<211> LENGTH: 20
<212> TYPE: DNA
<213> ORGANISM: Homo sapiens

<400> SEQUENCE: 4
ttggcgtagc tcaccacgaa                                              20

<210> SEQ ID NO 5
<211> LENGTH: 20
<212> TYPE: DNA
<213> ORGANISM: Homo sapiens

<400> SEQUENCE: 5
agatgcagaa gaccacgagg                                              20

<210> SEQ ID NO 6
<211> LENGTH: 20
<212> TYPE: DNA
<213> ORGANISM: Homo sapiens
```

```
<400> SEQUENCE: 6
ccactctgga atgacacggt                                              20

<210> SEQ ID NO 7
<211> LENGTH: 21
<212> TYPE: DNA
<213> ORGANISM: Homo sapiens

<400> SEQUENCE: 7
gtaggagaag ccagtgatga c                                            21

<210> SEQ ID NO 8
<211> LENGTH: 20
<212> TYPE: DNA
<213> ORGANISM: Homo sapiens

<400> SEQUENCE: 8
agcatggcca gcaggatgga                                              20

<210> SEQ ID NO 9
<211> LENGTH: 20
<212> TYPE: DNA
<213> ORGANISM: Homo sapiens

<400> SEQUENCE: 9
ggctggaagt tgagtgccaa                                              20

<210> SEQ ID NO 10
<211> LENGTH: 20
<212> TYPE: DNA
<213> ORGANISM: Homo sapiens

<400> SEQUENCE: 10
catgccgtag gagatgccaa                                              20

<210> SEQ ID NO 11
<211> LENGTH: 20
<212> TYPE: DNA
<213> ORGANISM: Homo sapiens

<400> SEQUENCE: 11
ctcaggctgt ggctctttgg                                              20

<210> SEQ ID NO 12
<211> LENGTH: 19
<212> TYPE: DNA
<213> ORGANISM: Homo sapiens

<400> SEQUENCE: 12
tagcggttca gcatgatga                                               19

<210> SEQ ID NO 13
<211> LENGTH: 20
<212> TYPE: DNA
<213> ORGANISM: Homo sapiens

<400> SEQUENCE: 13
agcacggccc agccccagcc                                              20

<210> SEQ ID NO 14
<211> LENGTH: 21
<212> TYPE: DNA
<213> ORGANISM: Homo sapiens
```

-continued

```
<400> SEQUENCE: 14
gagctccttg aagaagacac t                                             21

<210> SEQ ID NO 15
<211> LENGTH: 20
<212> TYPE: DNA
<213> ORGANISM: Homo sapiens

<400> SEQUENCE: 15
caggatggag gagatccagg                                               20

<210> SEQ ID NO 16
<211> LENGTH: 20
<212> TYPE: DNA
<213> ORGANISM: Homo sapiens

<400> SEQUENCE: 16 agaccccca caagcatgac                                                20

<210> SEQ ID NO 17
<211> LENGTH: 21
<212> TYPE: DNA
<213> ORGANISM: Homo sapiens

<400> SEQUENCE: 17
gaagttgagt gccaaaccca a                                             21

<210> SEQ ID NO 18
<211> LENGTH: 20
<212> TYPE: DNA
<213> ORGANISM: Homo sapiens

<400> SEQUENCE: 18
cccgttggcc atggggcgcc                                               20

<210> SEQ ID NO 19
<211> LENGTH: 20
<212> TYPE: DNA
<213> ORGANISM: Homo sapiens

<400> SEQUENCE: 19
gccagcccgt tggccatggg                                               20

<210> SEQ ID NO 20
<211> LENGTH: 20
<212> TYPE: DNA
<213> ORGANISM: Homo sapiens

<400> SEQUENCE: 20
aggaagacag ggctacctgc                                               20

<210> SEQ ID NO 21
<211> LENGTH: 20
<212> TYPE: DNA
<213> ORGANISM: Homo sapiens

<400> SEQUENCE: 21
gcacacagga agacagggct                                               20

<210> SEQ ID NO 22
<211> LENGTH: 20
<212> TYPE: DNA
```

<213> ORGANISM: Homo sapiens

<400> SEQUENCE: 22
cagggcacac aggaagacag                                                  20

<210> SEQ ID NO 23
<211> LENGTH: 20
<212> TYPE: DNA
<213> ORGANISM: Homo sapiens

<400> SEQUENCE: 23
cagcagttga gcagcaggcc                                                  20

<210> SEQ ID NO 24
<211> LENGTH: 20
<212> TYPE: DNA
<213> ORGANISM: Homo sapiens

<400> SEQUENCE: 24
gacctgtccc gtagagcatg                                                  20

<210> SEQ ID NO 25
<211> LENGTH: 20
<212> TYPE: DNA
<213> ORGANISM: Homo sapiens

<400> SEQUENCE: 25
ttcccaagcc ccgccacgaa                                                  20

<210> SEQ ID NO 26
<211> LENGTH: 20
<212> TYPE: DNA
<213> ORGANISM: Homo sapiens

<400> SEQUENCE: 26
aatgctccac ctcccgcaag                                                  20

<210> SEQ ID NO 27
<211> LENGTH: 20
<212> TYPE: DNA
<213> ORGANISM: Homo sapiens

<400> SEQUENCE: 27
acctccccgt ttttctcagg                                                  20

<210> SEQ ID NO 28
<211> LENGTH: 20
<212> TYPE: DNA
<213> ORGANISM: Homo sapiens

<400> SEQUENCE: 28
tgtgaaccac ctccccgttt                                                  20

<210> SEQ ID NO 29
<211> LENGTH: 20
<212> TYPE: DNA
<213> ORGANISM: Homo sapiens

<400> SEQUENCE: 29
tctgtacctc ctccctgtgc                                                  20

<210> SEQ ID NO 30
<211> LENGTH: 20

<212> TYPE: DNA
<213> ORGANISM: Homo sapiens

<400> SEQUENCE: 30
gaatgacacg gttcccaccc                                              20

<210> SEQ ID NO 31
<211> LENGTH: 20
<212> TYPE: DNA
<213> ORGANISM: Homo sapiens

<400> SEQUENCE: 31
gcccacccac cctcccatta                                              20

<210> SEQ ID NO 32
<211> LENGTH: 20
<212> TYPE: DNA
<213> ORGANISM: Homo sapiens

<400> SEQUENCE: 32
aagagacccc ccacaagcat                                              20

<210> SEQ ID NO 33
<211> LENGTH: 20
<212> TYPE: DNA
<213> ORGANISM: Homo sapiens

<400> SEQUENCE: 33
cccaccatgc cgtaggagat                                              20

<210> SEQ ID NO 34
<211> LENGTH: 20
<212> TYPE: DNA
<213> ORGANISM: Homo sapiens

<400> SEQUENCE: 34
agtccacccc cgagtctgca                                              20

<210> SEQ ID NO 35
<211> LENGTH: 20
<212> TYPE: DNA
<213> ORGANISM: Homo sapiens

<400> SEQUENCE: 35
cttcaccgca gatccactct                                              20

<210> SEQ ID NO 36
<211> LENGTH: 20
<212> TYPE: DNA
<213> ORGANISM: Homo sapiens

<400> SEQUENCE: 36
aacactccac ccacacgcag                                              20

<210> SEQ ID NO 37
<211> LENGTH: 20
<212> TYPE: DNA
<213> ORGANISM: Homo sapiens

<400> SEQUENCE: 37
ccagccactc agacacttgt                                              20

<210> SEQ ID NO 38

-continued

```
<211> LENGTH: 20
<212> TYPE: DNA
<213> ORGANISM: Homo sapiens

<400> SEQUENCE: 38
ggccaccgcc tccatcagca                                                 20

<210> SEQ ID NO 39
<211> LENGTH: 20
<212> TYPE: DNA
<213> ORGANISM: Homo sapiens

<400> SEQUENCE: 39
cctgagccag tccagtttgt                                                 20

<210> SEQ ID NO 40
<211> LENGTH: 20
<212> TYPE: DNA
<213> ORGANISM: Homo sapiens

<400> SEQUENCE: 40
cccacccacc ctcccattaa                                                 20

<210> SEQ ID NO 41
<211> LENGTH: 20
<212> TYPE: DNA
<213> ORGANISM: Homo sapiens

<400> SEQUENCE: 41
gcttctgtac ctcctccctg                                                 20

<210> SEQ ID NO 42
<211> LENGTH: 19
<212> TYPE: DNA
<213> ORGANISM: Homo sapiens

<400> SEQUENCE: 42
tgtcgctgta gccgatccc                                                  19

<210> SEQ ID NO 43
<211> LENGTH: 19
<212> TYPE: DNA
<213> ORGANISM: Homo sapiens

<400> SEQUENCE: 43
ttaaagtcac gttgtctcg                                                  19

<210> SEQ ID NO 44
<211> LENGTH: 19
<212> TYPE: DNA
<213> ORGANISM: Homo sapiens

<400> SEQUENCE: 44
ttgcggcttg gcttcaccg                                                  19

<210> SEQ ID NO 45
<211> LENGTH: 22
<212> TYPE: DNA
<213> ORGANISM: Rattus norvegicus

<400> SEQUENCE: 45
cacagctcct cccatggcca gg                                              22
```

```
<210> SEQ ID NO 46
<211> LENGTH: 16
<212> TYPE: DNA
<213> ORGANISM: Homo sapiens

<400> SEQUENCE: 46
atggccagga gggttg                                                   16

<210> SEQ ID NO 47
<211> LENGTH: 16
<212> TYPE: DNA
<213> ORGANISM: Homo sapiens

<400> SEQUENCE: 47
catggccagg agggtt                                                   16

<210> SEQ ID NO 48
<211> LENGTH: 16
<212> TYPE: DNA
<213> ORGANISM: Homo sapiens

<400> SEQUENCE: 48
ccatggccag gagggt                                                   16

<210> SEQ ID NO 49
<211> LENGTH: 16
<212> TYPE: DNA
<213> ORGANISM: Homo sapiens

<400> SEQUENCE: 49
cccatggcca ggaggg                                                   16

<210> SEQ ID NO 50
<211> LENGTH: 16
<212> TYPE: DNA
<213> ORGANISM: Homo sapiens

<400> SEQUENCE: 50
tcccatggcc aggagg                                                   16

<210> SEQ ID NO 51
<211> LENGTH: 20
<212> TYPE: DNA
<213> ORGANISM: Artificial Sequence
<220> FEATURE:
<223> OTHER INFORMATION: MCT4 Control ASO

<400> SEQUENCE: 51
ccttccctga aggttcctcc                                               20
```